US008907384B2

(12) United States Patent
Pace et al.

(10) Patent No.: US 8,907,384 B2
(45) Date of Patent: Dec. 9, 2014

(54) CNT-BASED SENSORS: DEVICES, PROCESSES AND USES THEREOF

(75) Inventors: Salvatore J. Pace, Newark, DE (US); Piu Francis Man, Wilmington, DE (US); Ajeeta Pradip Patil, Wilmington, DE (US); Kah Fatt Tan, Klang Selangor Darul Ehsan (MY)

(73) Assignee: NanoSelect, Inc., Wilmington, DE (US)

( * ) Notice: Subject to any disclaimer, the term of this patent is extended or adjusted under 35 U.S.C. 154(b) by 1456 days.

(21) Appl. No.: 12/161,294

(22) PCT Filed: Jan. 26, 2007
(Under 37 CFR 1.47)

(86) PCT No.: PCT/US2007/002104
§ 371 (c)(1),
(2), (4) Date: Oct. 27, 2009

(87) PCT Pub. No.: WO2007/089550
PCT Pub. Date: Aug. 9, 2007

(65) Prior Publication Data
US 2011/0163296 A1    Jul. 7, 2011

Related U.S. Application Data

(60) Provisional application No. 60/762,788, filed on Jan. 26, 2006.

(51) Int. Cl.
*H01L 21/66*    (2006.01)
*G01N 27/414*   (2006.01)
*B82Y 15/00*    (2011.01)
*B82Y 30/00*    (2011.01)

(52) U.S. Cl.
CPC .............. *G01N 27/414* (2013.01); *B82Y 15/00* (2013.01); *B82Y 30/00* (2013.01); *Y10S 977/742* (2013.01); *Y10S 977/748* (2013.01); *Y10S 977/749* (2013.01); *Y10S 977/752* (2013.01)
USPC ........... 257/253; 977/742; 977/748; 977/749; 977/752

(58) Field of Classification Search
USPC ................................. 977/745–749
See application file for complete search history.

(56) References Cited

U.S. PATENT DOCUMENTS 5,120,421 A    6/1992  Glass et al.
5,457,343 A   10/1995  Ajayan et al.
(Continued)

FOREIGN PATENT DOCUMENTS

EP      0012035       6/1980
WO      WO 99/60169 A1   11/1999
(Continued)

OTHER PUBLICATIONS

U.S. Appl. No. 60/762,788, filed Jan. 26, 2006, Salvatore J. Pace.
(Continued)

*Primary Examiner* — Matthew W Such
*Assistant Examiner* — Abul Kalam
(74) *Attorney, Agent, or Firm* — Duane Morris LLP

(57) ABSTRACT

Disclosed herein are methods of preparing and using doped MWNT electrodes, sensors and field-effect transistors. Devices incorporating doped MWNT electrodes, sensors and field-effect transistors are also disclosed.

87 Claims, 68 Drawing Sheets

(56) References Cited

U.S. PATENT DOCUMENTS

| | | | |
|---|---|---|---|
| 6,066,448 A | 5/2000 | Wohlstadter et al. | |
| 6,232,706 B1 | 5/2001 | Dai et al. | |
| 6,278,231 B1 | 8/2001 | Iwasaki et al. | |
| 6,340,822 B1 | 1/2002 | Brown et al. | |
| 6,350,609 B1 | 2/2002 | Morozov et al. | |
| 6,423,193 B1 | 7/2002 | Miller et al. | |
| 6,528,020 B1 | 3/2003 | Dai et al. | |
| 6,544,463 B1 | 4/2003 | Luzzi et al. | |
| 6,627,450 B1 | 9/2003 | Taylor et al. | |
| 6,656,712 B1* | 12/2003 | Balavoine et al. | 435/176 |
| 6,672,077 B1 | 1/2004 | Bradley et al. | |
| 6,673,226 B1 | 1/2004 | Kogan et al. | |
| 6,748,748 B2 | 6/2004 | Bradley et al. | |
| 6,755,956 B2 | 6/2004 | Lee et al. | |
| 6,831,017 B1* | 12/2004 | Li et al. | 438/694 |
| 6,834,508 B2 | 12/2004 | Bradley et al. | |
| 6,863,857 B2 | 3/2005 | Luzzi et al. | |
| 6,894,359 B2 | 5/2005 | Bradley et al. | |
| 6,905,655 B2 | 6/2005 | Gabriel et al. | |
| 6,962,823 B2 | 11/2005 | Empedocles et al. | |
| 6,986,258 B2 | 1/2006 | Bradley et al. | |
| 6,991,773 B2 | 1/2006 | Jhi et al. | |
| 7,013,708 B1 | 3/2006 | Cho et al. | |
| 7,056,455 B2 | 6/2006 | Matyjaszewski et al. | |
| 7,094,679 B1 | 8/2006 | Li et al. | |
| 7,147,894 B2 | 12/2006 | Zhou et al. | |
| 7,171,312 B2 | 1/2007 | Steinthal et al. | |
| 7,186,355 B2 | 3/2007 | Swager | |
| 7,189,314 B1 | 3/2007 | Pace et al. | |
| 7,217,354 B2 | 5/2007 | Mahurin et al. | |
| 7,250,147 B2 | 7/2007 | Tour et al. | |
| 7,291,503 B2 | 11/2007 | Swager | |
| 7,332,222 B2 | 2/2008 | Luzzi et al. | |
| 7,347,974 B1 | 3/2008 | Snow et al. | |
| 7,355,216 B2 | 4/2008 | Yang et al. | |
| 7,407,566 B2 | 8/2008 | Jiang et al. | |
| 7,537,807 B2 | 5/2009 | Craighead et al. | |
| 7,692,218 B2* | 4/2010 | Barron et al. | 257/253 |
| 2002/0042686 A1 | 4/2002 | Kobayashi et al. | |
| 2002/0152036 A1 | 10/2002 | Martin | |
| 2003/0046980 A1 | 3/2003 | Kiesele et al. | |
| 2003/0077515 A1 | 4/2003 | Chen et al. | |
| 2003/0134433 A1 | 7/2003 | Gabriel et al. | |
| 2003/0167778 A1 | 9/2003 | Bradley et al. | |
| 2004/0022677 A1 | 2/2004 | Wohlstadter et al. | |
| 2004/0038251 A1 | 2/2004 | Smalley et al. | |
| 2004/0048241 A1 | 3/2004 | Freeman et al. | |
| 2004/0132070 A1 | 7/2004 | Star et al. | |
| 2004/0157263 A1 | 8/2004 | Diessel et al. | |
| 2004/0211731 A1 | 10/2004 | Ferguson et al. | |
| 2004/0253741 A1 | 12/2004 | Star et al. | |
| 2005/0011771 A1 | 1/2005 | Wittkampf et al. | |
| 2005/0027180 A1 | 2/2005 | Goode et al. | |
| 2005/0029103 A1 | 2/2005 | Feng et al. | |
| 2005/0041458 A1 | 2/2005 | Lossau et al. | |
| 2005/0110024 A1 | 5/2005 | Swain et al. | |
| 2005/0186333 A1* | 8/2005 | Douglas | 427/97.1 |
| 2005/0191417 A1 | 9/2005 | Fan | |
| 2005/0230270 A1* | 10/2005 | Ren et al. | 205/777.5 |
| 2005/0244811 A1* | 11/2005 | Soundarrajan et al. | 435/4 |
| 2005/0285599 A1 | 12/2005 | Harima | |
| 2006/0014155 A1 | 1/2006 | Hamers et al. | |
| 2006/0032743 A1 | 2/2006 | Harima | |
| 2006/0096870 A1 | 5/2006 | Sheu et al. | |
| 2006/0115640 A1* | 6/2006 | Yodh et al. | 428/221 |
| 2006/0165587 A1* | 7/2006 | Lee | 423/447.1 |
| 2006/0243603 A1 | 11/2006 | Jiang et al. | |
| 2007/0037057 A1 | 2/2007 | Douglas | |
| 2007/0065337 A1 | 3/2007 | Jiang et al. | |
| 2007/0108068 A1 | 5/2007 | Suh et al. | |
| 2007/0114137 A1 | 5/2007 | Nomura et al. | |
| 2008/0135404 A1 | 6/2008 | Rowe et al. | |
| 2009/0269921 A1* | 10/2009 | Kawabata et al. | 438/652 |
| 2011/0163296 A1 | 7/2011 | Pace et al. | |

FOREIGN PATENT DOCUMENTS

| | | |
|---|---|---|
| WO | WO 99/63347 A2 | 12/1999 |
| WO | WO 03/093169 | 11/2003 |
| WO | WO 2004/036217 A1 | 4/2004 |
| WO | WO 2004/040671 A2 | 5/2004 |
| WO | WO 2004/052447 A1 | 6/2004 |
| WO | WO 2005/026694 A2 | 3/2005 |
| WO | WO 2006/071867 | 7/2006 |
| WO | WO 2007/089550 A2 | 8/2007 |
| WO | WO 2007/089650 | 8/2007 |

OTHER PUBLICATIONS

U.S. Appl. No. 60/762,613, filed Jan. 26, 2006, Piu Francis Man.

Auvray et al., "Chemical optimization of self-assembled carbon nanotube transistors", Nano Lett., Mar. 2005, 5 (3), 451-455.

Bekyarova al., "Chemically functionlized single-walled carbon nanotubes as ammonia sensors", J. Phys. Chem. B, Oct. 9, 2004, 108 (51), 19717-19720.

Bond et al., "Fundamental and second Harmonic alternating current cyclic voltammetric theory and experimental results for simple electrode reactions involving solution-soluble redox couples", Analytical Chemistry, May 1976, 48(6), 872-883.

Bradley et al., "Influence of mobile ions on nanotube based FET devices", Nano Letters, May 2003, 3(5), 639-641.

Ceresa et al., "Rational Design of potentiometric trace level ion sensors. A Ag+-selective electrode with a 100 ppt detection limit", Analytical Chemistry, Aug. 15, 2002, 74(16), 4027-4036.

Chandrasekaran et al., "Detecting molecules: the commercialization of sensors", Nanotechnology Law & Business Journal, 2005, 2(1), 1-16.

Chatelier et al., "Theory of Contact Angles and the Free Energy of Formation of Ionizable Surfaces: Application to Heptylamine Radio-Frequency Plasma-Deposited Films", Langmuir, Jun. 29, 1995, 11(10),4122-4128.

Chen et al., "Electrochemical characterization of carbon nanotubes as electrode in electrochemical double-layer capacitors", Carbon, Jul. 2002, 40, 1193-1197.

Chen et al., "Electrochemical synthesis of polypyrrole films over each of well-aligned carbon nanotubes", Synthetic Metals, Dec. 20, 2001, 125, 289-294.

Chen et al., "Electrochemical synthesis of polypyrrole/carbon nanotube nanoscale composites using well-aligned carbon nanotube arrays", Appl. Phys. A, Jun. 20, 2001, 73, 129-131.

Chen et al., "Well-aligned graphitic nanofibers synthesized by plasma-assisted chemical vapor deposition", Chem. Physics Letters, Jun. 27, 1997, 272, 178-182.

Chen, "Exploratory research on carbon nanotube arrays as nanoelectrodes for use in electrochemistry", Proceedings of the 199th Meeting of Electrochemical Society, Washington, DC, Mar. 25-29, 2001, 1-4.

Chu et al., "Electrocatalytic oxidation of glucose on carbon nanotube/nanocrystalline TiO2 film loaded Pt complex electrode", Atca Chimica Sinica, Dec. 28, 2004, 62(24), 2403-2406.

Deo et al., "Determination of organophosphate pesticides at a carbon nanotube/organophosphorus hydrolase electrochemical biosensor", Analytica Chimica Acta, Feb. 14, 2005, 530(2), 185-189.

Dong et al., "Synthesis and redox behavior of bioferrocenyl-functionalized ruthenium(II) terpyridine gold clusters", Langmuir, Jun. 26, 2004, 20, 9340-9347.

El-Aguizy et al., "Transplanting carbon nanotubes", Applied Physics Letters, Dec. 13, 2004, (85)24, 5995-5997.

Fei et al., "Electrochemical behavior of L-cysteine and its detection at carbon nanotube electrode modified with platinum", Analytical biochemistry, Apr. 1, 2005, 339(1), 29-35.

Fu et al., "Effects of ionic surfactant adsorption on single-walled carbon nanotube thin film devices in aqueous solutions", Langmuir, Feb. 15, 2005, 21(4), 1162-1165.

Gangloff et al., "Self-aligned, gated arrays of individual nanotube and nanowire emitters", Nano Letters, Jul. 29, 2004, 4(9), 1575-1579.

(56) References Cited

OTHER PUBLICATIONS

Goldberg et al., "Fine structure of boron nitride nanotubes produced from carbon nanotubes by a substitution reaction", J. of Applied Physicals, Aug. 15, 1999, 86(4), 2364-2366.
Guo et al., "Electrogenerated chemiluminescence from $Ru(Bpy)_3^{2+}$ ion-exchanged in carbon nanotube/perfluorosulfonated ionomer composite films", Analytical Chemistry, May 15, 2004, 76(10) 2683-2688.
Hayes et al., "Some observations on digital smoothing of electroanalytical data based on the fourier transformation", Analytical Chemistry, Feb. 1973, 45(2), 277-284.
Heller et al., "Individual Single-walled carbon nanotubes as nanoelectrodes for electrochemistry", Nano Letters, Oct. 31, 2004, A-F.
Hochbaum et al., Controlled Growth of Si Nanowire Arrays for Device Integration, Nano Letters, Jan. 2005, vol. 5, No. 3, 457-460.
Hsieh et al., "Surface "priming" for layer-by-layer deposition: polyelectrolyte multilayer formation on alkylamine plasma-modified polytetrafluoroethylene", J. Macromolecules, Dec. 29, 1997, 30, 8453-8458.
Huang et al., "Growth of large periodic arrays of carbon nanotubes", Applied Physics Letters, Jan. 20, 2003, 82(3), 460-462.
Huang et al., "Patterned Growth and Contact Transfer of Well-Aligned Carbon Nanotube Films", J. Phys. Chem. B, May 7, 1999, 103, 4223-4227.
Ionescu et al., "Construction of amperometric immunosensors based on the electrogeneration of a permeable biotinylated polypyrrole film", Analytical Chemistry, Nov. 15, 2004, 76(22), 6808-6813.
Iriyama et al., "Plasma surface treatment on nylon fabrics by fluorocarbon compounds", J. Appl. Polym. Sci., Jan. 20, 1990, 39(2), 249-264.
Javey et al., "High performance n-type carbon nanotube field-effect transistors with chemically doped contacts", Nano Letters, Dec. 14, 2004, 0(0), A-D.
Jayasinghe et al., "An advanced jet-based approach to processing nanotubes", Physica E-Low_Dimensional Systems and Nanostructures, Nov. 2005, 31(1), 17-26.
Jo et al., "Correlation of field emission and surface microstructure of vertically aligned carbon nanotubes", Applied Physics Letters, Jan. 10, 2004, 84(3), 413-415.
Jo et al., "Effect of length and spacing of vertically aligned carbon nanotubes on field emission properties", Applied Physics Letters, May 19, 2003, 82(20), 3520-3522.
Koehne et al., "The fabrication and electrochemical characterization of carbon nanotube nanoelectrode arrays", J. of Materials Chemistry, 2004, 14(4) 676-684.
Koo et al., "High inversion current in silicon nanowire field effect transistors", Aug. 20, 2004, 4(11), 2197-2201.
Lee et al., "Fabrication of a single-walled carbon nanotube (SWCNT) device using a novel barricade-confronting electrode (BCE) pattern for gas sensor applications", Sensors and Materials, 2004, 16(7), 357-365.
Li et al., "Carbon Nanotube nanoelectrode array for ultrasensitive DNA detection", Nano Letters, Mar. 23, 2003, 3(5), 597-602.
Li et al., "Clean double-walled carbon nanotubes synthesized by CVD", Chemical Physics Letters, Jan. 17, 2003, 368, 299-306.
Li et al., "Effect of gas pressure on the growth and structure of carbon nanotubes by chemical vapor deposition", Appl. Phys. A, Jun. 20, 2001, 73, 259-264.
Li et al., "Study of carbon nanotube modified biosensor for monitoring total cholesterol in blood", Biosensors & Bioelectronics, Apr. 15, 2005, 20(10), 2140-2144.
Li et al., "Study of the self-sustaining discharge gas sensor with a carbon nanotube cathode", Surface and Interface Analysis, May-Jun. 2004, 36(5-6), 474-477.
Lin et al., "Glucose biosensors based on carbon nanotube nanoelectrode ensembles", Feb. 2004, 4(2), 191-195.
Medintz et al., "General strategy for biosensor design and construction employing multifunctional surface-tethered components", Anal. Chem., Oct. 1, 2004, 76, 5620-5629.

Miao et al., "Electrogenerated Chemiluminescence. 77. DNA hybridization detection at high amplification with $[Ru(bpy)_3]^{2+}$-containing microspheres", Analytical Chemistry, Sep. 15, 2004, 76(18), 5379-5386.
Moser et al., "Individual Free-standing carbon nanofibers addressable on the 50 nm scale", J. Vac. Sci. Technol. B, May/Jun. 2003, 21(3), 1004-1007.
Naguib et al., "Observation of water confined in nanometer channels of closed carbon nanotubes", Nano Letters, Sep. 15, 2004, 4(11), 2237-2243.
O'Connor et al., "Mediated amperometric immunosensing using single walled carbon nanotube forests", The Analyst, Nov. 12, 2004, 129(12) 1176-1180.
O'Shea et al., "Electrospray deposition of carbon nanotubes in vacuum", Nanotechnology, Jan. 2007, 18(3), 35707.
Qi et al., "Miniature organic transistors with carbon nanotubes as quasi-one-dimensional electrodes", J. Am. Chem. Soc., Aug. 23, 2004, 11774-11775.
Qi et al., "Toward large arrays of multiplex functionalized carbon nanotube sensor for highly sensitive and selective molecular detection", Nano Letters, Jan. 2003, 3(3), 347-351.
Ren et al., "Growth of a single freestanding multiwall carbon nanotube on each nanonickel dot", Applied Physics Letters, Aug. 23, 1999, 75(8), 1086-1088.
Ren et al., "Large arrays of well-aligned carbon nanotubes", Proceedings of 13th International Winter School on Electronic Properties of Novel Materials, Mar. 6, 1999, 263-267.
Ren et al., "Synthesis of large arrays of well-aligned carbon nanotubes on glass", Science, Nov. 6, 1998, 282, 1105-1107.
Smith, "The acquisition of electrochemical response spectra by on-line fast fourier transform", Analytical Chemistry, Feb. 1976, 48(2), 221A-240A.
Smith, "The enhancement of electroanalytical data by on-line fast fourier transform", Analytical Chemistry, May 1976, 48(6), 517A-526A.
Snyder et al., "Molecular genetics of bacteria", ASM Press, Wash. DC, 1997, 1-17.
Star et al., "Nanoelectronic carbon dioxide sensors", Advanced Materials, Nov. 18, 2004, 16(22), 2048-2052.
Suh et al., "Highly ordered two-dimensional carbon nanotube arrays", Applied Physics Letters, Oct. 4, 1999, 75(14), 2047-2049.
Terlingen et al., "Immobilization of Surface Active Compounds on Polymer Supports Using Glow Discharge Processes: 1. Sodium Dodecyl Sulfate on Poly(propylene)", Colloid Interface Sci., Jan. 1993, 155(1), 55-65.
Terlingen et al., "Introduction of functional groups on polyethylene surfaces by a carbon dioxide plasma treatment", J. App Polym Sci., Aug. 22, 1995, 57(8), 969-982.
Tseng et al., "Monolithic integration of carbon nanotube devices with silicon MOS technology", Nano Letters, Jan. 2004, 4(1), 123-127.
Tu et al., "Carbon nanotubes based nanoelectrode arrays: fabrication, evaluation, and application in voltammetric analysis", Electroananlysis, Jan. 2005, 17(1), 79-84.
Tu et al., "Growth of aligned carbon nanotubes with controlled site density", Applied Physics Letters, May 27, 2002, 80(21), 4018-4020.
Tu et al., "Nanoelectrode arrays based on low site density aligned carbon nanotubes", Nano Letters, 2003, Dec. 12, 2002, 3(1), 107-109.
Wang et al., "Periodicity and alignment of large-scale carbon nanotubes arrays", Applied Physics Letters, Nov. 15, 2004, 85(20), 4741-4743.
Wen et al., "Growth and characterization of aligned carbon nanotubes from patterned nickel nanodots and uniform thin films", J. Mater. Res., Nov. 2001, 16(11), 3246-3253.
Xu et al., "Single-wall carbon nanotube-based voltammetric sensor and biosensor", Biosensors & Bioelectronics, Oct. 15, 2004, 20(3), 579-584.
Ye et al., "Electrochemical biosensing platforms using phthalocyanine-functionalized carbon nanotube electrode", Electroanalysis, Jan. 2005, 17(1), 89-96.
Ye et al., "Selective voltammetric detection of uric acid in the presence of ascorbic acid at well-aligned carbon nanotube electrode", Electroanalysis, Nov. 2003, 15(21), 1693-1698.

(56) References Cited

OTHER PUBLICATIONS

Zhao et al., "Electronic properties of carbon nanotubes with covalent sidewall functionalization", J. Phys. Chem. B, Mar. 11, 2004, 108(14), 4227-4230.

Zhao et al., "Water-soluble and optically pH-sensitive single-walled carbon nanotubes from surface modification", J. Am. Chem. Soc., Sep. 27, 2002, 124(42), 12418-12419.

Campo et al., "Improved Free Chlorine Amperometric Sensor Chip for Drinking Water Applications", Analytica Chimica Acta, Aug. 10, 2005, 554, 98-104.

Kishioka et al., "Electrochemical Determination of a Free Chlorine Residual Using Cathodic Potential-Step Chronocoulometry", Electroanalysis, Jul. 2, 2004, 17(8), 724-726.

Lowe et al., "Edge Plane Pyrolytic Graphite Electrodes for Halide Detection in Aqueous Solutions", Electroanalysis, Mar. 21, 2005, 17(18), 1627-1634.

Ordeig et al., "Continuous Detection of Hypochlorous Acid/Hypochlorite for Water Quality Monitoring and Control", Electroanalysis, Jan. 13, 2005, 17(18), 1641-1648.

\* cited by examiner

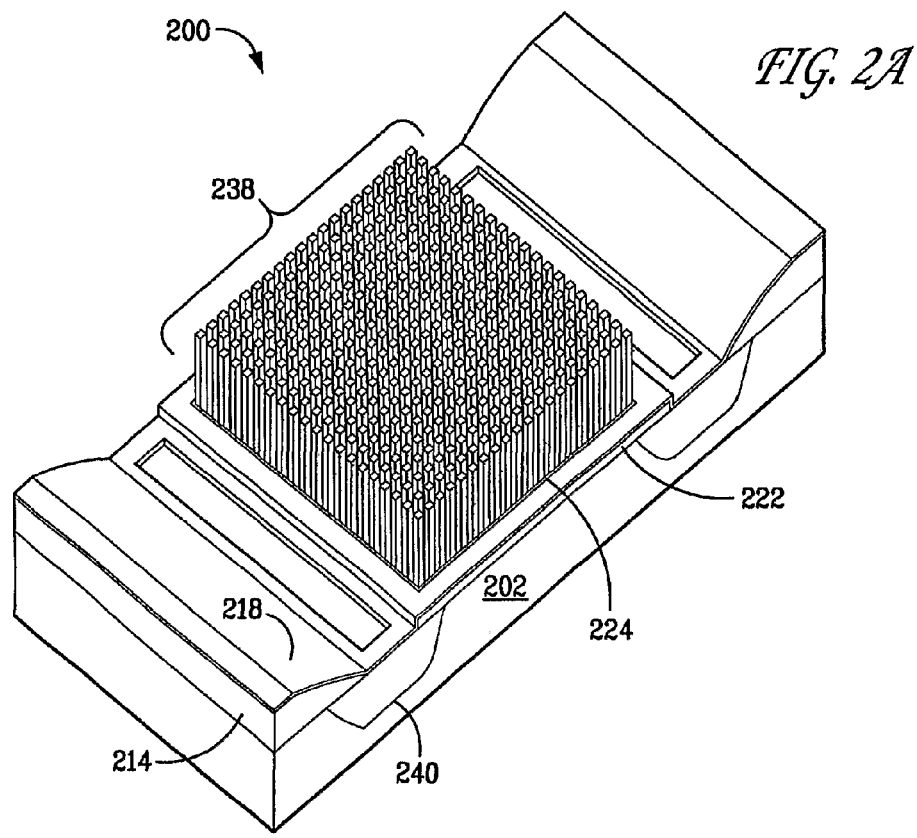
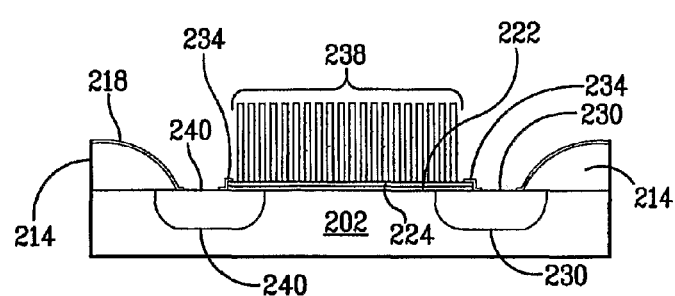

FIG. 6
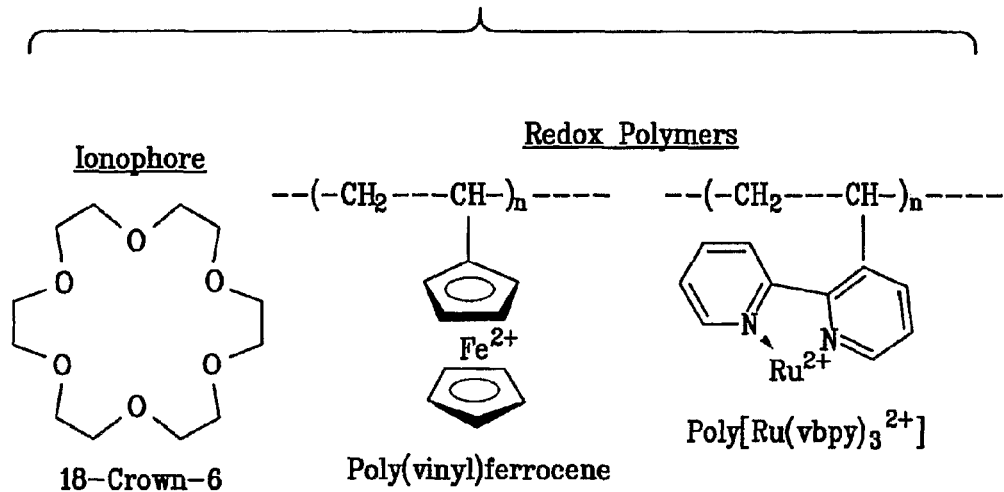
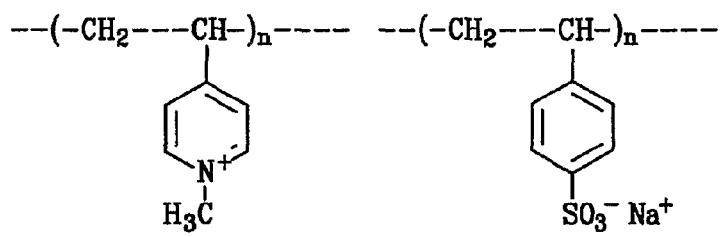
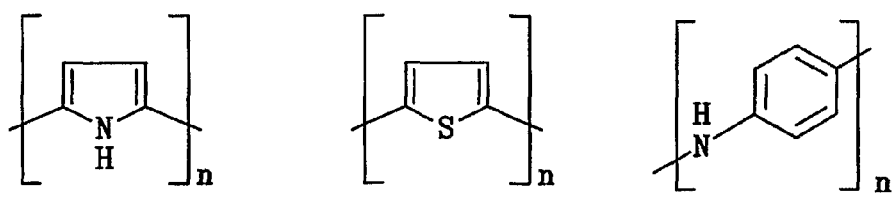

FIG. 7
CNT p-n character modifiers/dopants
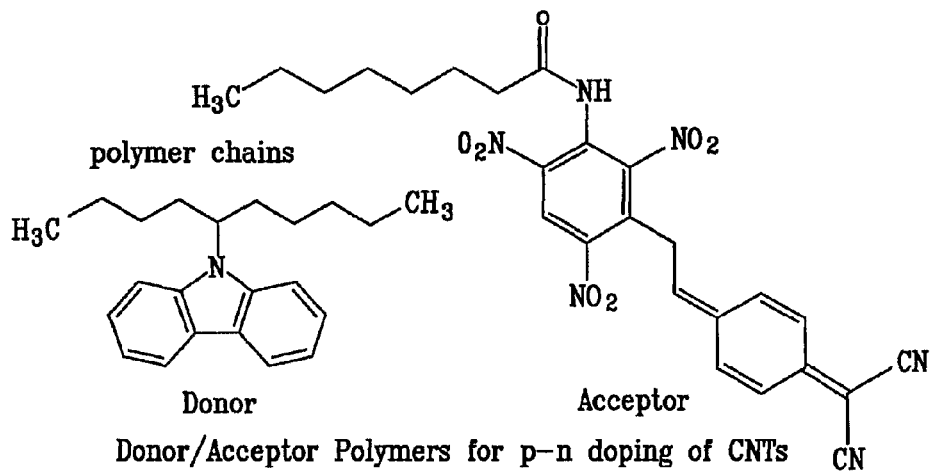
Donor/Acceptor Polymers for p-n doping of CNTs
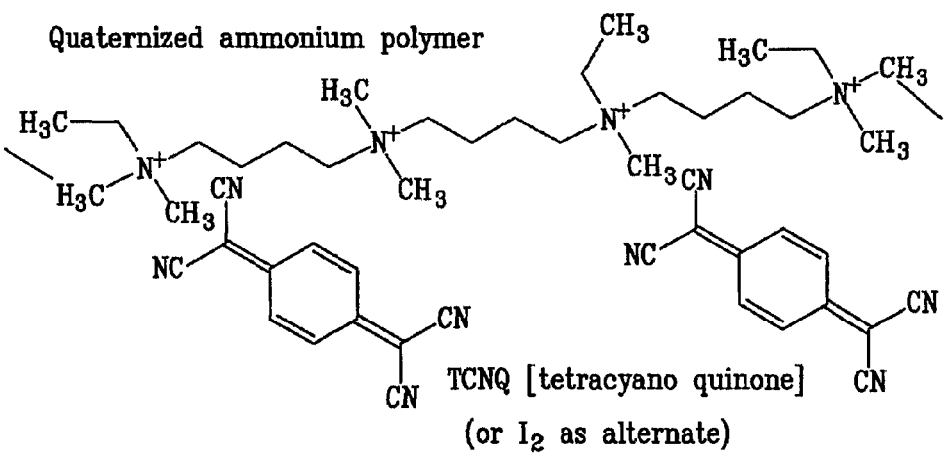
TCNQ [tetracyano quinone]
(or $I_2$ as alternate)
Electrochemical Reaction
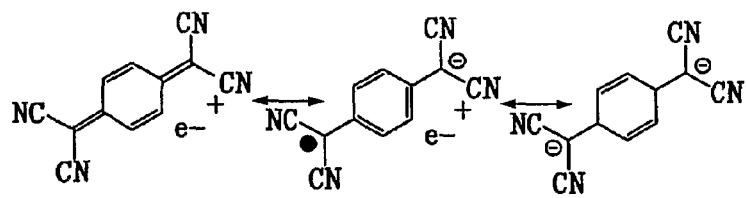

Charge-Coupled Devices

Calcium Ion Selective Sensor

Ammonia Sensor

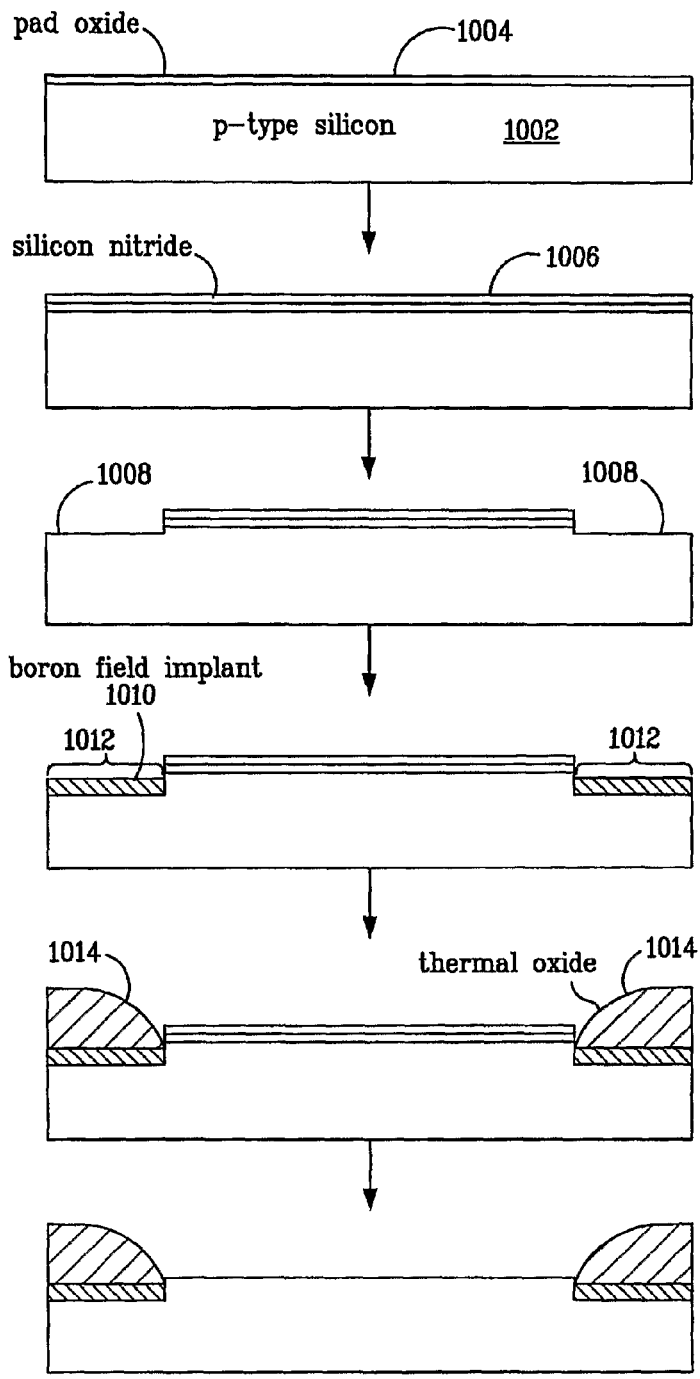

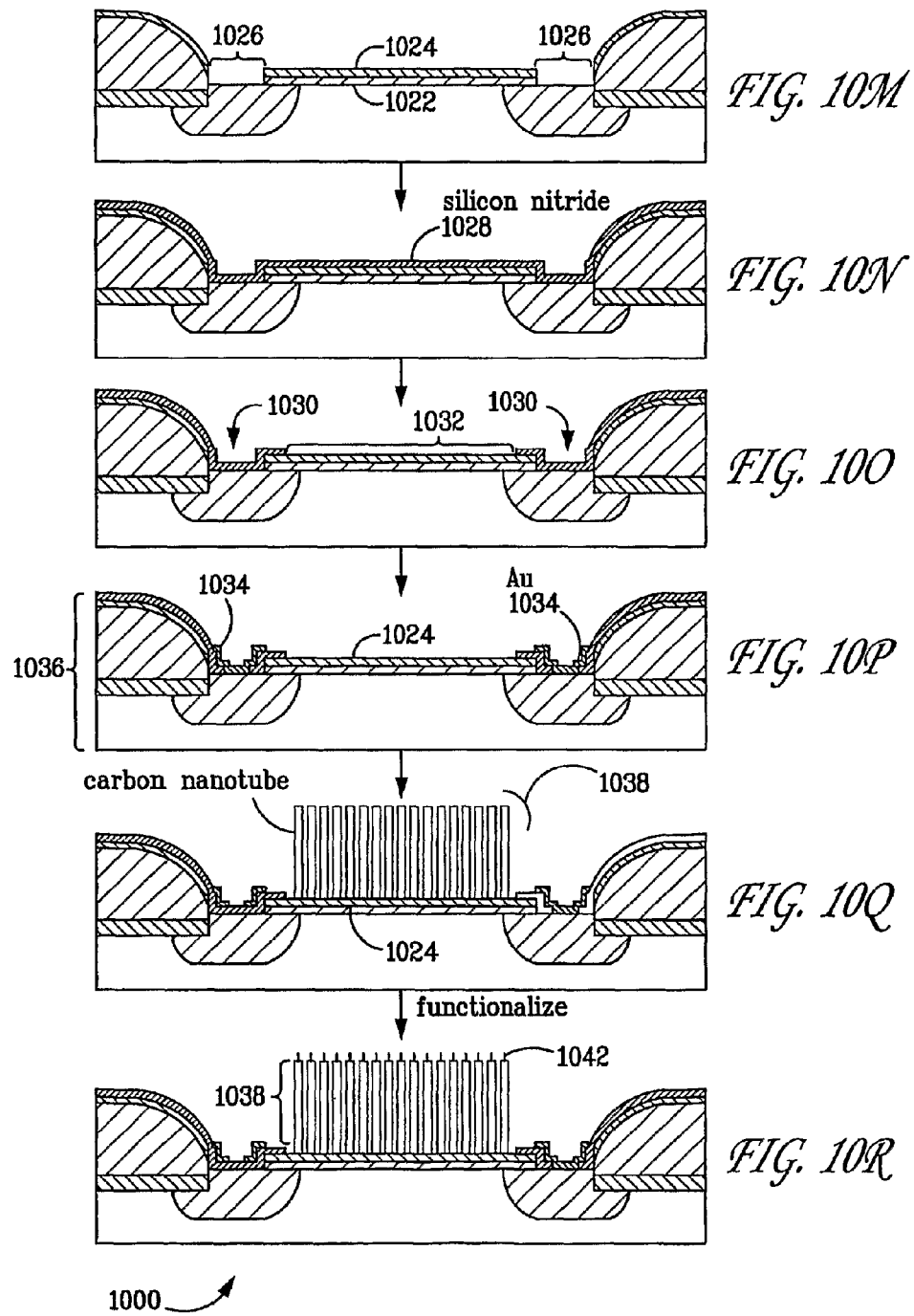

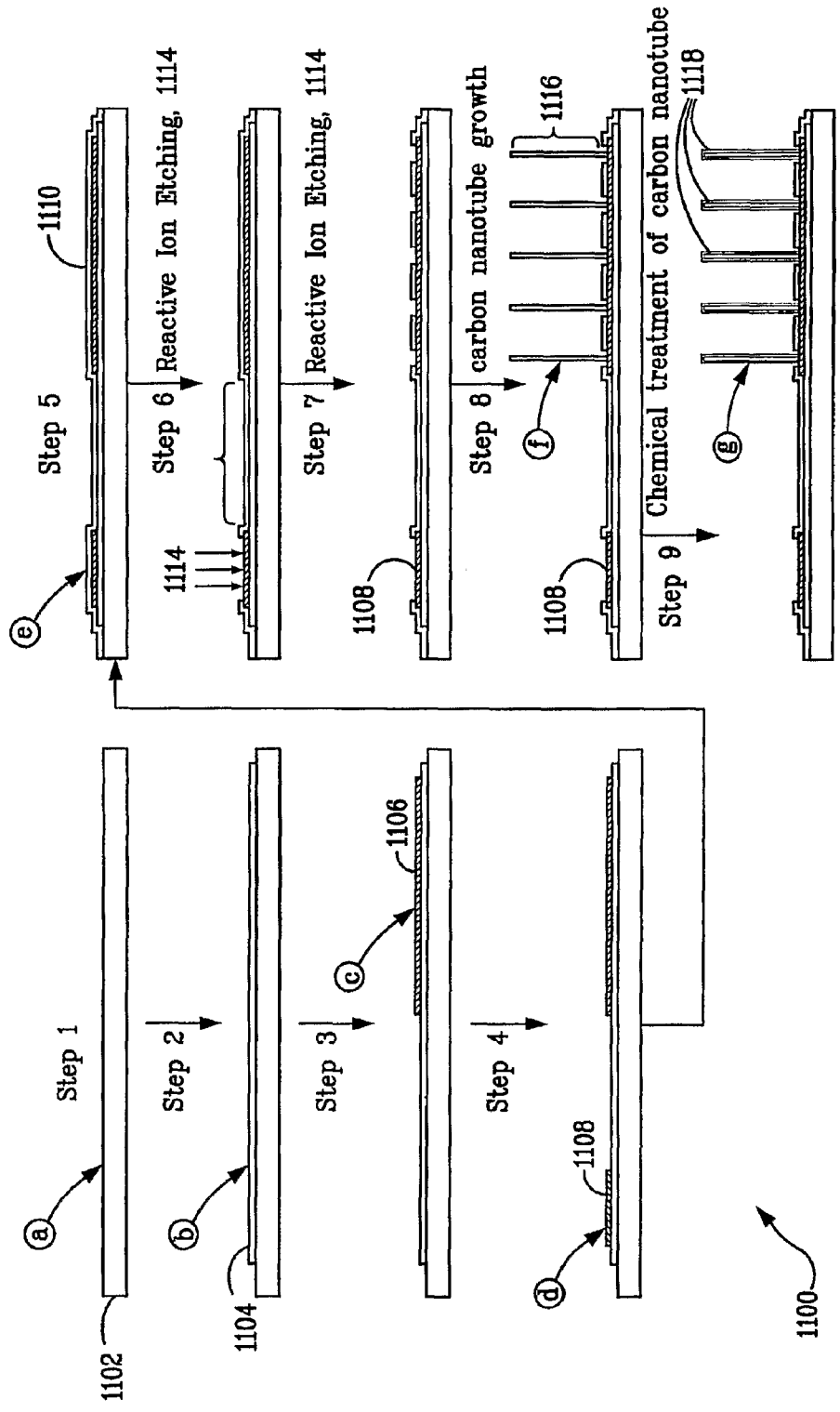

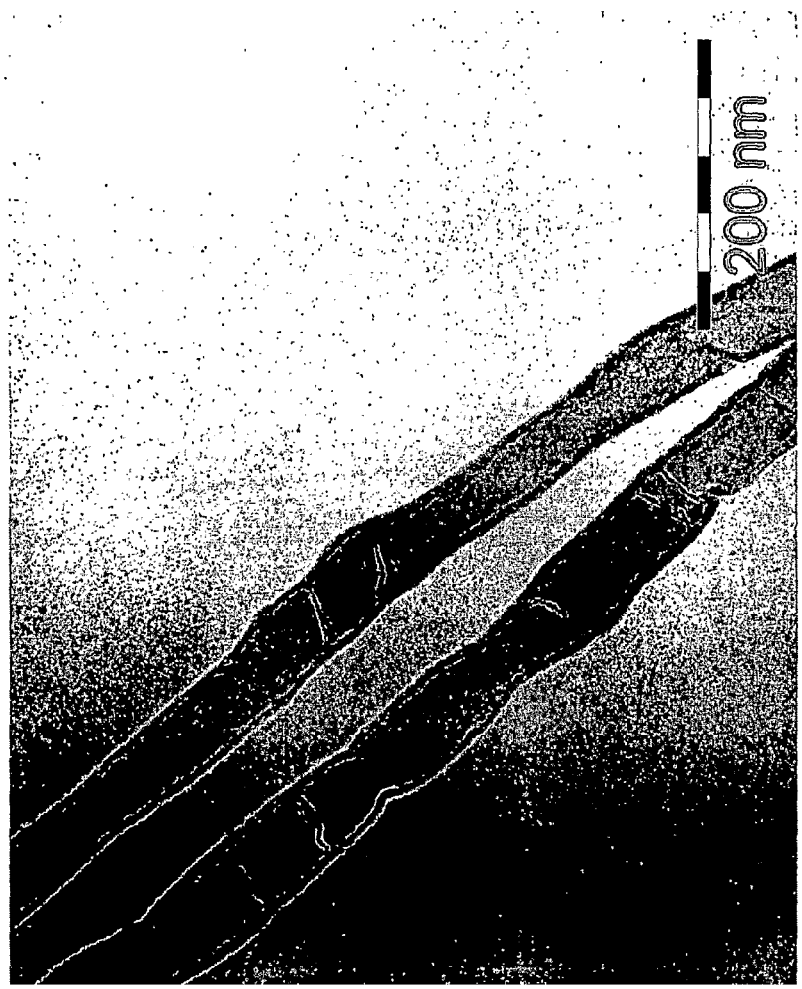

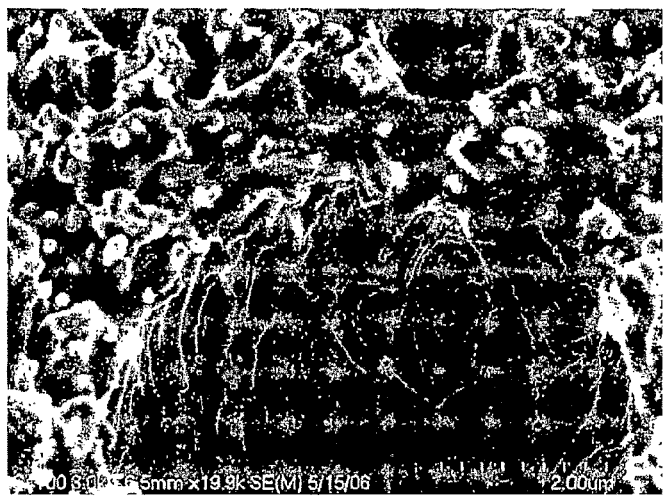
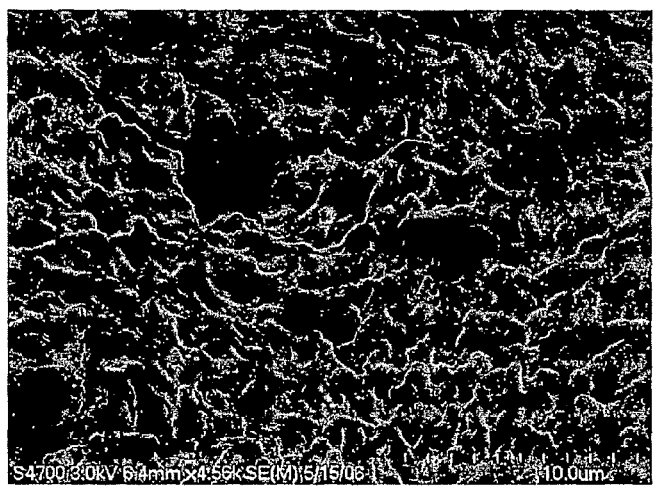
FIG. 20D

CNT-BASED SENSORS: DEVICES, PROCESSES AND USES THEREOF

CROSS-REFERENCE TO RELATED APPLICATIONS

This application is the National Stage of International Application No. PCT/US2007/002104, filed Jan. 26, 2007, which claims the benefit of U.S. Provisional Application No. 60/762,788, filed Jan. 26, 2006, the disclosure of which is incorporated herein by reference in its entirety.

FIELD OF THE INVENTION

The present invention is in the field of chemical and biological sensors. The present invention is also in the field of processes for making chemical and biological sensors. The present invention is also in the field of using sensors for monitoring water quality.

BACKGROUND OF THE INVENTION

Chemical and biological sensors that are used for continuous monitoring generally require a degree of inertness from the sample environment. Inertness is particularly important in utility type applications such as water monitoring. Continually operating sensors in the field need to be rugged, chemically stable and readily manufactured. There is a continuing need to prepare and design sensors that can effectively and efficiently measure a wide range of chemical and biological contaminants in drinking water in view of both public health and national safety perspectives.

The low salt content (high electrical impedance) of drinking water presents a unique challenge to electrochemical measurement because small variations in electrolyte content will introduce significant measurement error. Improvements in the ability to measure variable conductivity water samples from drinking water to sea water without analytical performance degradation are presently needed. Even gold or gold-coated electrodes are known to degrade in such environments. Accordingly, improvements in electrodes and sensors are required.

U.S. Pat. No. 6,905,655 to Gabriel et al. discloses sensors that operate on the principle that the electrical conductivity of a MWNT changes depending on the environment surrounding nanotube. The disclosed sensors, however, require one to carefully lay down MWNTs ("CNTs") parallel to the surface of a substrate. Nanotubes oriented in such a fashion are required to make electrical contact with two or more electrodes on the substrate through the outer surface of its graphene sheet. Such sensors typically require that the nanotubes are bonded with some type of protective coating, such as a polymer, where the nanotubes contact the electrodes. In view of the difficulty of adhering nanotubes lying across electrodes in this fashion, there remains the need to provide CNT-based sensors that overcome these difficulties.

Li et al., *Nano Letters*, 2003, Vol. 3, No. 5, 597-602, discloses a carbon nanotube electrode array for ultrasensitive DNA detection. The nanoelectrode array is based on multi-walled carbon nanotubes embedded in SiO2, with only the open ends of the multiwalled carbon nanotubes being exposed to the environment to give rise to DNA detection. Accordingly, only a very low surface area is provided in the carbon nanotube electrode arrays provided by Li et al. Further improvements are needed to enhance the sensitivity of carbon nanotube electrodes and sensors.

SUMMARY OF THE INVENTION

In certain aspects, the present invention provides sensors composed of one or more multiwall MWNT ("MWNT") array electrodes that are rugged in use, chemically stable and readily manufactured. The MWNT array electrodes used in aspects of the invention can be used to measure drinking water compositions. Various sensor embodiments as described herein can be adapted to many other applications, for example, in medical testing of biological fluids, as well as in testing the safety of pharmaceuticals, beverages and food.

In one aspect, the present invention provides antennae assembly electrodes, comprising: an electrically conductive layer at least partially surmounting a substrate; and an assembly of doped antennae vertically oriented with respect to the electrically conductive layer, wherein each of the doped antennae comprises a doped MWNT comprising: a base end attached to the electrically conductive layer, a mid-section comprising an outer surface surrounding a lumen, wherein at least a portion of the outer surface of the mid-section is capable of being in fluidic contact with an environment in contact with the antennae; a top end disposed opposite to the base end, and a dopant attached to or contained within the lumen, a dopant attached to or contained within the outer surface, a dopant attached to or contained within the top end, or any combination thereof. Sensors and field-effect transistors comprising these antennae assembly electrodes are also provided.

The present invention also provides methods of making an antennae assembly electrode, comprising the steps of: surmounting a substrate with an electrically conductive layer; surmounting an assembly of antennae on the electrically conductive layer giving rise to the antennae being vertically oriented with respect to the electrically conductive layer, wherein each of the antennae comprises a MWNT comprising a base end being attached to the electrically conductive layer; a mid-section comprising an outer surface surrounding a lumen, wherein at least a portion of the outer surface of the mid-section is capable of being in fluidic contact with an environment in contact with the antennae; and a top end being disposed opposite to the base end; and doping at least a portion of the MWNT with a cladding, a covalent bond linkage, a functional dopant molecule, a fill material, or any combination thereof. Doped antennae assembly electrodes, sensors and field-effect transistors are also provided using these methods.

In other aspects, the present invention provides antennae assembly field-effect transistors, comprising: a substrate comprising a source and a drain; a gate oxide layer at least partially surmounting the substrate, source and drain; an electrically conductive layer at least partially surmounting the gate oxide layer; and an assembly of doped MWNT antennae vertically oriented with respect to the electrically conductive layer.

The present invention also provides sensors, comprising: at least two electrodes situated on a substrate, wherein at least one of the electrodes comprises an antennae assembly electrode, wherein the antennae assembly electrode comprises an electrically conductive layer at least partially surmounting a substrate; and an assembly of doped antennae vertically oriented with respect to the electrically conductive layer, wherein each of the doped antennae comprises a doped MWNT comprising: a base end attached to the electrically conductive layer, a mid-section comprising an outer surface surrounding a lumen, wherein at least a portion of the outer surface of the mid-section is capable of being in fluidic contact with an environment in contact with the antennae; a top end disposed opposite to the base end, and a dopant attached to or contained within the lumen, a dopant attached to or contained within the outer surface, a dopant attached to or contained with the top end, or any combination thereof.

In other aspects, the present invention provides antennae assembly electrodes, comprising: an electrically conductive layer at least partially surmounting a substrate; and an assembly of antennae vertically oriented with respect to the electrically conductive layer, wherein each of the antennae comprises a MWNT comprising: a base end attached to the electrically conductive layer, a mid-section comprising an outer surface surrounding a lumen, wherein at least a portion of the outer surface of the mid-section is capable of being in fluidic contact with an environment in contact with the antennae; and a top end disposed opposite to the base end. Sensors and field-effect transistors are also provided using these electrodes.

The present invention also provides methods of making an antennae assembly electrode, comprising the steps of surmounting a substrate with an electrically conductive layer; and surmounting an assembly of antennae on the electrically conductive layer giving rise to the antennae being vertically oriented with respect to the electrically conductive layer, wherein each of the antennae comprises a MWNT comprising a base end being attached to the electrically conductive layer; a mid-section comprising an outer surface surrounding a lumen; and a top end being disposed opposite to the base end.

The present invention also provides methods of growing non-aligned MWNTs on a substrate, comprising: depositing a nickel metal catalyst on a substrate; and contacting the nickel metal catalyst with a gas mixture comprising a carrier gas and a carbon source gas at a temperature in the range of from about 650° C. to about 750° C., the carbon source gas comprising acetylene, wherein the substrate comprises silicon, silicon dioxide, silicon nitride, phosphorus doped poly silicon, or boron doped P-type silicon, to give rise to non-aligned MWNTs attached to the nickel metal catalyst.

The present invention also provides methods of growing aligned MWNTs on a substrate, comprising: contacting a substrate with a gas comprising a carrier gas and a carbon source gas at a temperature in the range of from about 800° C. to about 960° C., the carbon source gas comprising iron (II) phthalocyanine, wherein the substrate comprises silicon, silicon dioxide, silicon nitride, phosphorus doped poly silicon, or boron doped P-type silicon, to give rise to aligned MWNTs attached to the substrate.

The present invention also provides methods of growing aligned MWNTs on a substrate, comprising: depositing a nickel metal catalyst on the titanium barrier layer; and contacting the nickel metal catalyst with a gas mixture comprising a carrier gas and a carbon source gas at a temperature in the range of from about 650° C. to about 750° C., the carrier gas comprising argon, ammonia and hydrogen, the carbon source gas comprising acetylene, wherein the substrate comprises silicon, silicon dioxide, silicon nitride, phosphorus doped poly silicon, or boron doped P-type silicon, to give rise to aligned MWNTs attached to the nickel metal catalyst.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 2A is a top-view perspective schematic illustration of an embodiment of a CNT array FET, which is suitable for ion sensing, of the present invention;

FIG. 2B is a side-view schematic illustration of the CNT array FET of FIG. 2A;

FIG. 6 provides illustrations of representative polymers that can be used as cladding and peapod materials for CNTs.

FIG. 7 provides illustrations of representative donor-acceptor polymer chemistries for CNT dopants;

FIG. 11 provides a schematic illustration of an embodiment of the method of the present invention for making a CNT island array electrode;

FIG. 14L shows ACNTs grown on Patterned Chip with growth conditions; Ar/$H_2$/Temp/FePc/Time:20/20/902/0.4/20 min. And post-clean up process carried out to remove the sacrificial Copper layer.

FIG. 16K shows a TEM image of multiwalled CNTs grown on P-type Si with growth conditions; Ar/H$_2$/Temp/FePc/Time:80/75/960/0.6/5 min.

FIG. 18H 0.05 M tetra butyl ammonium hexafluoro phosphate supporting electrolyte in methylene chloride solvent. Scan rate 20 mV/s. ACNT film electrochemical analyses after SFT treatment.

FIG. 18J 0.05 M tetra butyl ammonium hexafluoro phosphate supporting electrolyte in methylene chloride solvent, Scan rate 20 mV/s. ACNT film electrochemical analysis after condition 2 treatment.

FIG. 20D SEM images of the prepolymerized CNT film (Chip # SP-169). a) Cross sectional view of the conducting polymer-CNT cladding. The side walls of the CNTs are visible and b) Top view of the structure.

DETAILED DESCRIPTION OF ILLUSTRATIVE EMBODIMENTS

Figure 1A:
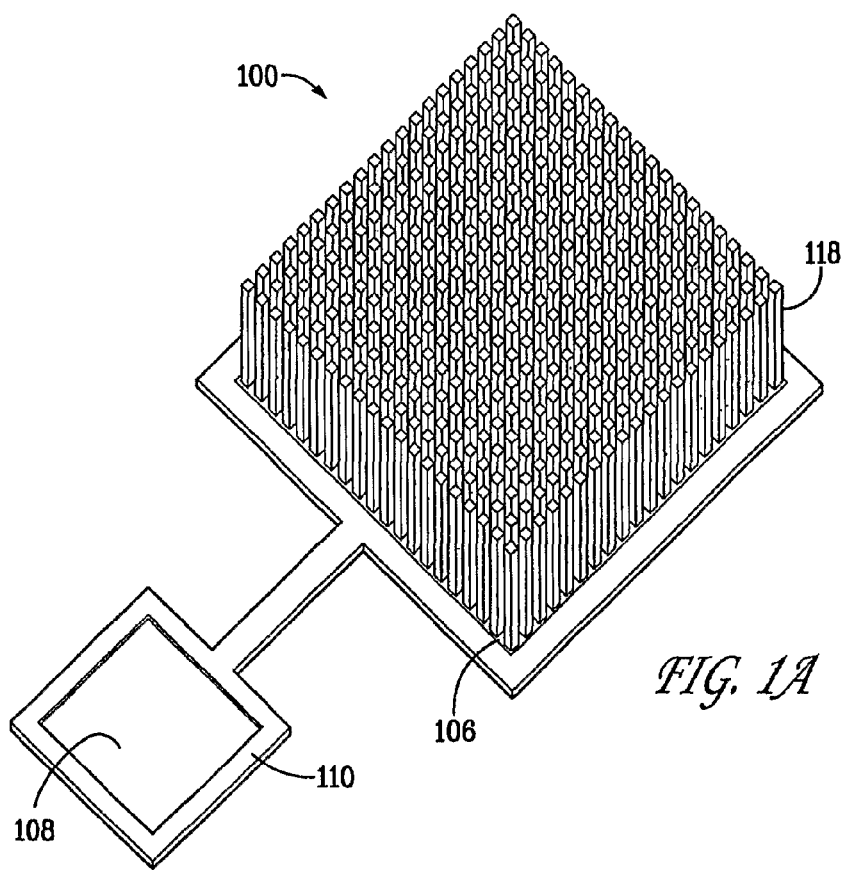
FIG. 1A is a top-view perspective schematic illustration of an embodiment of a CNT array electrode of the present invention.
Figure 1B:
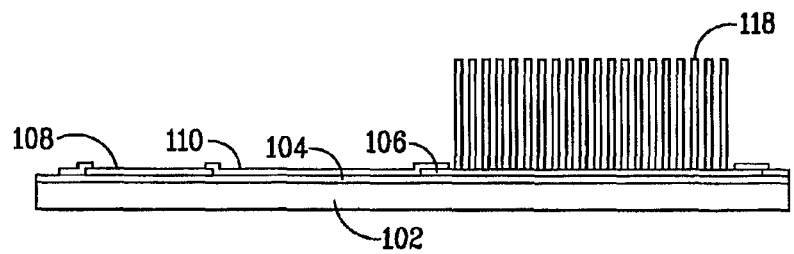
FIG. 1B is a side-view schematic illustration of the CNT array electrode of FIG. 1A.
Figure 3A:
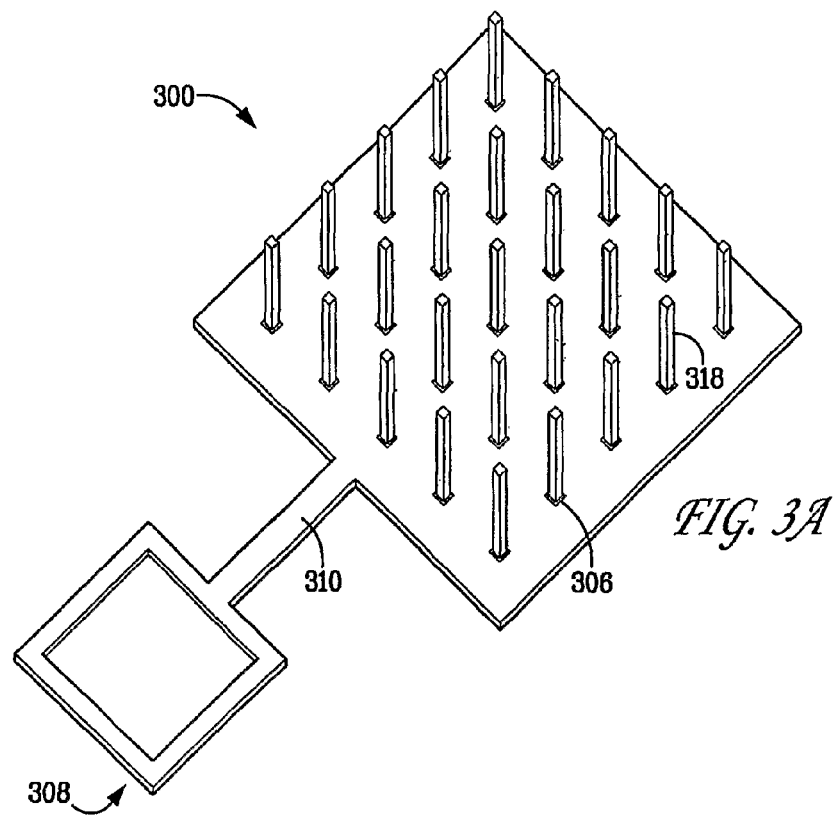
FIG. 3A is a top-view perspective schematic illustration of an embodiment of a CNT island array electrode of the present invention.
Figure 3B:
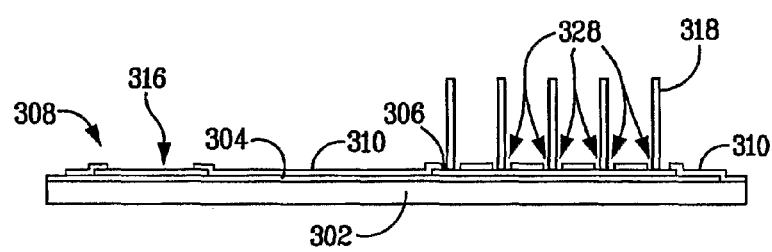
FIG. 3B is a side-view schematic illustration of the CNT island array electrode of FIG. 3A.
Figure 4:
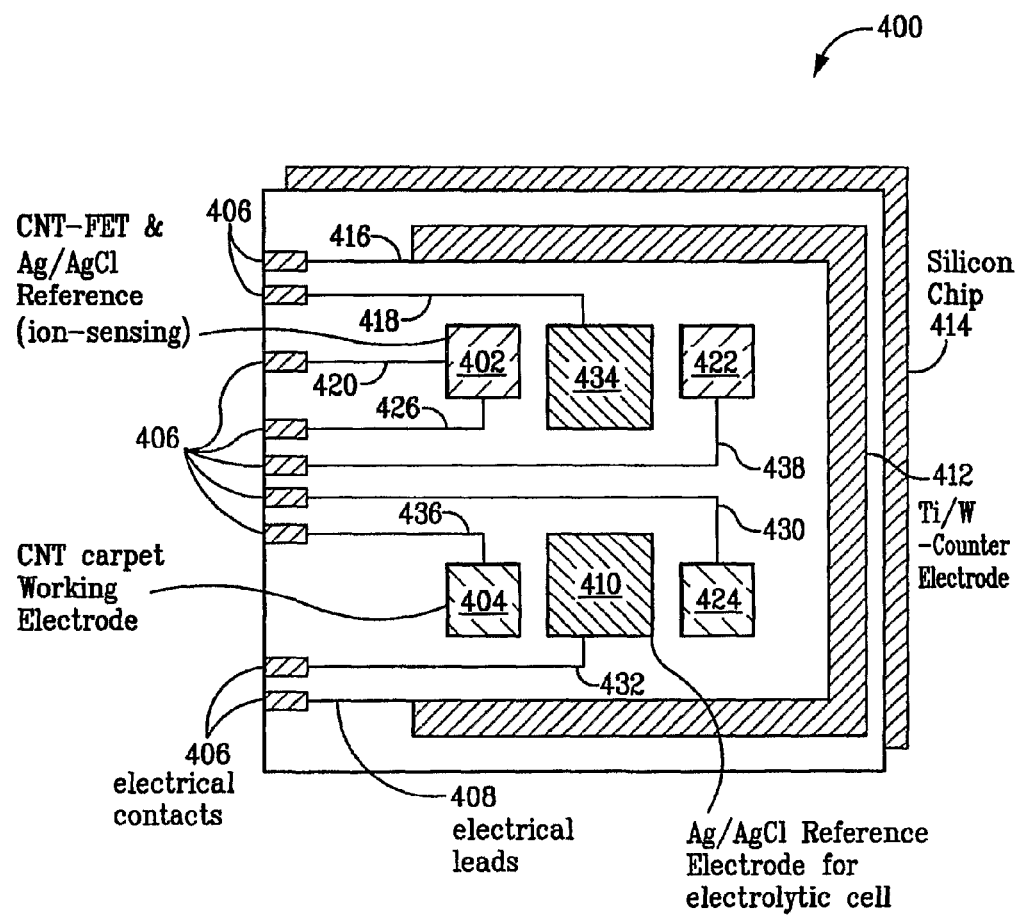
FIG. 4 is a schematic illustration of an embodiment of a multi-sensor CNT array chip of the present invention that includes integrated counter and reference electrode elements.

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

The antennae assembly electrodes include an electrically conductive layer at least partially surmounting a substrate; and an assembly of doped antennae vertically oriented with respect to the electrically conductive layer. Each of the doped antennae comprises a doped MWNT comprising: a base end attached to the electrically conductive layer, a mid-section comprising an outer surface surrounding a lumen, wherein at least a portion of the outer surface of the mid-section is capable of being in fluidic contact with an environment in contact with the antennae. The doped MWNT also has a top end disposed opposite to the base end, and a dopant attached to or contained within the lumen, a dopant attached to or contained within the outer surface, a dopant attached to or contained within the top end, or any combination thereof. Sensors and field-effect transistors can be suitably fashioned using these antennae assembly electrodes, as described further herein.

In certain aspects of the present invention there are provide MWNT based sensors that are composed of electrode arrays comprising aligned MWNTs that can be electrically conductive as well as chemically inert to water and biological media. Suitable sensors are capable of sensing one, and preferably more than one analytes in a test fluid. Such carbon material structures make ideal electrochemical sensors by evoking two properties of electrodes; the chemical inertness of diamond with the electrical conductivity (i.e., electron mobility) of a metal. The chemical inertness relates to the ability to measure an electro-chemical reaction without memory (i.e., retention) of such reaction. The graphene electron conductivity of MWNTs can range from metallic to semi-conducting while the surface chemistry can be controlled by varying the environmental conditions, such as, temperature, pressure, and chemical environment. The unique properties of MWNTs allow for the adaptation to novel detection schemes by manipulating conduction of CNTs and mediating such characteristic by chemical doping.

CNT's may be grown by Chemical Vapor Deposition (CVD) into a template of perpendicularly aligned arrays of CNT electrodes. The CNTs diameter, length and pitch is controlled by the chemical vapor deposition ("CVD") growth process to create a spaced NT electrode array structure that optimizes effective electrolysis surface, yet minimizes Ohmic loss through the sample medium. In certain aspects, the nominally idealized CNT nanoarray structure comprises a 10:1 pitch:diameter ratio at nanometer dimensions. Without being bound by any particular theory of operation, the CNT nanoarray structure of various embodiments of the present invention apparently minimizes analytical measurement errors that are otherwise present in conventional electrode structures and materials.

The readily achievable CNT structural design disclosed herein provides a number of beneficial design attributes that are especially important for monitoring drinking water. The low salt content (high electrical impedance) of drinking water presents a unique challenge to electrochemical measurement because small variation in electrolyte content will introduce significant measurement error. The ability to measure variable conductivity water samples from drinking water to sea water without analytical performance degradation is an important criterion of robust product technology and especially important for continuous monitoring.

The CNT sensors can be used in different modes to selectively detect analytes. In one mode, the CNTs can be used as a source or depository of electrons to be exchanged with the medium in an electrolytic reaction. In a second mode, the CNTs can be used to function as a static electric field measurement in the potentiometric mode (i.e, zero current flow.) In some embodiments, CNT sensors can be used in continuous electrolytic monitoring of strong oxidants (such as chlorine) in drinking water.

Without being bound to a particular theory of operation, the CNT sensors are particularly well-suited for use in strong oxidants because of the high chemical resistance of CNTs. In electrochemical terms, the CNTs surface chemistry is essentially unaffected by chlorine in the presence or absence of electrolysis. This is characteristically unlike noble metal electrodes (e.g., Pt or Au) in which the surface can indeed be oxidized or electrolytically altered. This property allows for a broad operating voltage window for measuring electro-active molecules in water using various embodiments of the CNT-based sensors of the present invention. CNT working electrodes operating in the electrolytic measurement mode do not necessarily require coatings or dopants to effect selective measurement. In one embodiment, specificity and sensitivity of redox response is essentially enhanced by voltage (i.e., bias) programming techniques. Molecules with redox potentials that fall outside the operating voltage window can be mediated by dopants to shift the energy (i.e., voltage) to within the operating voltage window. Programming techniques are provided in U.S. Pat. No. 5,120,421 to Glass et al., "Electrochemical sensor/detector system and method", the portion of which pertaining to programming is incorporated by reference herein.

In the potentiometric mode, the CNTs can measure static electric fields generated by ion charge accumulation. In these embodiments, the CNTs can be doped with selective ligand molecules that selectively bind ions. Such a CNT ion sensor can be employed to detect calcium ion content in drinking water as a measure of water hardness. In this mode, and without being bound by any particular theory of operation, the electrical conductivity of CNTs tends to be irrelevant to the measurement and the CNT appears to function as a conduit for the measure of static charge. In this mode, the dopant chemistry evokes selective chemical response which appears to be manifested as a chemical potential or voltage sensed by the CNT.

Doping of CNTs can be accomplished in several ways, i.e., by; "peapod" formation (e.g., nanotubes containing other atoms, molecules, or both residing within the interior of the nanotube), polymer film coatings/claddings of CNTs, and by chemical linkage to the graphene carbon of the CNT and/or linkage to the cladding. Further details on forming CNT peapods can be found in U.S. Pat. No. 6,863,857, "Hybrid materials and methods for producing the same" to Luzzi and Smith, the portion of which pertaining to the formation of filled CNTs is incorporated by reference herein. A doping embodiment can be characterized by a peapod structure created by one or more active reagents (or dopants) to a CNT lumen and annealing the CNT to encapsulate the active reagents or dopants. Without being bound by any particular theory of operation, this provides a cocoon-like CNT protection of active reagent or dopant while providing electron exchange (i.e., tunneling) between the interior dopant and the outside medium. The graphene carbons of the CNTs are believed to function as a conduit for electron transfer between the oxidation state of the sample molecule and the measurement circuit. The peapod electrolysis current is a measure of the rate of electron transfer incurred by the sample and mediated by dopant. In embodiments when the dopant is an ionophore, ion charge accumulation on the CNT can be manifested as a voltage that is related thermodynamically to the electrolyte solution chemical potential. Large binding constants of ion-ligand complex formation favors the partitioning of charge to the interior of the filled MWNT and the electric field generated is in equilibrium with sample ion content.

Another way to dope the MWNTs is to use electrospray ionization, which can selectively deposit dopants in, or on, particular MWNTs on the electrode. Details of selective doping of particular nanotubes on antennae assembly electrodes using electrospray are provided in U.S. Provisional Patent Application Ser. No. 60/762,613, "Electrospray Deposition: Devices and Methods Thereof", by Salvatore Pace and Francis Man, filed Jan. 26, 2006, the entirety of which is incorporated by reference herein.

In certain embodiments, doped polymeric claddings that coat the CNT (i.e., graphene) backbone may be formed by free radical polymerization from organic monomers. Free radical polymerization may be mediated by a number of methods know in the art, including RF plasma reaction (i.e., in the gas phase), by electrolytic polymerization (i.e., in the liquid phase), or any combination thereof. One scheme for polymer impregation is accomplished by trapping dopant coincident with the polymerization in a co-deposition process. Alternatively, a polymer CNT cladding can be impregnated by phase transfer partitioning, for example, by using supercritical fluid carbon dioxide ("scCO$_2$") as a partitioning solvent. Stable CNT interfacial boundaries can be created using a selective reagent that chemically links to the CNT backbone as a precursor step to polymer coating (i.e., cladding). In one embodiment, combining a peapod structure with an exterior CNT coating gives rise to unique reagent interactions depicted by the interplay of sample modulated electrochemiluminescent (ECL) emission (e.g., Example #6). An ammonia sensor (e.g., Example #3) is another example of the interplay between the gas barrier PTFE cladding and a non-actin-doped peapod CNT.

The present invention relates to the design and methods of fabrication of MWNT chemical and biological sensors and their use thereof. MWNTs can be chemically doped with reagents to respond electro-chemically and/or photo-chemically to specifically targeted molecules in water samples and biological media. Devices and methods of detection are also provided that measure the transduction of chemical to electrical or chemical to photonic signals. These signal can be electronically processed to yield high sensitivity and specificity responses to a variety of analytically targeted molecules.

In one mode, the subject invention includes a plurality of CNT sensing elements patterned on a silicon chip. Each CNT sensing element comprises a plurality of substantially aligned MWNTs grown perpendicularly to the plane of the substrate (Si) and subject to contact or exposure to test sample fluid. Additional circuit elements may also be mounted on the substrate (e.g., a silicon chi, such as electrical conduits, termination points and amplifiers, photon sources, and other components. CNT growth can be generated by chemical vapor deposition (CVD) and the geometric patterns defined by the electron beam lithography of the metal catalyst. The CVD grown CNT array patterns can be perpendicularly aligned and in electrical contact with the metal. In one embodiment, a suitable CNT sensing element includes a silicon chip comprising a combination of electrochemical sensing elements based on redox electrolysis and charge coupled ion transduction. A combination of these elements comprise a multisensor chemical profiling chip. An example of a nominal drinking water test combination of free and total chlorine and water hardness would deploy the following sensors: CNT-gated FET for calcium, a CNT Working electrode for free chlorine and a doped/cladded CNT peapod working electrode-photodiode combination for tot-Cl$_2$ modulated electrochemiluminescence.

CNT sensor elements can be fabricated with processes known to those of skill in the art of semiconductor materials and processing. Each CNT sensor element can be doped with selective reagent to impart chemical detection specificity. In one embodiment, for example, an ensemble of CNT sensor elements can be operated in concert to effect the chemical profiling of drinking water. In other embodiments, undoped CNTs can be voltage programmed to elicit selective responses for electro-active molecules such as chlorine and chloramines. Redox mediators such as Ru(bpy) can be electrolytically activated to generate photon emission that can also be modulated by sample interaction. In the potentiometric mode (charge coupling), CNTs can be doped with ionophores that selectively react with sample target ions. A combination of CNT sensor elements can therefore be selected to detect for a drinking water "disinfection profile" as outlined in Table I. The CNT sensor elements of the present invention provide a broad electrolysis operating window for water samples and also virtually eliminate artifacts such as ion transport partitioning and non-specific ion exchange at sample/membrane interfaces that diminish the ion detection (sensitivity) limit of conventional ion selective electrode (ISE) sensors.

Redox Detection-Electrolytic sensing: In another mode, a CNT sensor element is provided that can be operated in an electrolytic measurement mode. In this mode, the CNT sensor element does not chemically participate in the electrolysis, rather it functions as an inert working electrode surface to conduct electrolysis of electro-active molecules. This property allows the CNTs to measure electrolytic currents with little or no inter-sample surface memory effects that would otherwise compromise precision and accuracy. Doped mediators can also be suitably used to facilitate the electron transfer at the CNT to enhance the kinetics of electron transfer, to lower the energy (voltage) required for the measurement, or both. Mediated electron transfer suitably allows for electrolytic measurement in a useful voltage region.

Suitable redox mediators can be electrolytically activated to excited states resulting in photon emission as they dismutate to the ground state. Such transitions can be electrochemically initiated at the CNT working electrode and modulated by suitable redox active sample target molecules. In certain embodiments, analytes such as mono-chloroamine can be chemically oxidized by Ru(bipy)2+ dopant to Ru(bipy)3+ while Ru(bipy)3+ can be electrolytically reduced to the Ru(bipy)2+. The interaction between the Ru oxidized species within the cladding and the peapod (e.g., the reduced species) generates photon emission at 610 nm which is, in turn, modulated by the sample. Without being bound by any particular theory of operation, electrolysis at the CNT surface triggers the electro-chemiluminescence ("ECL") although the modulation is chemically induced by a sample oxidant, such as chloramines. Hence, for drinking water samples, the emission intensity can be used to measure total chlorine.

Ion & Gas Detection-Potentiometric Sensing: The potentiometric (ISE) sensor (voltage measurement at zero current) can measure CNT charge accumulation (i.e., electric field), as a consequence of ionic charge buildup on the CNTs. The CNTs can be doped with suitable ionophores (e.g., cyclic polyethers) to induce a selective ion response of a test water sample. Various suitable ionophores can be used as described herein. Without being bound by any particular theory of operation, the ionophores function as a specific binding agent for the ion. Accordingly, the accumulation of charge on the CNT can be measured with an electrometer amplifier circuit. The CNTs function as a nanofield of antennas that receive the modulating ion charge that, in turn, measures a chemical potential (i.e., voltage).

The CNT sensor elements can be electronically passive (i.e., no amplifier). In other modes, the ISE structure can combine one or more CNT sensor elements with an active circuit such as a field effect transistor (FET). For example, the CNT's can be CVD grown and patterned directly on a gate surface of a suitable FET. Suitable FETs can have a gate that is ion specifically modulated by the sample solution/ionophore interaction. The modulated ion response (or chemical potential) is tuned by the ionophore CNT-dopant chemistry. In a further embodiment, integrating amplifiers to sensors on a substrate chip can be used to improve signal/noise characteristic signal performance Multi-Sensor CNT Array: A multi-sensor CNT array can be patterned on a silicon substrate and subsequently doped with a plurality of selective reagent to evoke specific response to a plurality of sample target molecules. Each CNT feature can be modified to detect a single chemical species in a sample, such as drinking water. A portion of the sensing elements of the multi-sensor CNT array can comprise unmodified CNTs to measure electrolysis currents at appropriate bias voltages corresponding to the electro-active species. In this embodiment, select voltage programs can be used to measure test species. Other sensing elements can be doped (chemically altered) with ionophoric or redox mediating species to measure surface potentials based on accumulated ion charge or redox ratio of electro-active molecules.

Among the various sensor embodiments described herein, the CNTs can be in contact with a catalytic metal surface that is patterned on a silicon substrate which is provided as an integral circuit component of an electrode ensemble. This ensemble comprises an array of sensors deployed to contiguously and selectively measure a plurality of test analytes. In certain embodiments, the device also includes one or more counter and reference electrode elements that are integrated onto the chip structure. Such electrode elements can be strategically positioned on the sensor to provide electrochemical support function but do not necessarily partake in the selective sensing/response process.

EXAMPLES AND OTHER ILLUSTRATIVE EMBODIMENTS AND DESCRIPTION

Silicon Chip Design and Process Schemes for Aligned CNT Patterns
I. CNT Array Working Electrode Pattern, FIG. [1], CNT Array Working Electrode Structure for Electrolytic Cell Configuration.

Process Description. Referring to the sequence of process steps in FIG. 9, the process starts with a 100 mm silicon wafer substrate (902) with a 500 nm thermal oxide layer (904) on top (steps 1 and 2). The patterning of TiW/Mo/TiW electrically conductive layer (906) is performed in a two-step lithography process. In the first step, a liftoff resist is spin coated, and baked. In the second step, a conventional photo-resist is spin coated, exposed, and developed. During resist development, the developer not only removes the exposed photo-resist, it also removes and undercuts the liftoff resist such that when the wafer is immersed in acetone, the subsequent metal stack is lift off leaving a clean metal definition. Then a stack layer of TiW/Mo/TiW: 40 nm/40 nm/40 nm (b) is sputtered, followed by a reactive sputtering of 15 nm TiN (b). The metal stack (step 3) is then liftoff by immersing in acetone. Afterwards, a conventional liftoff process is performed where photo-resist is patterned to define the gold metal contact pad (908) with a Cr adhesion layer, followed by evaporation of a 50 nm of gold, and immersion in acetone liftoff solution (step 4). Similarly, the 7 nm nickel catalyst layer (d) is patterned by liftoff process using the liftoff resist to produce a sharp nickel metal interface. Next, a 500 nm layer of PECVD silicon nitride protective layer (910) is deposited at 38° C. (step 5). Contact holes (912) are patterned and etched in reactive ion etching (914) (step 6). After that, the wafer is ready for MWNT (916) growth where substrate (902) is exposed to acetylene and ammonia gas at 400° C. (step 7), followed by further chemical functionalization (918) (step 8) to give rise to a doped CNT array working electrode (900).

Figure 10G:
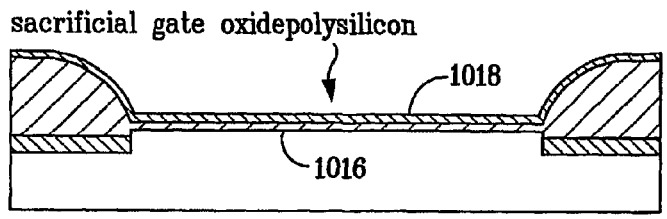
FIGS. 10a-10r provides a schematic illustration of an embodiment of the method of the present invention for making a CNT array FET.
Figure 10H:
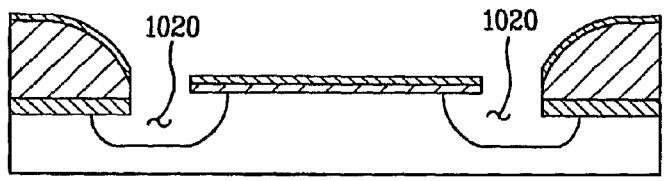
Figure 10I:
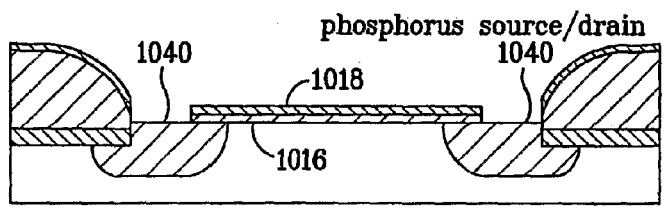
Figure 10J:
Figure 10K:
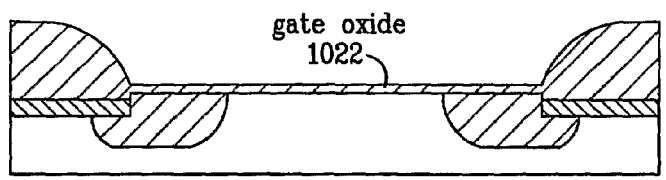
Figure 10L:
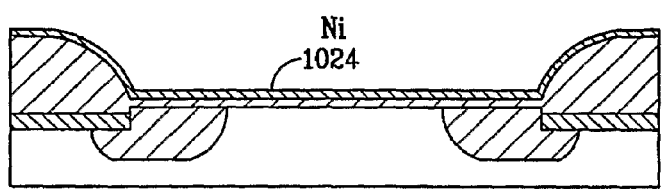

Process Flow
Starting Wafer
    p-type boron doped 100 mm silicon wafer, single side polished
Thermal oxide Deposition
    500 nm thermal oxide at 1000 C. for 30 mins
Lithography 1—Interconnect
    Spin LOR-5a 40 H rpm for 10 sec
    Softbake on hot plate for 5 mins at 180 C.
    Spin 220 4 k rpm for 10 sec
    Softbake on hot plate for 90 s at 115 C.
    Expose 5 sec at 25.0 mW/cm2
    Post-exposure bake on hot plate for 90 s at 115 C.
    Develop in MIF 300 for 2 mins
    Rinse 2 mins in DI, spin dry
TiW/Mo/TiW/TiN Interconnect Deposition
    Sputter 40:40:40 nm of TiW/Mo/TiW onto wafer
    Sputter 15 nm of Ti under nitrogen environment
    Liftoff in acetone
    Rinse 2 mins DI, spin dry Lithography 2—Contact Pad
  Spin HMDS 4 k rpm for 30 s
  Spin 220 4 k rpm for 10 sec
  Softbake on hot plate for 90 s at 115 C
  Expose 5 sec at 25.0 mW/cm2
  Post-exposure bake on hot plate for 90 s at 115 C
  Develop in MIF 300 for 2 mins
  Rinse 2 mins in DI, spin dry
Gold Metal Pad Deposition
  Evaporate 10:100 nm of Cr/Au onto wafer
  Liftoff in acetone
  Rinse 2 mins DI, spin dry
Lithography 3—Catalyst Deposition
  Spin LOR-5a 40 H rpm for 10 sec
  Softbake on hot plate for 5 mins at 180 C.
  Spin 220 4 k rpm for 10 sec
  Softbake on hot plate for 90 s at 115 C
  Expose 5 sec at 25.0 mW/cm2
  Post-exposure bake on hot plate for 90 s at 115 C
  Develop in MIF 300 for 2 mins
  Rinse 2 mins in DI, spin dry
Nickel Catalyst Deposition
  Evaporate 7 nm of nickel onto wafer Liftoff in acetone
  Rinse 2 mins DI, spin dry
Passivation nitride Deposition
PECVD deposit 500 nm of silicon nitride at 380 C.
Lithography 4—Contact Opening
  Spin HMDS 4 k rpm for 30 s
  Spin 220 4 k rpm for 10 sec
  Softbake on hot plate for 90 s at 115 C
  Expose 5 sec at 25.0 mW/cm2
  Post-exposure bake on hot plate for 90 s at 115 C
  Develop in MIF 300 for 2 mins
  Rinse 2 mins in DI, spin dry
Passivation nitride etch
  Plasma etch, P=100 W, P=100 mT, CF4=40 sccm, O2=1 sccm
  MWNT Grow (by the PECVD-Acetylene method or the thermal CVD growth method; A. gas phase, B. solid precursor)
  PECVD Acetylene: ammonia=54 sccm:200 sccm, P=5 mBar, T=675 C. or Thermal CNT growth (as outlined below)
II. CNT-Gated MOSFET Pattern; FIG. [2]; CNT-Gated MOSFET Structure for Ion Detection Process Description. Referring to the sequence of process steps in FIGS. 10a-10r, the starting material is a p-type silicon wafer (1002) with a 40 nm thick pad dioxide (1004) (FIG. 10a). A 200 nm thick LPCVD silicon nitride (1006) is then deposited at 820 C. (FIG. 10b). The nitride and pad oxide layer are patterned by conventional photo-resist, and etched in reactive ion etching followed by a 250 nm silicon recess etch (1008) (FIG. 10c). A dose of 5e13/cm2 boron (1010) is implanted at 60 kev to form the field implantation (FIG. 10d). After that, a 700 nm thick silicon dioxide (1014) is grown in the field area (1012) (FIG. 10e). Next, the nitride and pad oxide (1004, 1006) are stripped off by immersing into hot phosphoric acid and buffered hydrofluoric acid (FIG. 10f). A sacrificial gate oxide (1016) is grown at 1000 C., followed by a polysilicon (1018) deposition at 625 C (FIG. 10g). A conventional photo-resist is applied to define the source and drain areas (1020) of the transistor. Next, exposed polysilicon layer is etched using reactive ion etching and sacrificial gate oxide is wet etched (FIG. 10h). After that, a dose of phosphorus ion (1040) is implanted, followed by a drive-in (FIG. 10i). Subsequently, the polysilicon (1018) and oxide layer (1016) are sacrificially removed (FIG. 10j). Then another gate oxide (1022) is grown (FIG. 10k) and a 30 nm catalyst nickel layer (1024) is sputtered (FIG. 10l). Conventional photoresist is then used to define the source and claim (1026) of each gate (1022) of the transistor where nickel (1024) and gate oxide (1022) is etched (FIG. 10m). A thin 200 nm of plasma-enhanced chemical vapor deposition (PECVD) silicon nitride is then deposited at 380 C. to form the passivation layer (1028) (FIG. 10n). The nitride is subsequently patterned and etched to define the contact holes (1030) to the source and drain (1026) and to reveal the CNT growth area (1032) (FIG. 10o). Photoresist (not shown) is next patterned and a 100 nm thick gold is then evaporated, and subsequently lift off to form metal contact (1034) (FIG. 10p). The wafer (1036) is then exposed to acetylene and ammonia gas at 400 C. (FIG. 10q) in a PECVD chamber where vertically aligned MWNTs (1038) are grown on the exposed nickel (1024). After that, the nanotubes are ready for chemical functionalization (doping) (FIG. 10r) with a dopant (1042).

Process Flow
  Starting Wafer
    p-type boron doped 1.2 ohm-cm, 100 mm silicon wafer <100>, single side polished
  Grow Pad Oxide
    Standard Prefurance cleaning—rinse to 15.2 M ohm-cm
    Grow 40 nm of silicon dioxide: $T_{dep}$=22 min, dry $O_2$, 1000 C, 40 nm thick
    Anneal 10 min in $N_2$
  LPCVD Nitride Deposition
    Deposit 200 nm of LPCVD nitride: 820 C, Tdep=40 min
  Lithography 1: Active Area
    Spin HMDS 4 k rpm for 30 s
    Spin 220 4 k rpm for 10 sec
    Softbake on hot plate for 90 s at 115 C
    Expose 5 sec at 25.0 mW/cm2
    Post-exposure bake on hot plate for 90 s at 115 C
    Develop in MIF 300 for 2 mins
    Rinse 2 mins in DI, spin dry
  Nitride Etch
    Descum: $O_2$, 20 W, 300 mT, 1 min
    Reactive Ion Etch: $CF_4$:20 sccm, $O_2$:1 sccm 100 mTorr, 100 W, 34 min
  Pad Oxide Etch
    Reactive Ion Etch: $CHF_3$=25 sccm, $CF_4$=25 sccm, P=183 W, P=40 mT,
  Si Recess Etch
    Wet etch in $NH_4F:H_2O:HNO_3$=3; 33:64 by volume, $T_{etch}$=4 mins
    Rinse 2 mins in DI, spin dry
  Field Implant
    Boron, 5e13/cm$^2$, 60 kev
  Strip resist
    PRS-2000, 15 min, 100° C.
    Acetone 3 mins
    Propanol 3 mins
    Rinse 5 mins in DI, spin dry
  Field Oxidation
    Standard prefurance clean
    Grow 680 nm of silicon dioxide: $O_2$, $T_{dep}$=dry 5 mins/wet 70 mins/dry 5 mins, 1100° C.
    Anneal 10 min in $N_2$
  Oxynitride strip
    Wet etch in BHF for 15 sec
    Rinse 5 mins in DI, spin dry
  Strip nitride
    Wet etch in hot phosphoric acid for 30 mins at 160° C.
  Pad Oxide Etch
    Wet etch in BHF for 45 sec
    Rinse 5 mins in DI, spin dry Sacrificial gate oxide growth
  Standard prefurance clean
  Grow 40 nm of silicon dioxide: dry $O_2$, $T_{dep}$=22 mins, 1000° C.
  Anneal 10 min in $N_2$
Polysilicon deposition
  Deposit 52 nm of LPCVD nitride: 625 C, Tdep=52 min
Lithography 2: Poly
  Spin HMDS 4 k rpm for 30 s
  Spin 220 4 k rpm for 10 sec
  Softbake on hot plate for 90 s at 115 C
  Expose 5 sec at 25.0 mW/cm2
  Post-exposure bake on hot plate for 90 s at 115 C
  Develop in MIF 300 for 2 mins
  Rinse 2 mins in DI, spin dry
Polysilicon etch
  RIE etch of 52 nm of polysilicon, P=65 W, P=5 mT, $SF_6$=20 sccm, $O_2$=3 sccm
Strip resist
  PRS-2000, 15 min, 100° C.
  Acetone 3 mins
  Propanol 3 mins
  Rinse 5 mins in DI, spin dry
Source/Drain Oxide Etch
  Unmasked
  Wet etch in buffered HF for 45 sec
  Rinse 5 mins in DI, spin dry,
Source/Drain Predep
  Standard Prefurance clean with HF dip
  Phosphorus diffusion: $POCl_2$: 450 sccm, $O_2$: 150 sccm, 950° C., 20 mins
Source Drain Drive-in
  Grow 140 nm of silicon dioxide: $O_2$, $T_{dep}$=dry 5 mins/wet 15 mins/dry 5 mins, 950° C.
  Anneal 10 min in $N_2$
Strip polysilicon
  Wet etch in $NH_4F:H_2O:HNO_3$=3; 33:64 by volume, $T_{etch}$=4 mins
  Rinse 2 mins in DI, spin dry
Strip sacrificial gat oxide
  Wet etch in buffered HF for 45 sec.
  Rinse 2 mins in DI, spin dry
Gate oxide growth
  Standard prefurance clean
  Grow 40 nm of silicon dioxide: dry $O_2$, $T_{dep}$=22 mins, 1000° C.
  Anneal 10 min in $N_2$
Nickel Catalyst Deposition
  Evaporate 7 nm of nickel onto wafer
Lithography 2: Poly
  Spin HMDS 4 k rpm for 30 s
  Spin 220 4 k rpm for 10 sec
  Softbake on hot plate for 90 s at 115 C
  Expose 5 sec at 25.0 mW/cm2
  Post-exposure bake on hot plate for 90 s at 115 C
  Develop in MIF 300 for 2 mins
  Rinse 2 mins in DI, spin dry
Nickel etch
Gate oxide etch
  Wet etch in buffered HF for 45 sec
  Rinse 2 mins in DI, spin dry
Passivation nitride Deposition
  PECVD deposit 500 nm of silicon nitride at 380 C.
Lithography 4—Contact Opening
  Spin HMDS 4 k rpm for 30 s
  Spin 220 4 k rpm for 10 sec
  Softbake on hot plate for 90 s at 115 C
  Expose 5 sec at 25.0 mW/cm2
  Post-exposure bake on hot plate for 90 s at 115 C
  Develop in MIF 300 for 2 mins
  Rinse 2 mins in DI, spin dry
Passivation nitride etch
  Plasma etch, P=100 W, P=100 mT, CF=40 sccm, O2=1 sccm
MWNT Grow
  PECVD Acetylene: ammonia=54 sccm:200 sccm, P=5 mBar, T=675 C.

III. CNT Islands Pattern; FIG. [3] CNT Patterned Islands. This CNT Pattern and Process is Representative of a Multi-sensor Chip Design.

Process Description. A process for forming a doped CNT assembly electrode array having CNT patterned islands is illustrated in FIG. 11. The process starts with a 100 mm silicon wafer substrate (1102) with a 500 nm thermal oxide layer (1104) on top (step 1). The patterning of electrically conductive layer (1106) is performed in a two-step lithography process. In the first step, a liftoff resist is spin coated, and baked. In the second step, a conventional photo-resist is spin coated, exposed, and developed. During resist development, the developer not only removes the exposed photo-resist, it also removes and undercuts the liftoff resist such that when the wafer is immersed in acetone, the subsequent metal stack is lift off leaving a clean metal definition. Then a stack layer of TiW/Mo/TiW: 40 nm/40 nm/40 nm is sputtered, followed by a reactive sputtering of 15 nm TiN to yield the electrically conductive layer (1106). The metal stack is then liftoff by immersing in acetone. After that, a conventional liftoff process is performed where photo-resist is patterned to define the gold contact pad, followed by evaporation of a 50 nm of gold metal (1108), and immersion in acetone liftoff solution. Similarly, the 7 nm nickel catalyst layer (not shown) is patterned by liftoff process using the liftoff resist to produce a sharp nickel metal interface (step 4). Next, a 500 nm layer of PECVD silicon nitride passivation layer (1110) is deposited at 380 C. (step 5). Contact holes are patterned to expose the metal contact pads (1108) by e-beam lithography and etched in reactive ion etching (step 6). After that, the wafer is ready for MWNT (1116) growth (f) where wafer is exposed to acetylene and ammonia gas at 400 C. (step 8), followed by further chemical functionalization (g) (step g) to dope the MWNTs (not shown).

Process Flow
  Starting Wafer
    p-type boron doped 100 mm silicon wafer, single side polished
  Thermal oxide Deposition
    500 nm thermal oxide at 1000 C. for 30 mins
  Lithography 1—Interconnect
    Spin LOR-5a 40 H rpm for 10 sec
    Softbake on hot plate for 5 mins at 180 C.
    Spin 220 4 k rpm for 10 sec
    Softbake on hot plate for 90 s at 115 C.
    Expose 5 sec at 25.0 mW/cm2
    Post-exposure bake on hot plate for 90 s at 115 C
    Develop in MIF 300 for 2 mins
    Rinse 2 mins in DI, spin dry
  TiW/Mo/TiW/TiN Interconnect Deposition
    Sputter 40:40:40 nm of TiW/Mo/TiW onto wafer
    Sputter 15 nm of Ti under nitrogen environment
    Liftoff in acetone
    Rinse 2 mins DI, spin dry
  Lithography 2—Contact Pad
    Spin HMDS 4 k rpm for 30 s
    Spin 220 4 k rpm for 10 sec Softbake on hot plate for 90 s at 115 C.
Expose 5 sec at 25.0 mW/cm2
Post-exposure bake on hot plate for 90 s at 115 C
Develop in MIF 300 for 2 mins
Rinse 2 mins in DI, spin dry
Gold Metal Pad Deposition
Evaporate 10:100 nm of Cr/Au onto wafer
Liftoff in acetone
Rinse 2 mins DI, spin dry
Lithography 3—Catalyst Deposition
Spin LOR-5a 40 H rpm for 10 sec
Softbake on hot plate for 5 mins at 180 C.
Spin 220 4 k rpm for 10 sec
Softbake on hot plate for 90 s at 115 C
Expose 5 sec at 25.0 mW/cm2
Post-exposure bake on hot plate for 90 s at 115 C
Develop in MIF 300 for 2 mins
Rinse 2 mins in DI, spin dry
Nickel Catalyst Deposition
Evaporate 7 nm of nickel onto wafer
Liftoff in acetone
Rinse 2 mins DI, spin dry
Passivation nitride Deposition
PECVD deposit 500 nm of silicon nitride at 380 C.
Lithography 4—Contact Opening
Spin HMDS 2 k rpm for 20 s
Spin 950K-A2 5 k rpm for 45 sec
Softbake on hot plate for 30 mins at 180 C.
Expose 1000 pAs/cm at 30 kv
Post-exposure bake on hot plate for 2 mins at 100 C.
Develop in 1:3 MIBK:IPA for 2 mins
Rinse 2 mins in DI, spin dry
Passivation nitride etch
Plasma etch, P=100 W, P=100 mT, CF4=40 sccm, O2=1 sccm MWNT Grow
PECVD Acetylene: ammonia=54 sccm:200 sccm, P=5 mBar, T=675 C.

III. Integrated Multi-Sensor Pattern:

FIG. [4] depicts a plan view of a four sensor chip lay-out comprising two electrolytic cell Sensor Structures and two CNT-gated MOSFETs. In this four sensor chip design one reference electrode ("RefEl") services the FETs and the other Ref El and counter electrode is combined with the two CNT Working electrodes.

Figure 5:
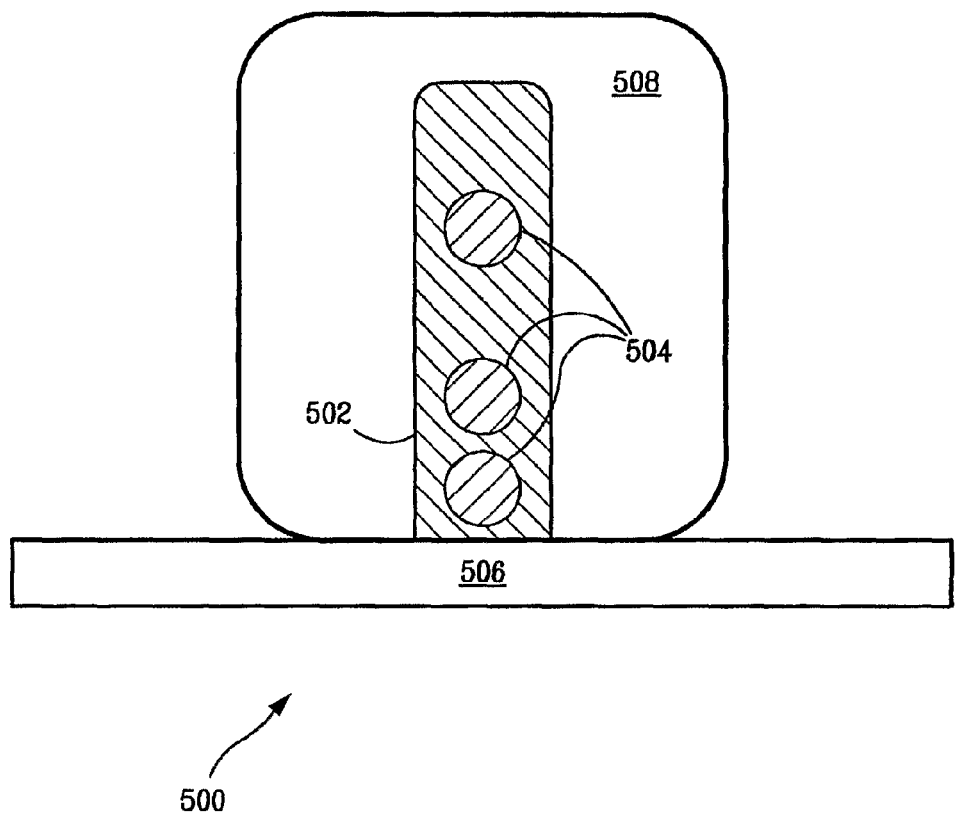
FIG. 5 is a schematic illustration of a cladded CNT peapod used in various embodiments of the present invention.

Fabrication Process (Multi-sensor Chip) The fabrication process comprises a combination of steps as described above for patterning CNT islands and FET structures. FIG. 5 is a schematic illustration of a cladded CNT peapod used in various embodiments of the present invention. CNTs can be chemically doped from within and outside the graphene wall. Suitable polymer claddings may comprise a variety of functional groups, i.e., conductive and insulating polymers, donor/acceptor semi-conducting polymers, redox active polymers, or any combination thereof. The peapod or cladding can also be doped with ionophores for the specific detection of ions in certain embodiments. Referring to FIG. 5, the cladded CNT peapod structure includes both a polymer outer coating as well as an internal reagent. This is a generic approach to chemically doped CNTs that augments the direct chemical and structural modification of the graphene wall itself. Polymers claddings may comprise of a variety of chemical functionality, i.e., conductive polymers, donor/acceptor semi-conducting polymers and redox active polymers. The CNT may be altered in p or n character, may be functionalized with reactive molecules, or any combination thereof.

FIG. 6 is a representative set of chemical compounds and polymers that form the CNT claddings and peapods. Suitable dopant materials for cladded-peapod CNTs include ionophore charge carriers, redox polymers, ion exchangers, conductive polymers, and any combination thereof. The 18-Crown-6 polyether dopant is selective ligand for cations. Cryptands, calyxarenes and open chain polyethers are better ionophore performers as are the naturally occurring antibiotics, examples of which include valinomycin, monensin, and nonactin. Examples of conductive polymers are; electronic conduction redox polymers, ionic conduction ion-exchange polymers and electron donor/acceptor co-polymers. CNT electrolysis mediation may occur by direct exchange of electrons between the redox polymer and the solution phase species, or indirectly by modulation of the donor/acceptor conductivity or ion exchange rate, or both.

FIG. 7 provides illustrations of representative donor-acceptor polymer chemistries for CNT cladding dopants. These dopants modify the p-n character of CNTs using one or more polymer coatings. Donor-acceptor polymer dopants are particularly useful as p-n character modifiers of CNTs and are preferred over the use of metal impurity dopants. Donor-acceptor polymer dopants are can be readily synthesized free of impurities. Donor-acceptor polymer dopants are readily applied as claddings on the CNTs using RF plasma polymerization that is well known in the art. Tetracyano quinine ("TCNQ") and iodine are representative electron acceptors for the polymers described.

Figure 8A:
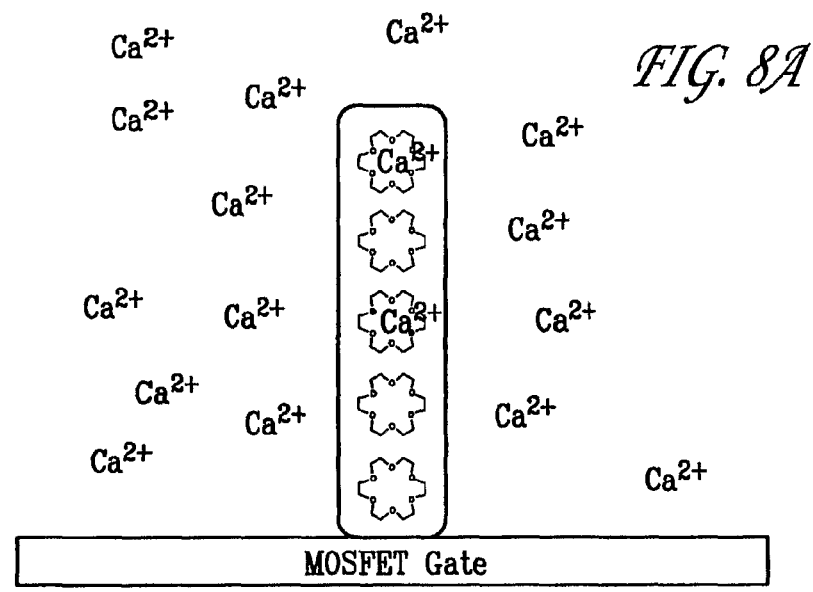
FIG. 8A provides a schematic illustration of an embodiment of an element of a peapod CNT array FET of the present invention that can be used as a calcium ion selective sensor.
Figure 8B:
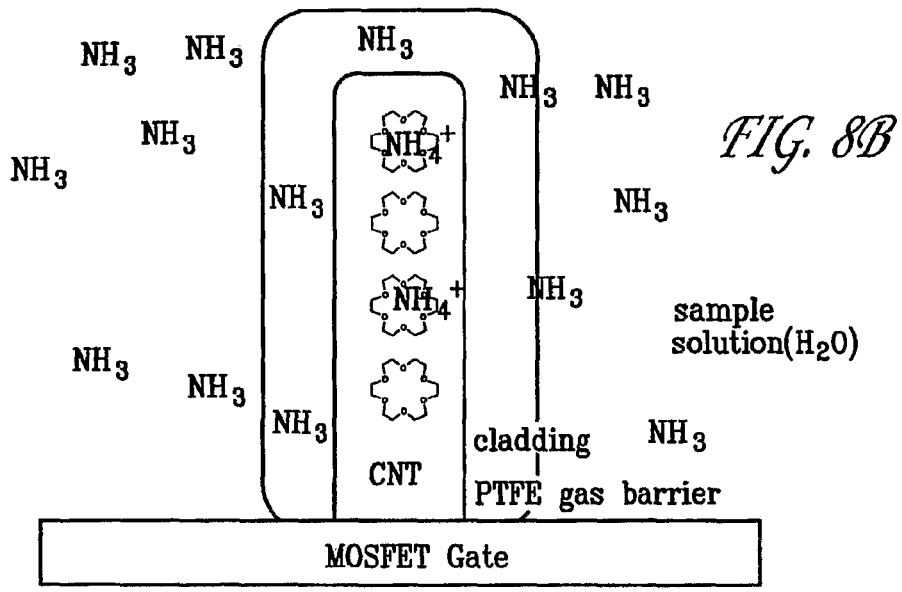
FIG. 8B provides a schematic illustration of an embodiment of an element of a cladded peapod CNT array FET of the present invention that can be used as an ammonia ion selective sensor.

FIGS. 8A and 8B provide schematic illustrations of a calcium ion selective sensor and an ammonia sensor. These sensors are charge coupled devices based on a FET design using peapod CNTs and cladded peapod CNTs. In FIG. 8B, the cladding can be PTFE which functions as a gas permeable barrier and the ionophore is selective to ammonium ion in the peapod. This is specific for ammonia gas because of the gas barrier and specificity for $NH_4^+$. A comparable structure for carbon dioxide gas would employ pH ionophore in the peapod for specific $CO_2$ gas detection. A variety of other CNT-based sensor elements can be provided according to these design principles.

Suitable cladding includes any material that can function as a gas permeable barrier. Examples of suitable cladding materials include polymers, such as polytetrafluoroethylene ("PTFE"), and sol-gel ceramic materials, polymer/sol-gel hybrid materials, and any combination thereof. In this example, the 16-Crown-6 ether ionophore is selective to ammonium ion in the CNT peapod. This combination of cladding and peapod CNT is specific for ammonia gas because of the PTFE gas barrier and the specificity of the 16-Crown-6 ether ionophore for $NH_4^+$. A comparable structure for detecting carbon dioxide gas could employ a pH-specific ionophore in the peapod to detect pH change in response to $CO_2$ permeation into the peapod.

MWNTs Structure and Chemistry of Dopants. A MWNT (CNT) sensing device is provided that selectively responds to sample chemical composition at the molecular level. The CNTs can be functionalized and/or chemically doped with selective chemical agents that respond to chemical or electrical signals. In some embodiments the doping modifies the electrical conduction properties of the CNT and in other embodiments, chemical receptor sites can be constructed to elicit specific response. In one example, the CNT is polymer coated and doped with ionophore so that the CNT accumulates ionic charge. The charge is then measured by capacitive coupling to an electronic device such as a transistor.

Certain embodiments exploit the unique electrical, structural and chemical properties of CNTs to create sensing elements that function at the molecular level. Without being bound by any particular theory of operation, doped CNT array sensors may be viewed as nanoantennas that can transmit or receive electrical signals from its environment. As such, the antennas can be modified to react with chemical specificity, and such modification is depicted as the polymer-cladded CNT peapod on FIG. (7). Combinations of peapod structure (Luzzi patent) and cladding structure and CNT surface functionalization can be structured to create chemically specific molecular level responsive antennas.

Figure 9:
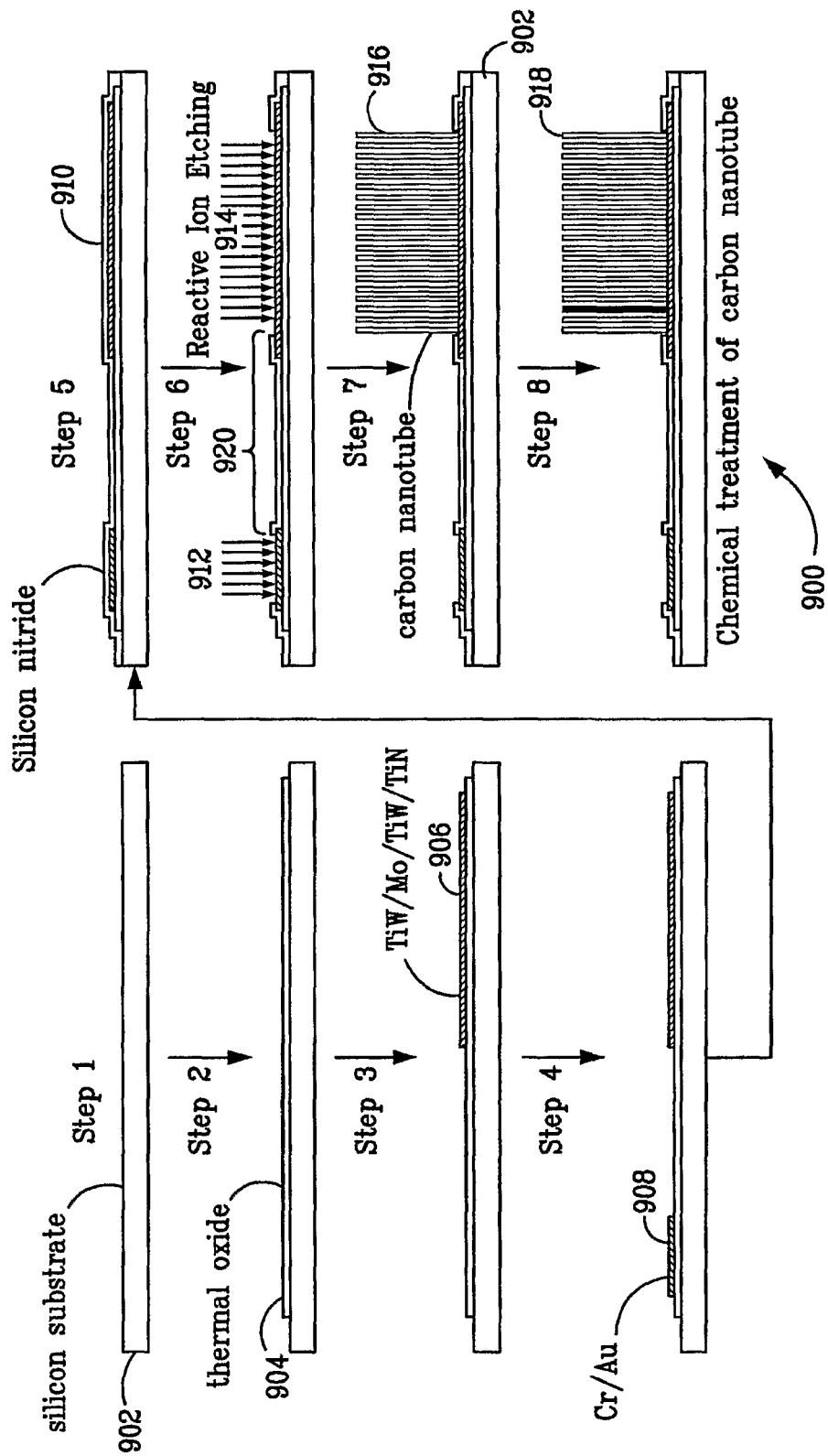
FIG. 9 provides a schematic illustration of an embodiment of the method of the present invention for making a CNT array electrode.

CNTs can be doped to behave as semiconductors varying in electrical conductivity from "metal-like" to virtual insulators. The graphene can be modified or doped to effect dramatic changes in the electron transfer or propagation by attaching electron withdrawing groups on its surface (D S. Soane, Polymers in Microelectronics, Elsevier (1989)). Donor-acceptor polymer dopants influence CNT transconductance, or redox functionalized polymeric agents can mediate electron transfer across the graphene structure/solution interface. Doping chemistry to effect p/n semi-conducting character of CNTs is shown by FIGS. 9&10.

Ionophore CNT dopants can specifically interact with one or more ions in solution and electronically measured with a CNT gated FET. Redox reactive molecules also can include dopants that mediate current flow in an electrochemical cell device. One embodiment is described below to detect chlorine in drinking water. Other embodiments can detect ions or redox molecules that are coupled to enzymes (suitable enzymes are disclosed in S P Colowik, et. al., "Methods in Enzymology", Vol. XLVI, K. Mosbach Ed.,(1976)), antibodies (suitable antibodies are disclosed in M. Z. Atassi, et. al., "molecular Immunology", Dekker, NY, (1984)), and DNA functionality (suitable DNA functionality is disclosed in L. Snyder, et. al., Molecular Genetics of Bacteria", ASM Press, Washington D.C., (1997)) to achieve biochemical specificity and sensitivity for such cladded-CNT peapod "antennas".

Suitable CNTs can vary in diameter from approximately 1 nanometer to 10 nanometers or more. CNTs may be as short as a fullerene sphere structure or as long as a few micrometers (Ajayan Review article). CNTs can be grown perpendicularly on surfaces (e.g., Si) to create densely packed, aligned NTs (or arrays) or patterned as arrays of aligned CNTs with space apart relationship templated by nanofabrication methods (e.g., E-beam lithography and plasma etching). The array pitch is controlled by E-beam lithography so that the final structure is of fixed CNTs diameter, length, and spacing. Random spacing is achieved by sputtering catalyst and is a useful process when precise pitch is not required by the design.

CNTs can be grown by chemical vapor deposition on templated catalytic surfaces to control CNT chemistry and structure uniformity, particularly for aligned CNT array arrays. Such arrays function and independent nanoelectrodes in electrolytic cells to function as nearly ideal (high current density/efficiency) electrodes that can be unencumbered by solution medium measurement artifacts such as Ohmic loss caused to solution resistance. Without being bound by any particular theory of operation, this property of CNT electrodes allows accurate current measurement in water samples which conductivity can vary dramatically in electrolytes content from drinking water (no salt/high electrical resistance) to sea water (with high salt content/no resistance). This is accomplished without manipulation of sample composition, a useful characteristic of sensors applied to continuous monitoring.

CVD growth process can generate a distribution of CNT's structures relative to graphene chirality and tube lumens. The tubes can exist as single wall nano tubes ("SWNTs") or multi wall nano tubes ("MWNT's"). SWNTs work best as transconductance channels for FET structures and can be deployed as voltage gated, chemically gated devices, or both. Without being bound by any particular theory of operation, MWNT make better cladded CNT electrodes because the inner graphene wall structure is preserved and less likely to be impeded by the polymer coating. The outer graphene wall can be chemically altered by functionalization and not interfere with the inner graphene electrical properties. Although literature has focused on SWNT channel FET, practical voltage gated poly-I-FET may function best with polymer cladded MWNTs. Peapod sensing structures can be either SWNTs or MWNTs. When both the cladding and the CNT peapods can be doped MWNT's, the electrochemical nature of the CNTs display unusual characteristics due to the coupling reactions of reactive species electrochemically generated at either side of the graphene lumen interphase.

CNT Growth Process: Aligned multiwalled MWNTs by thermal chemical vapor deposition. MWNTs (CNT's) may exist as single-walled graphene cylinder structures (SWNT) or Concentric cylinder structured multi-wall MWNTs (MWNT) (Dresselhaus, M. S; Dresselhaus, G. and Eklund, P., Science of Fullerenes and Carbon)-(Ebbsen, T., MWNTs, CRC Press, Boca Raton, Fla., (1997)) (Saito, R.; Dresselhaus, G. and Dresselhaus, M. S., Physical Properties of Carbon). The MWNT growth processes adapted for this invention can be based on Chemical Vapor Deposition (CVD). The primary requirements for CNT growth are; a catalyst consisting of transition metals (i.e., Fe, Ni, Co), Carbon source and high Temperature (500-900 deg. C.).

A. Gas phase thermal CVD method: The CVD reactor is sealed and flushed with Ar (100-300 Sccm) gas for 20-30 minutes. The whole furnace is set at 900° C. Ammonia is introduced in the system at a flow rate ranging from 20-250 Sccm, when the furnace temperature exceeds 600° C. The substrate is treated with ammonia gas inside the furnace for 15-20 minutes to form nanometer size catalytic particles. When the furnace temperature reaches the set value, Acetylene is introduced in the gas feed with a flow range of 20-300 Sccm. The flow ratio of ammonia and acetylene is optimized to get uniform ACNTs array. Acetylene gas is the source of carbon for the growth of the nanotubes. The growth time ranges from 10 to 30 minutes depending on the CNT length required.

Figure 12:
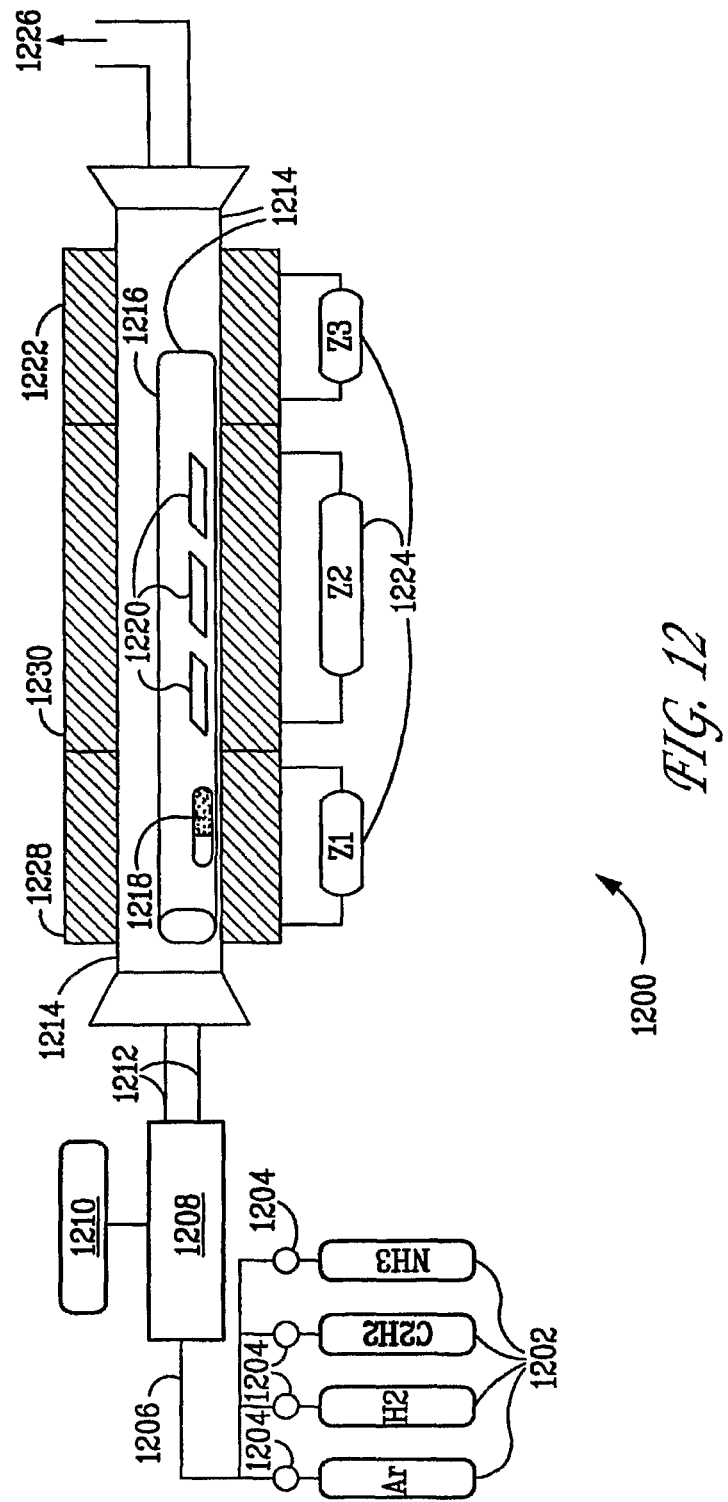
FIG. 12 provides a schematic illustration of a suitable CVD furnace and auxiliary equipment for preparing CNT array electrodes of the present invention.

B. Solid precursor thermal method: Iron (II) phthalocyanine is used as both the carbon source and the catalyst for preparing aligned MWNTs (Huang, S.; Dai, L. and Mau, A. W. H., J. Phys. Chem. B. 103, 4223 (1999)). The substrate (Silicon Chip) is cleaned with acetone in an ultrasonic bath, rinsed with acetone again and finally dried in air before placing it in zone 2 (1230) of the flow reactor (1214) (quartz tube) (1214) (refer FIG. 12). Iron (II) pathalocyanine (0.3-0.5 g) is placed in another quartz/ceramic boat and placed in zone 1 of the quartz tube. The whole system is sealed and flushed with argon (Ar) for 20-30 minutes. This step removes any oxygen present in the quartz tube and provides an inert reaction atmosphere. The flow rate of Ar is reduced to 10 Sccm and $H_2$ is introduced in the gas flow at 20 Sccm. The gas flow is maintained steady through out the reaction. The temperature of zone 2 is set at 550° C. Zone I temperature is set at 500° C. As zone 1 attains the set temperature, the pyrolysis of the organometallic precursor is triggered inside the furnace. Iron is released into the gas phase and gets spread inside the furnace and onto the substrate via the Ar/$H_2$ gas flow. The pyrolysis step is maintained for 5 minutes. Following the pyrolysis step the zone 2 temperature is set to 900° C. and zone 1 is set to 800° C. As the temperature of zone 1 ramps up the organometallic precursor remaining in the boat starts decomposing, releasing carbon in the gas phase. The carrier gas transports the carbon in the gas phase to the high temperature zone 2 where the growth of MWNTs on the quartz plate is initiated by the metal catalyst. The furnace is maintained for 10 minutes when zone 1 and zone 2 reach their set temperatures. After the reaction time, the furnace is shut-off, the $H_2$ flow is turned off, and only Ar gas flow is maintained steady at a low flow rate. The black layer that forms on the Si substrate is analyzed ant micron resolution by SEM and subsequently at sub-micron resolution by transmission electron microscopy ("TEM").

C. Plasma Enhanced CVD (PECVD), patterned growth Method: The MWNTs can be grown in a bell jar vacuum chamber at a base pressure of ~10-2 Torr. Si/SiO2 and Si/TiN substrates with Ni metallization patterns can be used for PECVD patterned CNT growth. The metal catalyst film thickness ranges from 50-150 nm. The substrate is place in the chamber and pumped down to ~10-2 Torr pressure, at a temperature setting of 700° C. Ammonia etch gas (50-200 Sccm) is first introduced into the chamber for 5-10 minutes and subsequently followed by CNT growth acetylene gas at a nominal gas flow ratio (1:2-5) of acetylene to ammonia. The glow discharge plasma generator is set at 0.5-1 kV dc and depositions can be carried out at a bias current of ~0.1 A. The growth reaction time can vary from 5-20 min depending on the required length of MWNTs and growth is observed only where the metal catalyst particle resides.

CNT Cladding Methods: Polymer CNT Claddings by Electrolytic Method: Conductive polymer films can be deposited electrolytically by monomer reduction at an electrode surface. Monomer reduction generates free radical that initiates and propagates the polymer synthesis (i.e., polymerization). Polymerization terminates when current ceases and the surface is passivated to electrolysis. Electrolytic polymerization is accomplished with suitable monomers including aniline, pyrrole, thiophene, phenol, or any combination thereof.

(i) Polypyrrole cladding method by constant voltage electrolysis: A potential of 1.0 V (VS. Ag/AgCl) is applied for 90 s in an aqueous solution of 0.1 M pyrrole and 0.1 M sodium per chlorate. Polypyrrole deposition is achieved on an aligned MWNT electrode. The electrolysis current exponentially decays during the polymer film formation and is a clear indicator for complete polymer coverage of the CNTs. Cladding formation is verified by SEM pre and post-electrolysis (ii) Polyaniline cladding method by voltage scan electrolysis: The cyclic voltametric technique is effective for the preparation of aligned MWNT/polyaniline films. An aqueous electrolytic solution of 0.05 M aniline with 0.1 M of sulfuric acid is used to electrochemically deposit polyaniline over individual aligned MWNT surface. Controlling the scan rate and the number of cycles, a uniform and smooth coat of polymer can be obtained on the surface of the individual aligned nanotubes. Cyclic scanning of voltage allows for more controlled depletion of monomer during the electrolytic polymerization resulting in more uniform films.

B. Cladding of ACNT surface by plasma polymerization technique: RF Plasma polymerization of dielectric monomers such as aliphatic hydrocarbons, substituted hydrocarbons, etc. is an attractive surface polymerization method of typically unreactive molecules to create dielectric films. A bell jar type reactor can utilized with radio frequency glow discharge to initiate and propagate polymerization. The added advantage is that these films includes created at low pressure in the gas phase under in clean-controlled environments (Iriyama, Y.; Yasuda, T.; Cho, D. I. and Yasuda, H., J. Appl. Polym. Sci. 39, 249 (1990)) (Terlingen, J. G. A.; Gerritsen, H. F. C.; Hoffman, A. S, and Feijen, J. J. App Polym. Sci. 57, 969 (1995)) (Terlingen, J. G. A.; Gerritsen, H. F. C.; Hoffman, A. S, and Feijen, J. J. Appl Polym. Sci. 57, 969 (1995)). The process is quite generic for deposition of polymers16 (For a general reference on plasma polymerization, see: (a) Yasuda, H. Plasma Polymerization; Academic Press: Orlando, (1995). (b) van Os, M. T.; Menges, B.; Forch, R.; Knoll, W.; Timmons, R. B. and Vanes°, G. J., Mater. Res. Soc. Symp. Proc., 544, 45 (1999) (c) Hsieh, M. C.; Farris, R. J.; McCarthy, T. J. Macromolecules, 30, 8453 (1997) (d) Chatelier, R. C.; Drummond, C. J.; Chan, D. Y. C.; Vasic, Z. R.; Gengenbach, T. R.; Griesser, Langmuir, T. J., 11, 4122 (1995)), for immobilization of surfactant molecules17 (Terlingen, J. G. A.; Feijen, J.; Hoffman, A. S. J., Colloid Interface Sci. 155, 55 (1993)), or etching of the specimen surface18 (Manos, D. M. and Flamm, D. L., Plasma Etching, An Introduction, Academic Press: Boston, (1989)). The system depicted in FIG. 13 can be utilized for radio frequency sputtering and plasma polymerization.

Figure 13:
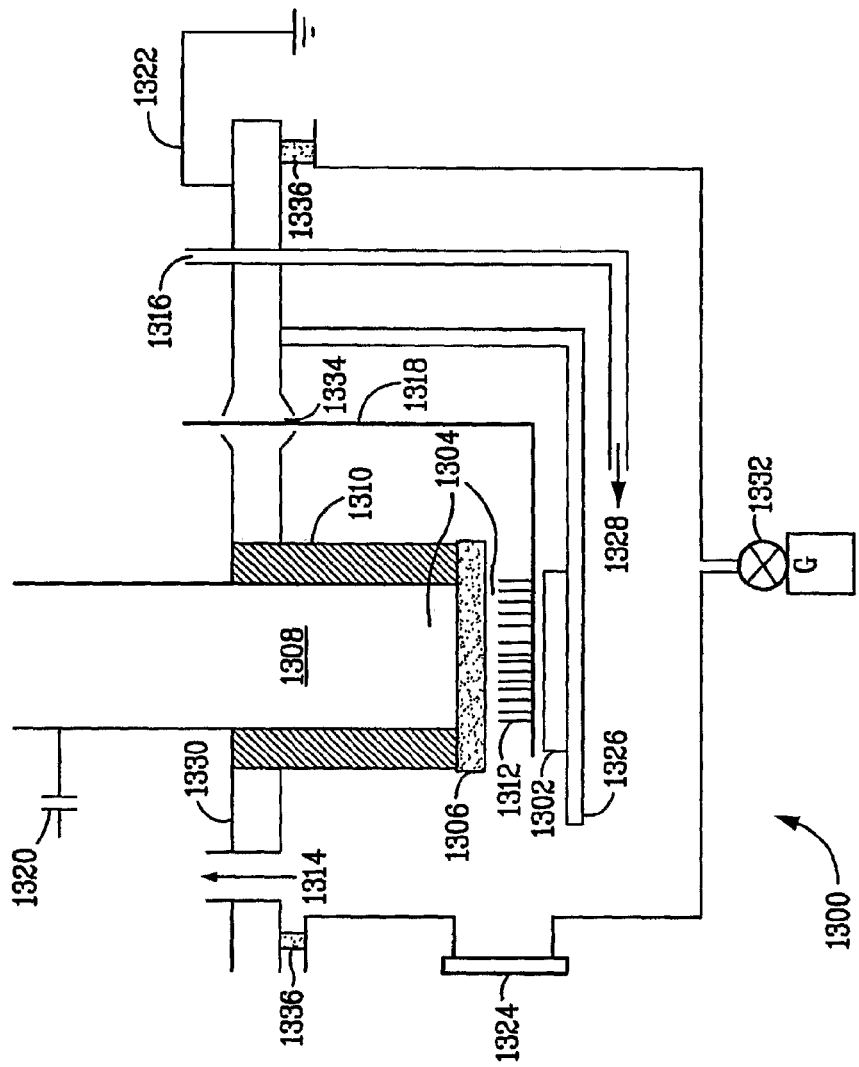
FIG. 13 provides a schematic illustration of equipment suitable for radio frequency sputtering and plasma polymerization of polymer cladding materials used in various embodiments of the present invention.

FIG. 13 illustrates a radio frequency deposition system (1300) having a substrate (1302), sheath (1304), target (1306), excitation electrode (1308), insulation of excitation electrode (1310), discharge glow (1312), passage to pumps (1314), inlet for monomer gas or argon gas (M, Ar)(1316), shutter (1318) and power supply (1320) indicated by radio frequency.

Procedure to coat ACNT surface uniformly with hexane plasma layer is explained. A plasma reactor powered by a commercial high voltage radio-frequency generator operating between 100-500 KHz (AG0201HV—ACD) can be used to carry out the surface modifications of aligned MWNTs. The plasma chamber is connected with a plasma generator and a vacuum line. A film of aligned MWNTs is placed inside the plasma chamber on the electrode. A small quantity of a liquid monomer (hexane) is introduced in the monomer bottle. High vacuum (~0.1 Ton) is created in the chamber, before the admission of the monomer particles in the glass chamber. Once the desired monomer pressure (~0.15-0.7 Torr) is attained, a radio frequency generator is turned on (Power—30 W, Freq—250 KHz) for the desired discharge period (30-120 s) during which time the aligned MWNT surface is modified with plasma.

CNTs Doping Chemistry. The doping of CNTs is accomplished in several ways; by direct chemical bonding of functional groups on the RF plasma oxidized graphene carbon, by filling the CNT lumen to create peapods, and by forming a polymer film (cladding) on the graphene surface. Any of all combinations of these doping procedures can be useful in creating chemically selective sensing devices.

CNT peapods can be filled with ionophores from the class of such ligands as; cyclic poly-ethers (cryptands, calyxarenes), natural antibiotics (Valinomycin, Monensin, Nonactin) and other linear ion coordination ligands known in the art (Reference Ionophore literature). Such ligands selectively bind the ion into the CNT phase and the charge accumulation is determined by complex formation constant equilibrium, solubility factors and ion (CNT/solution) partitioning factors. Because the CNT is completely neutral to all ions in a sample, only the primary ion exchange will result in a charge gradient formation within the CNT. Conventional ISE membranes respond predominantly to the ionophore-bound ion, but can be susceptible to ion exchange with the polymer sites. Secondary ion interaction of the dielectric membrane contributes to background signal and thus, limits the detection sensitivity. Theoretically, this new ion selection mechanism can lower the detection limit from 10[−8] Molar (state-of-the-art) to ~10[−12] Molar. Although this level of selectivity and sensitivity is not required for water analysis, it may be important to medical/pharmaceutical applications. Such CNT constructs can be much more durable than conventional membrane sensors that are susceptible to hydrolytic break down in water. Furthermore, the ionophores can be trapped within the CNT and will not leach as do conventional polymeric membranes.

Several electron mediators can effectively bridge the band gap and mediate electron transfer with solution or within the CNT/polymer phase: $Ru(bpy)_3 2+$, $Fe(bpy)_3 2+$, $Ru(NH_3)_6 3+$, Tetracyanoquinodimethane (TCNQ), Quinone, Benzophenone, Ferrocene, Tetramethyll-p-phenylenediamine(TMPD), Tetrathiafulvalene, Tri-N-p-tolylamine(TPTA). Such polymers, whether electron donors or acceptor or ion exchangers/ion carriers or redox centers, all can be coated onto the CNT by electrolytic polymerization or RF plasma. These films can be easily applied as coatings on the outer CNT surface.

The CNT carbon structure is chemically altered by oxidative RF Plasma to activate the carbon surface and create oxide, hydroxide, carboxyls and phthalic anhydride which will subsequently chemically bond with appropriate functional groups COOH, CONH2, COOCH3, OSiORx, etc. to provide chemical reactive functionality for Schiff base, carbodiimide, amide, etc. linkage to peptides (antibody, enzymes, DNA).

CNT Doping Method by Supercritical $CO_2$

I. Super Critical $CO_2$ Assisted MWNT Doping (Peapod Formation).

Goal: To drive target molecule (e.g. $Ru(bpy)_3^{2+}$, $C_{60}$) into the cavity of MWNTs.

Materials: Silicon chip with CNT array pattern [FIG. (1)], Fullerene ($C_{60}$), $Ru(bpy)_3^{2+}$.

Solvents: 1,2-Dichlorobenzene, Chloroform, Tetrahydrofuran, Carbon disulfide, Ethanol, Toluene, Deionized Water.

Experimental Procedure: Aligned CNT Arrays Filled with Ru(Bpy).
  (i) CNT-chip preparation: (Air oxidation—Optional): Heat the SWNTs under oxygen in a muffle furnace at 600° C. for ~5 minutes. Weigh the CNT chip after heating, the mass of nanotubes should reduce to 30-50% of its original mass (~6-10 mg).
  (ii) Prepare a solution of Ru(bpy) in de-ionized water (e.g. 5 ml of 1 mM solution).
  (iii) Place a drop of the solution mixture the chip and dry in air.
  (iv) Introduce this wafer into the supercritical chamber. Fill the chamber with liquid $CO_2$.
  (v) Attain super criticality and maintain a pressure of 100-150 bar @ 50-60° C. temperature for 3-4 hrs.
  (vi) Collect the sample on the wafer; wash it with copious amount of de-ionized water to remove any molecules absorbed on the sidewalls of the nanotubes.
  (vii) Characterize the sample by SEM/TEM.

II. Super Critical $CO_2$ Assisted Impregnation of Ionophores onto CNT Surface.

Goal: To drive target molecule (e.g. 18-Crown-6, Potassium-ionophore) into the cavity of MWNTs.

Materials: Cladded MWNTs, Fullerene ($C_{60}$), Ionophores, Trial Solvents Chloroform, Tetrahydrofuran, Ethanol, Toluene, De-ionized Water.

Experimental Procedure:
  Prepare a film of aligned CNTs on a chip. Perform conformal cladding on the surface of the aligned CNTs.
  (ii) Prepare a solution of 18-Crown-6 in Chloroform (e.g. 5 ml of 1M) in a vial.
  (iii) Introduce the cladded—aligned CNT sample into the vial solution.
  (iv) Place this vial in a super critical $CO_2$ chamber. Seal the chamber.
  (v) Fill the chamber with liquid $CO_2$.
  (vi) Super critical conditions are achieved and thereafter the pressure is maintained at 100-150 bar @ 50-60° C. for around 3-4 hrs.
  (vii) The chamber is brought back to Room Temp and Pressure in a controlled manner, so that the dried contents remain in the sample vial.
  (viii) Collect the cladded aligned CNT sample and characterize it by SEM/TEM.

Example #1

Chlorine Detection

Free Chlorine [HClO] and Total Chlorine [HClO & RHNCl & Cl-RH] may be detected with the Device in FIG. (1) when the CNTs are configured as a Working Electrode in an electrolytic cell configuration. By the application of the appropriate votage bias of 1.1V vs. Ag/AgCl (Ref.) free Chlorine (or HClO) will directly reduce in water according to the following reactions:

A. Free Chlorine Measurement with No Dopant Requirement:

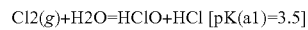
$Cl2(g)+H2O=HClO+HCl$ [pK(a1)=3.5]

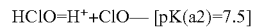
$HClO=H^+ +ClO-$ [pK(a2)=7.5]

$HClO+2e-+H2O=HCl+H2O2$

The CNT islands in FIG. (3) are defined Working electrodes patterned from the Ni catalyst surface film. E-beam lithography can define the Ni film patterns with a resolution of 20-100 nm. Within this pad dimension, several CNTs will grow to form the working electrode. The ensemble of these 100 nm CNT islands make up the total working electrode surface. As depicted by the above electrochemical reaction, HClO will reduce to HCl and other chlorinated hydrocarbons and amines will similarly reduce at various voltages (energies). Scanning bias voltages will induce electrolysis of electro-active sample species such that independent responses can be evoked at various voltages. The additional application of periodic perturbations (i.e., sinusoidal, pulse, etc.,) enhance the sensitivity and resolution of such electrolytic responses. Digital domain processing allows for deconvolution of response artifacts and noise filtering. Such signal processing techniques improve sensitivity and specificity by isolating signal from background and by resolving complementary signals in the time (kinetic) and voltage (energy) scale.

B. Total Chlorine by Iodide/Iodine Dopant Mediator:

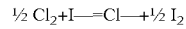
½ $Cl_2$+I—=Cl—+½ $I_2$

$RHNCl+I$—=Cl—+$RNH_2$+Cl—+½ $I_2$ Etc.

As the above reactions indicate, Iodine is a chemical reducing agent for chlorine and the I2/I— is also electroactive so that it not mediates electron transfer through the CNT but can also be reversibly regenerated after chlorine oxidation. All chlorinated organic species such as chloramines (disinfection byproducts) and oxichlorides can be reduced by iodide, hence, iodine content is a measure of total chlorine.

To effect total chlorine reduction, the CNTs can be doped with Iodine:

Method 1: The CNT sensor pad of FIG. (1) comprising of aligned CNTs (arrays) is oxidized in a furnace at 400 deg C. to create defects in the CNT. The CNTs are subsequently treated with supercritical fluid composition containing Iodine to effect phase transfer of iodine into CNT.

Method 2: The vertically aligned CNTs (array) is coated with polyanaline conductive polymer by electrolytic deposition from aniline monomer and subsequently impregnated with iodine by the scCO2.

Method 3: The vertically aligned CNTs (array) is coated with aliphatic hydrocarbon dielectric polymer deposited by RF plasma free radical polymerization of n-hexane. The dielectric polymer is subsequently impregnated with iodine by the scCO2 method above.

The total DC current measured corresponds to the rate of iodine reduction and reflecting the sum total of all chlorinated species that oxidize iodide ion to iodine. Both CNT peapods and cladded CNTs behave similarly in this mechanism as mediators, however, the peapod is a faster reaction since the electrons can be exchanged directly (tunneling) with the graphene CNT structure. In the case of the polyanaline cladded CNTs, the polymer phase conduction is likely to occur via a donor acceptor "electron hopping" mechanism.

C. Luminescence Detection mechanism for Tot Chlorine: CNT peopods are generated by the scCO2 method using the redox mediator Ru(II)(bpy)2 as photo-emitter. The CNT peapods are cladded by dielectric hydrocarbon polymer (poly-n-hexane) by the by RF-plasma free radical polymerization method. The cladding is then pregnanted with Ru(II)(bpy)2 by the scCO2 method. Samples containing chlorinated organics will react with Ru(II)(bpy)2 to yield the oxidized state Ru(III) state within the cladding while peapod Ru(II)(bpy)2 is reduced electrolytically to Ru(1). This dynamic generation of Ru (I) and Ru(III) will luminesce at 610 nm and modulated by the sample chlorine. The emission is detected by photodiode.

Example #2

Calcium Ion Detection

Charge Coupled Devices: The passive device of FIG. (1) may be applied as an ion selective ion sensor by doping the CNT array with ionophore or ion exchange ligands. Such a sensor responds to the test sample ion content according to the equation:

$$E = E° + S \ln [a_i + Kij\Sigma aij - E_{ref}]$$

where; E° is the standard potential (ln $a_i$ intercept)

(S ln $a_i - E_{ref}$) is the chemical potential term for the ion i.

Kij Σaij is the interference error term for ion j.

The assumptions are; E is referenced to Eref, slope is 50 mV for n=1, ionic strength is constant or activity coefficients χ=1, and Kij=>0. Hence, the CNT E response is a Log function of the target ion concentration (or ai).

The doping of the CNT with ionophore may assume the "peapod" structure with ionophore occupying the CNT interior void space. Alternatively, doping may be achieved by dielectric polymers coating (cladding) the CNT and impregnating the polymer with ionophore (See FIG. [10]). Examples of calcium specific ionophore and other ionophores significant to water analysis are given below:

ETH 1062—CALCIUM IONOPHORE
N,N,N',N'-Tetrabutyl-3,6-dioxaoctanedi(thioamide)

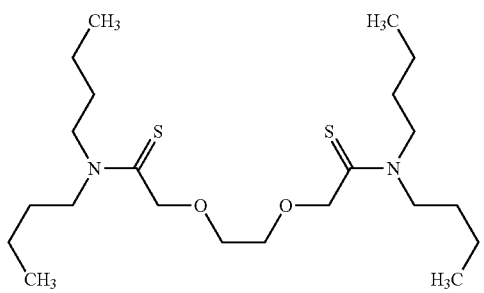 [SMILES: CCCCN(CCCC)C(=S)COCCOCC(=S)N(CCCC)CCCC]

ETH 129—CALCIUM IONOPHORE
N,N,N',N'-Tetra[cyclohexyl]diglycolic acid diamide
N,N,N',N'-Tetracyclohexyl-3-oxapentanediamide

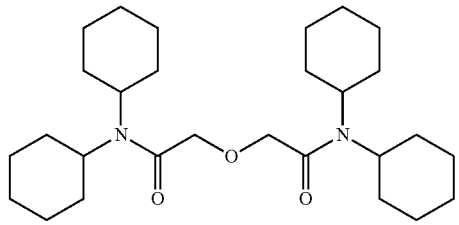 [SMILES: O=C(COCC(=O)N(C1CCCCC1)C1CCCCC1)N(C1CCCCC1)C1CCCCC1]

ETH 6010—CARBONATE IONOPHORE
Heptyl 4-trifluoroacetylbenzoate

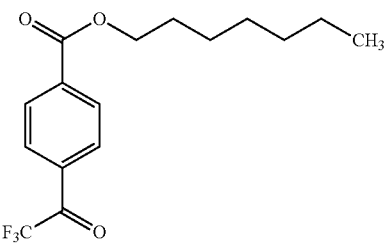

Proton ionophore I— pH
Tridodecylamine—Molecular Formula [$CH_3(CH_2)_{11}$]$_3$N

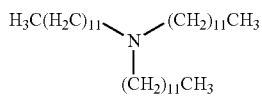

POTASSIUM IONOPHORE
Valinomycin—Molecular Formula $C_{54}H_{90}N_6O_{18}$

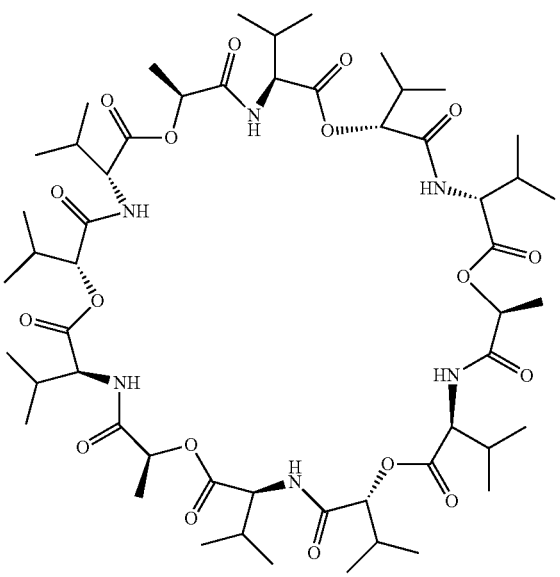 [SMILES: CC(C)[C@@H]1NC(=O)[C@@H](C(C)C)OC(=O)[C@H](C(C)C)NC(=O)[C@H](C)OC(=O)[C@@H](C(C)C)NC(=O)[C@@H](C(C)C)OC(=O)[C@H](C(C)C)NC(=O)[C@H](C)OC(=O)[C@@H](C(C)C)NC(=O)[C@@H](C(C)C)OC(=O)[C@H](C(C)C)NC(=O)[C@H](C)OC1=O]

SODIUM IONOPHORE
Bis[(benzo-15-crown-5)-4'-ylmethyl]pimelate

This structure will respond only to chemical interactions on the CNT surface when doped with ion specific ionophore

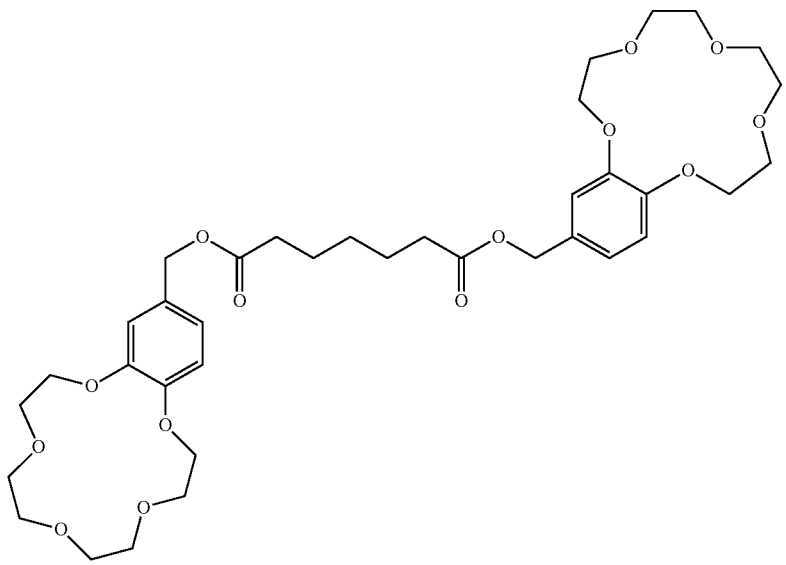 [SMILES: O=C(CCCCCC(=O)OCc1ccc2c(c1)OCCOCCOCCOCCO2)OCc1ccc2c(c1)OCCOCCOCCOCCO2]

Molecular Formula
$C_{27}H_{46}O_5$
2,3:11,12-Didecalino-16-crown-5
2,6,13,16,19-Pentaoxapentacyclo[$18.4.4.4^{7,12}.0^{1,20}.0^{7,12}$]
  dotriacontane DD-16-C-5
Molecular Formula
$C_{27}H_{46}O_5$

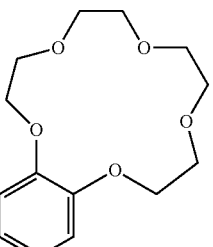

The FIG. [2] schematic is that of a doped CNT assembly (200). Here, a MOSFET Charge Coupled device can be constructed by standard IC manufacturing methods. The gate oxide (222) is coated with a (non-templated) array of aligned CNTs (238). The gate oxide (222) is electrically insulated from the p-doped channel (202) so that the resulting high input impedance ensures that charge coupling will modulate the gate electric field and consequently, the electron conduction between source (240) and drain (230). The CNT functions as an antenna to accumulate charge from solution contact to generate an electric field (not shown) that in turn modulates the p-channel MOSFET drain current according the simplified general formula: (J. Janata, et. al., in "Ion Selective Electrodes in Analytical Chemistry", V 2, H Freiser Ed., Plenum Press, 1980)

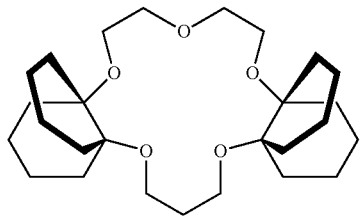

where; k is a constant re. CNT dimensions and e-mobility
  ID is the drain current
  $R_\Omega$ resistance of the CNT channel
  $V_G - V_T$ represent gate and threshold voltages
  ($S \ln a_i - E_{ref}$) is the chemical potential term for the ion i.

(i.e., 18-crown-6 cyclic polyether). The ionophore selectively binds ion (i.e., K+) specifically from solution to charge the CNT, which in turn modulates the p-channel semiconductor space charge. The chemical modulation may be measured as a gate voltage at constant drain current or modulated drain current at fixed gate bias voltage.

All CNTs (antenna filed) can respond to the same chemical entity (i.e., ion) for proper CNT-gated FET function. The signal-to-noise characteristics of such a CNT-gate FET is significantly superior to the comparative passive sensor (CNT-array), but all thermodynamic and kinetic response characteristics remain the same. The nanoantenna CNT chemical sensor is sensitive and specific (relative to the macro-membrane equivalent) because the signal focuses on the ion exchange interaction only and all artifacts regarding CNT chemical interactions liquid junction ion fluxes, etc., are non-existant.

Charged coupled mechanism of detection is based on the selective generation of an electric field on a CNT as a consequence of ion (charge) capture as described by the equations above, the solution chemical potential affects the gate voltage that modulates the source to drain current of a nominally operating FET device.

This MOSFET sensing device shown is a p-n-p FET operating in the inversion mode (large reverse voltage bias). The CNTs function as antennas and as a metal coating on the metal oxide insulator (MOI gate). The FET may or may not be operated in the Field Effect mode but as a conventional transistor with forward or reverse gate bias. In the reverse bias mode the CNT may operate as an ion-gated switch, in the forward gate bias mode as ion modulated drain current.

Several highly selective cationic ionophores for Calcium, Potassium, and Sodium ions and H+ and CO3=anion exchangers are shown above. Such ionophores target the Potable Water Panel of Table I. The ion exchange polymers shown of FIG. [8] and the donor/acceptor polymers of FIG. [9] offer fixed site polymer structural cladding alternatives for stable selective chemistry. Ion exchangers such as polysulfonates (cationic) and quaternized polyalkylammonium (anionic) are effective fixed site charge conductivity mediators for cladded CNTs. The p/n modifiers (electron donor/acceptor polymers) are effective mobile electron/hole mediators for chemically modulating CNT transconductance.

Redox reactions can also apply to modulate Gate bias. Iodine cladded CNT (I2/I-couple) will oxidize chlorine to form Iodide ion. Hence donor/acceptor polymers based on Iodine as an electron acceptor dopant will mediate both conductivity and charge and is adaptable to either FET structure discussed above. Reduction-oxidation reactions in general; TCNQ/TCNQ= and Ru++/Ru+, etc. will modulate gate bias by charge ratio and/or conductivity and hence may be coupled to target molecules of interest for application on FET devices.

Example #3

Ammonia & Carbon Dioxide Detection

The sensor of FIG. (10) is based on the cladded peapod structure of FIG. (7). It couples the ammonium ion specific CNT peapod with a gas barrier polymer cladding. PTFE cladding is an effective NH3 gas separator from dissolved NH4+OH— (ammonia) in solution. Nonactin is a selective ionophore for NH4+ that is immobilized within the peapod. NH3 permeates through the cladding and NH4+ is captured and bound by the nonactin to generate CNT charge.

Similarly, CO2 can permeate gas barrier (cladding) to bind with Heptyl 4-trifluoroacetylbenzoate as carbonate anion. Alternatively, CO2 can be detected as a pH change with Tridodecylamine. Both mechanisms separate the gas from solution and generate ionic charge on the CNT. The measurement is accomplished by electrometric EMF measurement of a passive CNT array sensor or by active CNT-gated FET device. In either case the chemical potential of the NH4+ or CO3= is in equilibrium with the EMF of the CNT.

Example #4

Sarin Toxin Detection (By Acetylcholinesterase (choline hydrolysis) inhibition reaction): Sarin (O-isopropyl methylphosphonofluoridate) inhibits the chlorinesterase catalyzed hydrolysis of acetylcholine to choline (quaternized ammonium salt). The quaternary ammonium ion is detected by cationic exchanger shown in FIG. (8) as modulated CNT conductivity. The CNT can be either peapod or ionic polymer cladded CNT. Cyclic polyethers can be selective to quaternary ammonium cations, albeit less selective than smaller ion sizes.

Example #5

Sarin Toxin Detection (By ImmunoAssay): Anti-Satin capture antibody is Sandwiched with Anti-Sarin Urease conjugate. Step I is top capture Sarin on Nonactin CNT peapods with Anti-Sarin antibody. Step II is to sandwich Anti-Sarin- Sarin- and Urease Anti-Sarin Conjugate. Detect ammonium ion generated by Urease conjugate label captured at CNT peapod surface.

In this detection scheme the combined specificity of enzyme catalysis to the specific detection of the ion generated (ammonium in this case) yields exceptional sensitivity and detection specificity. And this sensor design approach is entirely generic with respect to sandwich immunoassay mechanism. The detection scheme is the same, i.e., match the enzyme label (antibody conjugate) to the product of the enzyme reaction for chemical amplification and the capture antibody for specificity. The generation of label ion is confined to the cladding surface of the CNT (or peapod) concentrating ion product at the detection surface and the sensitivity multiplies many fold. This scheme is repeated with redox active label antibody conjugates as is the case for horse radish peroxidase (HRP) that generates peroxide on the FET gate surface. Peroxide reacts with I2/I− or Ru2+/Ru+ dopants to alter charge and/or conductivity Example #6

Microbial Identification (E-Coli)

Oligonucleotide sequences that are complementary to target $E$-$Coli$ DNA sequences will hybridizate to form dsDNA. When such hybridizations are confined to the CNT surface, the hybridization event may be detected by intercalation of transition metal ions. In the case of dsDNA hybridization on the CNT-gated FET intercalated ions, e.g., Ag+, Ru++, etc. would be detected by CNT gate voltage bias that is modulated by intercalated ion or by redox electrochemistry of the intercalated metal ions To overcome the problem of mutant mismatch (false negatives or false positives) the Ramdomly Amplified Polymorphic DNA approach would be used with a high debsity CNT sensor array to detect polymorphism populations of DNA amplicons with subsequent pattern analysis.

TABLE I

A potable water panel comprising ac chemistry profile that is a measure of water quality

| Water Parameters | Test | Selective Chemistry | Range-(Molar Units) |
|---|---|---|---|
| Potassium | K+ | Valinomycin-ISFET | $10^{-5}$-$10^{-1}$ |
| Sodium | Na+ | Calyxarene-ISFET | $10^{-4}$-$10^{-1}$ |
| Hydronium | pH | Tri-n-dodecylamine-ISFET | 5-9 |
| Calcium | Ca++ | ETH 1001- ISFET | $10^{-5}$-$10^{-2}$ |
| Chloride | Cl− | Quatemary Ammonium Polymer-ISFET | $10^{-4}$-$10^{-1}$ |
| Alkalinity | HCO3− | PTFE cladding/pH-FET | $3 \times 10^{-3}$-$10^{-1}$ |
| Oxygen | pO2 | PTFE cladding/Peapod Electrode | 0-300 mmHg |
| Ammonia | pNH3 | PTFE cladding/NH4+-FET | $10^{-5}$-$10^{-1}$ |
| Chlorine | Cl2 | HOCl reduction-Peapod Electrode | 1-10 ppm |
| Oxidation-Reduction | ORP | CNT Potential | 0-1000 mV |
| Temperature | | RTD, Diode | 5-50° C. |
| Conductivity | | Ti/Pt | 0-2000 μS/cm |

TABLE II

DRINKING WATER MONITORING APPLICATION
CNT-array Dopants Chemistry

| Sensor Category | Target Analytes | Dopants/Chemistry |
|---|---|---|
| Ion Detection (H+) | Ca++, pH | Peapod or cladding/(Ca) Ionophore/tri-alkylamine |
| Gas Detection | Ammonia; | Cladded(dielectric)/Peapods (Nonactin-NH4+) |
| | Carbon Dioxide | Cladded (dielectric)/tri-alkylamine (H+) |
| | Oxygen | Cladded Peapod CNT-electrode |
| Redox Detection | Free Chlorine; Tot Chlorine | Redox Mediator (I2), Peapod or cladding (polyanyline) ECL of $Ru(bpy)_3^{2+}$ CNT-electrode |
| | Chloramines/ ClO2 | Peapod or cladding doped w.Iodine or TCNQ |
| Toxins by Enzyme Inhibition By Immunosensor | Toxins Sarin/Risin etc. | Acetyl Choline Esterase Inhibition Immuno-assay by Cladded-Peapod Donor-Acceptor (Cladding or Peapod) Ion Detection (Cladding or Peapod) Redox Mediation (Cladding or Peapod) ECL/Peapod-Cladding Combo |
| | Chloro-Alkylamines | Cladded Peapods Ions/donor-acceptor/redox/ECL |
| Microbes by DNA Hybridization | | Cladded Peapods Ions/donor-acceptor/redox/ECL |

TABLE III

CNT SENSORS

| NT Structure | Fab Process Chemistry | Analytical Method | Target Analytes |
|---|---|---|---|
| CNT arrays-undoped | | | |
| CNT arrays | CVD growth | Votage programs; a.c. voltammetry | HClO, O2 |
| CNT Islands | CVD growth | Votage pulse transients | R—NH—Cl, Clo2 |
| CNT-gate | CNT gate-MOSFET ECL | Fourier Analysis of transients I-V measurements | HCO—Cl, Cl—CH2—CO |
| Cladded CNT's | | | |
| Dielectric Cladding | Ionophores | Potentiometry | NH3, CO2 (gasses) |
| Ionophore Functionalized | Redox Donor-Acceptor | Capacitance NT Conductivity | Ca++, pH HClO, O2 |
| Conductive polymer cladding | | Selective I-V | R—NH—Cl, ClO2 |
| Redox Functionalized | | | HCO—Cl, Cl—CH2—CO |
| Peapod CNTs | | | |
| Dielectric Cladding | | | |
| Ionophore Functionalized | Polymer grafts Ionophores | Potentiometry Capacitance | Enzyme assays Biotoxins |
| Conductive polymer cladding | | | |
| Redox Functionalized Fluors | Redox Donor-Acceptor | NT Conductivity Selective I-V Electro-chemiluminescence Fluorescence Nanotitrations | Immuno-assays Biotoxins Microbes NH3,CO2 Ca++, pH |
| Functionalization (NT's, peapods, claddings, combinations) | | | |
| of peapods | Ionophores | Potentiometry | Enzyme assays |
| of claddings | Redox | Capacitance | Biotoxins |
| of NTs | Donor-Acceptor Proteins Enymes Antibodies DNA | NY Conductivity Selective I-V Electro-chemiluminescence Fluorescence | Immuno-assays Biotoxins Microbes NH3,CO2 Ca++, pH Carcinogens |

TABLES IV

Reference numerals description used in the figures.

FIGS. 1A + 1B:

| | |
|---|---|
| 100 | doped CNT assembly electrode |
| 102 | substrate (oxidized silicon wafer) |
| 104 | electrically conductive layer (TiW/Mo/TiW/TiN) |
| 106 | catalyst (Ni) |
| 108 | metal layer (Cr/Au) |
| 110 | passivation layer (Silicon Nitride) |
| 118 | assembly of doped MWNTs |

FIGS. 2A + 2B:

| | |
|---|---|
| 200 | doped CNT assembly FET |
| 202 | p-doped |
| 214 | thermal-oxide (insulating layer) |
| 218 | silicon nitride (protective layer) |
| 222 | gate oxide |
| 224 | catalyst layer |
| 230 | drain |
| 238 | array of aligned CNTs |
| 240 | source |
| 234 | silicon nitride |

FIGS. 3A + 3B:

| | |
|---|---|
| 300 | a doped CNT assembly electrode array |
| 302 | substrate |
| 304 | thermal oxide layer or electrical conductive layer |
| 306 | nickel catalyst layer |
| 308 | metal contact layer |
| 310 | electrically conductive layer or silicon nitride insulating layer |
| 316 | contact holes |
| 318 | MWNT bundles |
| 328 | nickel metal interface |

FIG. 4:

| | |
|---|---|
| 400 | integrated multisensor |
| 402 | CNT assembly FET |
| 404 | CNT assembly working electrodes |
| 422 | CNT assembly working electrodes |
| 424 | CNT assembly working electrodes |
| 406 | electrical contacts |
| 408, 416 | electical leads to counter electrode |
| 410, 434 | reference electrodes for electrolytic cell |
| 412 | counter electrode |
| 414 | substrate |
| 418, 432 | electrical leads to reference electrodes 410, 434 |
| 420 | ? gate lead to CNT assembly FET 402 |
| 426 | ? source lead to CNT assembly FET 402 |
| 428, 430, 436 | electrical leads to CNT assembly working electrodes to 422, 424, 404 |

FIG. 5:

| | |
|---|---|
| 500 | vertically aligned doped CNT containing a fill material and having a cladding |
| 502 | CNT |
| 504 | fill material |
| 506 | catalyst layer/electrically conductive layer/substrate |
| 508 | cladding |

FIG. 9:

| | |
|---|---|
| 900 | doped CNT array working electrode |
| 902 | substrate |
| 904 | thermal oxide layer |
| 906 | electrically conductive layer |
| 908 | metal contact pad |
| 910 | silicon nitride passivation layer |
| 912 | electrical contact hole |
| 914 | reactive ion etching |
| 916 | vertically-aligned MWNT array |
| 918 | chemically functionalized CNTs |

FIG. 10 (a-r):

| | |
|---|---|
| 1000 | CNT-gated MOSFET |
| 1002 | substrate |
| 1004 | pad dioxide layer |
| 1006 | silicon nitride layer |
| 1008 | silicon recess etch |
| 1010 | boron |
| 1012 | field area |
| 1014 | thermal oxide (silicon dioxide) |
| 1016 | sacrificial gate oxide |
| 1018 | poly silicon |
| 1020 | source and drain areas |
| 1022 | 2nd gate oxide |
| 1024 | catalyst layer |
| 1026 | source + drain |
| 1028 | passivation layer (silicon nitride) |
| 1030 | contact holes |
| 1032 | CNT growth area |
| 1034 | metal contact |
| 1036 | wafer exposed to acetylene + ammonia gas |
| 1038 | vertically-oriented CNT array |
| 1040 | phosphorous ion implant |
| 1042 | dopant |

FIG. 11:

| | |
|---|---|
| 1100 | Doped CNT assembly electrode array |
| 1102 | substrate |
| 1104 | thermal oxide layer |
| 1106 | electrically conductive layer |
| 1108 | metal contact pad |
| 1110 | silicon nitride passivation layer |
| 1112 | electrical contact hole |
| 1114 | reactive ion etching |
| 1116 | vertically aligned MWNT array |
| 1118 | chemically functionalized CNTs |

FIG. 12:

| | |
|---|---|
| 1200 | CNT flow reactor system |
| 1202 | gas reactants and carrier gas cylinders |
| 1204 | gas regulators |
| 1206 | gas feed inlet conduit |
| 1208 | mass flow meters |
| 1210 | channel readout |
| 1212 | flow reactor inlet gas conduit |
| 1214 | gas flow reactor exterior |
| 1216 | gas flow reactor exterior |
| 1218 | CNT solid catalyst (Iron Phtholo) |
| 1220 | quartz plate substrates |
| 1222 | furnace, zone 3 |
| 1224 | temperature controllers |
| 1226 | reaction exhaust vent |
| 1228 | furnace, zone 1 |
| 1230 | furnace, zone 2 |

FIG. 13:

| | |
|---|---|
| 1300 | Radio frequency deposition system |
| 1302 | substrate |
| 1304 | sheath |
| 1306 | target |
| 1308 | excitation electrode |
| 1310 | insulation of excitation electrode |

TABLES IV-continued

Reference numerals description used in the figures.

| | |
|---|---|
| 1312 | discharge glow |
| 1314 | passage to pumps |
| 1316 | inlet for monomer gas or argon gas |
| 1318 | shutter |
| 1320 | power supply |
| 1322 | grounding wire |
| 1324 | entrance for substrate |
| 1326 | substrate holder |
| 1328 | outlet for monomer gas or argon gas |
| 1330 | chamber housing |
| 1332 | Gauge Pump |
| 1334 | shutter feed-thru |
| 1336 | insulators |

A wide variety of doped antennae assembly electrodes, methods, sensors, and field-effect transistors, as well as associated methods of preparation are envisioned. For example, the doped antennae assembly electrode, can comprise: an electrically conductive layer at least partially surmounting a substrate; and an assembly of doped MWNTs vertically oriented with respect to the electrically conductive layer to provide the doped antennae assembly electrode. The doped antennae assembly electrode may further comprising a catalyst at least partially surmounting the electrically conductive layer, wherein at least a portion of the doped MWNTs are attached at their ends to the catalyst. The doped antennae assembly electrodes may comprise a plurality of MWNTs having one or more fill molecules. The doped antennae assembly electrodes may have fill molecules that include molecules, molecular ions, atoms, atomic ions, or any combination thereof. The doped antennae assembly electrodes may have fill molecules that comprise one or more fullerenes, doped fullerenes, ionophores, ion exchangers, redox molecules, conductive polymers, or any combination thereof. The doped antennae assembly electrodes may include ionophores that include cyclic polyethers, antibiotics, linear chain ligands or any combination thereof. The doped antennae assembly electrodes may have cyclic polyethers that comprise 12-crown-4 to 24-crown-8 polyethers, or any combination thereof. The doped antennae assembly electrodes may have ionophores that include one or more cryptands, calixarenes, rotaxanes, or any combination thereof. The doped antennae assembly electrodes may have fullerenes that include one or more of C60, C70, C80, C90, or any combination thereof. The doped antennae assembly electrodes may include fullerenes that are doped fullerenes. The doped antennae assembly electrodes may include doped fullerenes that are filled, coated, chemically functionalized, or any combination thereof. The doped antennae assembly electrodes may include ion exchangers that include quaternized PVC, sulfonated PTFE, or any combination thereof. The doped antennae assembly electrodes may include antibiotics such as valinomycin, nonactin, monensin, iosin, or any combination thereof. The doped antennae assembly electrodes may include linear chain ligands such as poly-oxyethylene, tri-n-alkylammonium halide, or any combination thereof. The doped antennae assembly electrodes may include fill molecules that are semiconductor polymers comprising donor-acceptor pairs. The doped antennae assembly electrodes may include semiconductor polymers that comprise donor-acceptor pairs include semicarbazole/TCNQ, ionene/iodine, or any combination thereof. The doped antennae assembly electrodes may include fill molecules that comprise conductive polymers. The doped antennae assembly electrodes may include conductive polymers that comprise a polypyrrole, a polyaniline, a poly-p-phenylene, a polyacetylene, or any combination thereof. The doped MWNT assembly electrods may include at least two of the doped MWNTs that comprise different fill molecules. The doped antennae assembly electrodes may include fill molecules that include a chemical agent capable of responding to a chemical or an electrical signal.

The doped antennae assembly electrodes may include a plurality of MWNTs having a cladding. The doped antennae assembly electrodes may include cladding that includes a dielectric, an ion conducting polymer, an electron conducting polymer, an ionophore polymer dopant, a redox-mediator dopant, or any combination thereof. The doped antennae assembly electrodes may include dielectric that includes a polyolefin polymer, a polyaliphatic polymer, a polysiloxane polymer, a polyurethane polymer, a polyvinylchloride polymer, alumina, or any combination thereof. The doped antennae assembly electrodes may include ion conducting polymer that includes nation, polystyrene sulfonate, polyvinylpridinium, or any combination thereof. The doped antennae assembly electrodes may include electron conducting polymer that includes a doped polymer, an electrochemically doped polymer, a redox electroactive polymer, or any combination thereof. The doped antennae assembly electrodes may include doped polymer that includes a polyionine, a polysilicon, a polysemicarbazole, a polyphenylene, a polyacetylene, a polyphenylene sulfide, or any combination thereof. The doped antennae assembly electrodes may include doped polymer that includes a dopant, the dopant comprising AsF5, I2, Li, K, BF6-, PF6-, or any combination thereof. The doped antennae assembly electrodes may include electrochemically doped polymer that includes a polypyrrole, a polythiophene, a polyphenylquinone, a polyaniline, or any combination thereof. The doped antennae assembly electrodes may include redox electroactive polymers that include polyviologen, polyvinylferrocene, poly-Ru(vbpy)3++, or any combination thereof. The doped antennae assembly electrodes may include ionophore polymer dopant that includes a crown ether, a cryptand, a sphereand, a rotaxane, an antibiotic, a non-cyclic ligand, or any combination thereof. The doped antennae assembly electrodes may include redox-mediator dopant that includes Ru(bpy)3++, Br2/Br–, Fe(phen)3+++, Co(terpy)2+++, Fe(CN)6(3–), Ru(NH3)6+++, quinone, hydroquinone, methylviologen, tetracyanoquinodimethane, benzophenone, ferrocene, tetramethyl-p-phenylenediamine, tetrathiafulvalene, tri-N-p-tolylamine, or any combination thereof.

The doped antennae assembly electrodes may include cladding that comprises one or more functional reactive groups residing upon a surface of the cladding. The doped antennae assembly electrodes may include functional reactive groups that include an oxide, a hydroxide, a carboxylic acid, an ester, an ether, a carbonyl, an amine, an amide, an epoxide, a halide, or any combination thereof. The doped antennae assembly electrodes may include cladding that includes a linker attaching the cladding to the doped MWNTs. The doped antennae assembly electrodes may include a linker that includes a Schiff base, a carbodi-imide, an amide, or any combination thereof. The doped antennae assembly electrodes may include cladding linked to a selective functionality on the surface of one or more of the MWNTs. The doped antennae assembly electrodes may include selective functionality on the surface of one or more of the MWNTs that includes a protein, a phospholipids, a nucleic acid, an electron mediator, an ionophore, or any combination thereof. The doped antennae assembly electrodes may include protein that includes an enzyme, an antibody, or any combination thereof. The doped antennae assembly electrodes may include nucleic acid that includes an oligonucleotide, DNA, RNA, or any combination thereof.

The doped antennae assembly electrodes may include at least two of the doped MWNTs comprise different claddings. The cladded doped antennae assembly electrodes may include cladding that includes a chemical agent capable of responding to a chemical or an electrical signal. The cladded doped antennae assembly electrode may include a chemical agent capable of responding to a chemical or an electrical signal.

The doped antennae assembly electrodes may include MWNTs that comprise one or more functional reactive groups covalently attached to the graphene surface of the MWNTs. The doped antennae assembly electrode of claim 42, wherein the functional reactive groups include an oxide, a hydroxide, a carboxylic acid, an ester, an ether, a carbonyl, an amine, an amide, an epoxide, a halide, or any combination thereof. The doped antennae assembly electrodes may include functional reactive groups covalently attached to the graphene surface includes a linker attached to the doped MWNTs. The doped antennae assembly electrodes may include a linker that includes a Schiff base, a carbodi-imide, an amide, or any combination thereof. The doped antennae assembly electrodes may include functional reactive groups covalently attached to the graphene surface includes a selective functionality. The doped antennae assembly electrodes may include selective functionality that includes a protein, a phospholipids, a nucleic acid, an electron mediator, an ionophore, or any combination thereof. The doped antennae assembly electrodes may include protein that includes an enzyme, an antibody, or any combination thereof. The doped antennae assembly electrodes may include nucleic acid that includes an oligonucleotide, DNA, RNA, or any combination thereof.

The doped antennae assembly electrodes may include an electrically conductive layer that comprises a metal, an electrically conductive polymer, a carbon film, or any combination thereof. The doped MWNT assembly e electrodes may include an electrically conductive layer that is a lead conductor residing between the substrate and the catalyst. The doped antennae assembly electrodes may include an electrically conductive layer that comprises Pt, Au, Ti, W, V, Mo, or any combination thereof. The doped antennae assembly electrodes may include metal that comprises a CVD-deposited metal. The doped antennae assembly electrodes may include CVD-deposited metal that comprises TiW, Mo, TiN, or any combination thereof. The doped antennae assembly electrodes may include an electrically conductive layer that is characterized as having a layer thickness in the range of from about 1 nanometer to about 1000 nanometers. The doped antennae assembly electrodes may include an electrically conductive layer that is characterized as having a layer thickness in the range of from about 10 nanometers to about 100 nanometers. The doped antennae assembly electrodes may include an electrically conductive layer that is characterized as having a layer thickness in the range of from about 50 nanometers to about 100 nanometers.

The doped antennae assembly electrodes may include catalyst that comprises Ni, Co, Fe, Ru, Rh, Pd, Os, Ir, or any combination thereof. The doped antennae assembly electrodes may include catalyst that comprises an organo-metallic catalyst, an iron-phthalocyanine, a cobalt-phthalocyanine, or any combination thereof. The doped antennae assembly electrodes may include catalyst capable of growing MWNTs. The doped antennae assembly electrodes may include catalysts capable of growing MWNTs such as nickel, cobalt, iron, or any combination thereof. The doped antennae assembly electrodes may include catalyst characterized as having a layer thickness in the range of from about 1 nanometer to about 10,000 nanometers. The doped antennae assembly electrodes may include catalyst characterized as having a layer thickness in the range of from about 500 nanometers to about 1000 nanometers. The doped antennae assembly electrodes may include catalyst characterized as having a layer thickness in the range of from about 700 nanometers to about 900 nanometers.

The doped antennae assembly electrodes may include a plurality of doped MWNTs perpendicularly oriented to the substrate. The doped antennae assembly electrode of claim 65, wherein the doped MWNTs are oriented parallel to each other. The doped antennae assembly electrodes may include a doped MWNT carpet, a doped MWNT array, or any combination thereof. The doped antennae assembly electrodes may include an electrically conductive layer that comprises a single contiguous conductive layer, and the doped MWNT carpet is in electrical communication with the single contiguous conductive layer. The doped antennae assembly electrodes may include an aligned array of nanotubes of a defined geometry and pitch oriented with respect to the electrically conductive layer. The doped antennae assembly electrodes may include an array of doped MWNTs. The doped antennae assembly electrodes may include catalyst patterned on the electrically conductive layer, and the assembly of doped MWNTs is attached to the patterned catalyst. The doped antennae assembly electrodes may include catalyst patterned as an array of islands, stripes, circles, squares, rings, triangles, polygons, or any combination thereof.

The doped antennae assembly electrodes can also be used as a working electrode in an electrolytic cell or sensor. The doped antennae assembly electrodes may include a substrate comprising quartz, aluminum oxide, alumina, silicon, a ceramic boat, chromium, iridum, aluminum, niobium, tantalum, titanium, tungsten, carbon, silicon oxide, silicon carbide, brass, bronze, silver, gold, glass, indium tin oxide, graphite, platinum, magnesium aluminum oxide, platinum crucible, magnesium aluminate spinel, or any oxide, alloy, or combination thereof. The doped antennae assembly electrodes may include one or more layers of quartz, aluminum oxide, alumina, silicon, a ceramic boat, chromium, iridum, aluminum, niobium, tantalum, titanium, tungsten, carbon, silicon oxide, silicon carbide, brass, bronze, silver, gold, glass, indium tin oxide, graphite, platinum, magnesium aluminum oxide, platinum crucible, magnesium aluminate spinel, or any oxide, alloy, or combination thereof.

Sensors may include any of the doped MWNT electrodes described herein. Likewise, field effect transistors may include any of the doped MWNT electrodes described herein.

Methods of making doped antennae assembly electrodes may include the steps of: surmounting a substrate with an, electrically conductive layer; surmounting an assembly of MWNTs on the electrically conductive layer, the MWNTs being vertically oriented; and doping at least a portion of the MWNTs with a cladding, a covalent bond linkage, a functional dopant molecule, a fill material, or any combination thereof. The methods may include the step of surmounting the substrate with a thermal oxide layer, and the electrically conductive layer surmounts the thermal oxide layer. The methods may include the step of surmounting the thermal oxide layer with an electrically conductive contact pad. The methods may include the electrically conductive layer being surmounted to the substrate using a chemical vapor deposition process, a sputtering process, a fluid deposition process, or any combination thereof. The methods may include a catalyst being surmounted to the electrically conductive layer using a chemical vapor deposition process, a sputtering process, a fluid deposition process, or any combination thereof. The methods may include the chemical vapor deposition process including a gas phase thermal chemical vapor deposition method, a solid precursor chemical vapor deposition method, a plasma-enhanced chemical vapor deposition method, or any combination thereof. The methods may include a chemical vapor deposition method including microwave stimulation, radio frequency plasma stimulation, direct current plasma field enhancement, or any combination thereof. The methods may include the step of surmounting an assembly of MWNTs includes end-linking a plurality of MWNTs to the conductive layer. The methods may include the plurality of MWNTs self-assembling on the conductive layer.

The methods may include the MWNTs comprising an end-functionalized MWNT. The methods may include the conductive layer comprising functional groups that link to the ends of the MWNTs. The methods may include the MWNTs comprising an end-functionalized MWNT. The methods may include the MWNTs being provided as a dispersion of a plurality of MWNTs in a fluid, and the fluid may be an organic liquid, an aqueous liquid, or any combination thereof.

The methods may include the step of surmounting an assembly of MWNTs including growing an assembly of MWNTs on the conductive layer. The methods may include the step of growing an assembly of MWNTs includes gas phase thermal vapor deposition, solid precursor chemical vapor deposition, plasma enhanced chemical vapor deposition, or any combination thereof.

The methods may include the step of surmounting an assembly of MWNTs that includes surmounting the conductive layer with catalyst and contacting a MWNT forming composition and the catalyst at conditions necessary to grow the assembly of MWNTs from the catalyst. The methods may include the step of growing an assembly of MWNTs that includes gas phase thermal vapor deposition, solid precursor chemical vapor deposition, plasma enhanced chemical vapor deposition, or any combination thereof. The methods may include the MWNT forming composition comprising an organometallic precursor, or any combination thereof. The methods may include the organometallic precursor comprising a phthalocyanine, a porphorin, a carbon bearing ligand, or any combination thereof. The methods may preferably include the organometallic precursor comprising iron(II)phthalocyanine. The methods may include the carbon bearing ligand comprising a transition metal chelate including Fe, Co, Ni, Ru, Os, Eu, or any combination thereof. The methods may include the MWNT forming composition comprising one or more molecules composed of covalently bonded carbon atoms, hydrogen atoms, oxygen atoms, nitrogen atoms, or any combination thereof. Here, the molecules include gases comprising methane, ethane, propane, butane, ammonia, acetylene, ethylene, propylene, or any combination thereof. Alternatively, the molecules may include liquids comprising aliphatic hydrocarbons, olefins, or any isomer or combination thereof. The conditions necessary to form the assembly of MWNTs may include a temperature in the range of from about 300° C. to about 1000° C. and a pressure in the range of from about $10^{-1}$ torr to $10^{-9}$ torr. The conditions necessary to form the assembly of MWNTs may include a temperature in the range of from about 500° C. to about 700° C. and a pressure in the range of from about $10^{-6}$ torr to $10^{-9}$ torr Alternatively, plasma-enhanced chemical vapor deposition can be used to form the MWNTs.

The methods may include the step of doping that includes liquid coating, chemical vapor deposition, ion beam deposition, electrospray coating, supercritical fluid solute phase transfer, or any combination thereof. The methods may include ion beam deposition that includes electro-spray ionization, electron beam deposition, proton beam deposition, atomic ion beam deposition, molecular beam deposition, or any combination thereof. The methods may further include the step of depositing a metal on the electrically conductive layer to provide an electrode contact pad. The methods may include the electrode contact pad being distally located from the assembly of MWNTs. The methods may further include the step of patterning the assembly of MWNTs. The methods may include the step of patterning to give rise to an array of MWNTs. The methods may include the step of patterning that includes photolithography, UV lithography, e-beam lithography, reactive ion etching, chemical etching, nano-imprinting, electro-forming, or any combination thereof. The methods may further include the step of patterning the electrically conductive layer. Here, the step of patterning typically gives rise to an array of MWNTs. The step of patterning can include photolithography, UV lithography, e-beam lithography, reactive ion etching, chemical etching, nano-imprinting, electro-forming, or any combination thereof.

The methods may include the step of surmounting the substrate with an electrically conductive layer includes electroforming, electro-less deposition, electrochemical deposition, vapor deposition, sputtering, or any combination thereof. The methods may include using an assembly of doped MWNTs that comprise a plurality of MWNTs having a fill material. Fill material may include molecules, molecular ions, atoms, atomic ions, or any combination thereof. Fill material may include one or more fullerenes, doped fullerenes, ionophores, ion exchangers, redox molecules, conductive polymers, or any combination thereof. Ionophores may include ionophores include cyclic polyethers, antibiotics, linear chain ligands or any combination thereof. Cyclic polyethers may include 12-crown-4 to 24-crown-8 polyethers, or any combination thereof. Ionophores may include one or more cryptands, calixarenes, rotaxanes, or any combination thereof.

The methods may include the fullerenes including one or more of C60, C70, C80, C90, or any combination thereof. The fullerenes can be doped fullerenes. The doped fullerenes can be filled, coated, chemically functionalized, or any combination thereof. The methods may include ion exchangers including quaternized PVC, sulfonated TPFE, or any combination thereof. The methods may include antibiotics that include valinomycin, nonactin, monensin, iosin, or any combination thereof. The methods may include linear chain ligands that include poly-oxyethylene, tri-n-alkylammonium halide, or any combination thereof. The methods may include fill material that includes semiconductor polymers comprising donor-acceptor pairs Semiconductor polymers can comprise donor-acceptor pairs include semicarbazole/TCNQ, ionene/iodine, or any combination thereof. Alternatively, the fill material can include conductive polymers. Suitable conductive polymers comprise a polypyrrole, a polyaniline, a poly-p-phenylene, a polyacetylene, or any combination thereof.

The methods may include at least two of the doped MWNTs comprising different fill molecules. For example, the fill material may include a chemical agent capable of responding to a chemical or an electrical signal.

The methods may include at least a portion of the MWNTs are doped with a cladding. The cladding can include a dielectric, an ion conducting polymer, an electron conducting polymer, an ionophore polymer dopant, a redox-mediator dopant, or any combination thereof. The dielectric can include a polyolefin polymer, a polyaliphatic polymer, a polysiloxane polymer, a polyurethane polymer, a polyvinylchloride polymer, alumina, or any combination thereof. Ion conducting polymer can include nafion, polystyrene sulfonate, polyvinylpridinium, or any combination thereof. Electron conducting polymer can include a doped polymer, an electrochemically doped polymer, a redox electroactive polymer, or any combination thereof. The doped polymer can include a polyionine, a polysilicon, a polysemicarbazole, a polyphenylene, a polyacetylene, a polyphenylene sulfide, or any combination thereof. The doped polymer can include a dopant, the dopant comprising AsF5, I2, Li, K, BF6-, PF6-, or any combination thereof. The electrochemically doped polymer can include a polypyrrole, a polythiophene, a polyphenylquinone, a polyaniline, or any combination thereof. The redox electroactive polymers can include polyviologen, polyvinylferrocene, poly-Ru(vbpy)3++, or any combination thereof. The ionophore polymer dopant can include a crown ether, a cryptand, a sphereand, a rotaxane, an antibiotic, a non-cyclic ligand, or any combination thereof. The redox-mediator dopant can include Ru(bpy)3++, Br2/Br-, Fe(phen)3+++, Co(terpy)2+++, Fe(CN)6(3-), Ru(NH3)6+++, quinone, hydroquinone, methylviologen, tetracyanoquinodimethane, benzophenone, ferrocene, tetramethyl-p-phenylenediamine, tetrathiafulvalene, tri-N-p-tolylamine, or any combination thereof.

The methods may include cladding that comprises one or more functional reactive groups residing upon a surface of the cladding. The functional reactive groups can include an oxide, a hydroxide, a carboxylic acid, an ester, an ether, a carbonyl, an amine, an amide, an epoxide, a halide, or any combination thereof. The cladding can include a covalent bond linkage attaching the cladding to the doped MWNTs. The covalent bond linkage can include a Schiff base, a carbodi-imide, an amide, or any combination thereof. The cladding can be linked to a selective functionality on the surface of one or more of the MWNTs. The selective functionality on the surface of one or more of the MWNTs can include a protein, a phospholipids, a nucleic acid, an electron mediator, an ionophore, or any combination thereof. The protein can include an enzyme, an antibody, or any combination thereof. The nucleic acid can include an oligonucleotide, DNA, RNA, or any combination thereof.

The methods may also include at least two of the doped MWNTs comprise different claddings. The methods may include at least a portion of the MWNTs being doped with a functional dopant molecule. The MWNTs may comprise one or more functional dopant molecules covalently attached to the graphene surface of the MWNTs. The functional dopant molecules may include an oxide, a hydroxide, a carboxylic acid, an ester, an ether, a carbonyl, an amine, an amide, an epoxide, a halide, or any combination thereof. At least a portion of the MWNTs may be doped with a covalent bond linkage that is covalently linked to the graphene surface of the MWNT. The covalent bond linkage may include a Schiff base, a carbodi-imide, an amide, or any combination thereof. The functional dopant molecules may be covalently attached to the graphene surface using a selective functionality. The selective functionality may include a protein, a phospholipids, a nucleic acid, an electron mediator, an ionophore, or any combination thereof. The protein may include an enzyme, an antibody, or any combination thereof. The nucleic acid may include an oligonucleotide, DNA, RNA, or any combination thereof.

The methods may include the electrically conductive layer comprises a metal, an electrically conductive polymer, a carbon film, or any combination thereof. The electrically conductive layer may be capable of being a lead conductor residing between the substrate and a catalyst surmounted to the electrically conductive layer. The electrically conductive layer may comprise Pt, Au, Ti, W, V, Mo, or any combination thereof. The metal may comprise a CVD-deposited metal. The CVD-deposited metal may comprise TiW, Mo, TiN, or any combination thereof. The electrically conductive layer can have a layer thickness in the range of from about 1 nanometer to about 1000 nanometers, in the range of from about 10 nanometers to about 100 nanometers, or in the range of from about 50 nanometers to about 100 nanometers. The catalyst can comprise Fe, Co, Ni, Mo, Ru, Pt, Cr, Pd, Pd, Si, Tb, Se, Cu, Al, Rh, Os, Ir, or any combination or alloy thereof. The catalyst can comprise Pd powder, Ni silicide, Fe—Ni alloy, Fe—Ni—Cr alloy, Mo—Fe alloy film, Fe—Tb alloy, Pd—Se alloy, Cu—Ni alloy, Co—Cu alloy, Al—Fe alloy, Cu—Fe alloy, Fe—Ni alloy, Alumina-Ni alloy, Alumina-Ni—Cu alloy, or any combination thereof. The catalyst can comprise an organo-metallic catalyst, an iron-phthalocyanine, a cobalt-phthalocyanine, or any combination thereof. The catalyst is usually capable of growing MWNTs. The catalysts capable of growing MWNTs includes nickel, cobalt, iron, or any combination thereof. The catalyst is characterized as having a layer thickness in the range of from about 1 nanometer to about 10,000 nanometers, in the range of from about 500 nanometers to about 1000 nanometers, or in the range of from about 700 nanometers to about 900 nanometers.

The methods may include a doped MWNT assembly comprising a plurality of doped MWNTs perpendicularly oriented to the substrate. The doped MWNTs can be oriented parallel to each other. The assembly of doped MWNTs can comprise a doped MWNT carpet, a doped MWNT array, or any combination thereof. The electrically conductive layer can comprise a single contiguous conductive layer, and the doped MWNT carpet is in electrical communication with the single contiguous conductive layer. The doped MWNT array can comprise an aligned array of nanotubes of a defined geometry and pitch oriented with respect to the electrically conductive layer. The assembly of doped MWNTs can comprise an array of doped MWNTs. The catalyst can patterned on the electrically conductive layer, and the assembly of doped MWNTs can be attached to the patterned catalyst. The catalyst can be patterned as an array of islands, stripes, circles, squares, rings, triangles, polygons, or any combination thereof.

Antennae assembly field-effect transistors can include a substrate comprising a source and a drain; a gate oxide layer at least partially surmounting the substrate, source and drain; an electrically conductive layer at least partially surmounting the gate oxide layer; and an assembly of doped MWNTs vertically oriented with respect to the electrically conductive layer.

Sensors can include at least two electrodes situated on a substrate, wherein at least one of the electrodes comprises a doped antennae assembly electrode, the doped antennae assembly electrode comprising an electrically conductive layer at least partially surmounting the substrate; and an assembly of doped MWNTs vertically oriented with respect to the electrically conductive layer to provide the doped antennae assembly electrode. The sensors can include electrodes that include at least one working electrode and at least one reference electrode. Sensors can have at least one working electrode comprises a doped antennae assembly electrode. Sensors can have at least one reference electrode comprises a doped antennae assembly electrode. At least one working electrode and at least one reference electrode can comprise a doped antennae assembly electrode. The reference electrode can be situated on a field-effect transistor. A field-effect transistor can comprises a source and a drain, the source and drain being electrically connected by conductive leads to electrical contacts situated on the substrate. Sensors can include field-effect transistors that comprises: a gate oxide layer at least partially surmounting the substrate, source and drain; the electrically conductive layer at least partially surmounting the gate oxide layer; and having the assembly of doped MWNTs vertically oriented with respect to the electrically conductive layer. Sensors may further comprise a counter electrode. Sensors may further comprise a counter electrode comprises a doped antennae assembly electrode, a metallic electrode, or any combination thereof. Sensors may further comprise a metallic electrode that is composed of gold, silver, platinum, palladium, copper, iron, titanium, tungsten, or any combination thereof. Sensors may further comprise electrically conducting leads connecting each of the electrodes to an electrical contact situated on the substrate.

Patterned Growth of ACNTs by Solid Precursor Assisted CVD

In these examples a fabrication process is provided to grow carbon nanotube selectively in a chemical vapor deposition using an organic-metallic precursor Iron (II) Phthalocyanine as a catalyst and a carbon source on a given substrate. The process of chemical vapor deposition (CVD) involves the transformation of gaseous molecules into solid material on the surface of the substrate. Metals, alloys, or polymeric films can be deposited by the chemical vapor deposition method and thus ideal for thermal growth of carbon nanotubes. A one step method is provided to prepare a well aligned carbon nanotube array which utilizes an organo-metallic precursor which serves as the source of carbon as well as the metal catalyst. This example shows that MWNTs do not grow on copper surfaces. This example provides a fabrication method to pattern copper on a substrate, which method selectively controls the growth of the nanotubes. A fabrication method is provided for depositing copper to prevent growth of carbon nanotubes generated by pyrolysis of Iron (II) Phthalocyanine. A fabrication method is provided for patterning copper to selectively grow aligned carbon nanotubes generated by pyrolysis of Iron (II) Phthalocyanine.

Figure 14A:
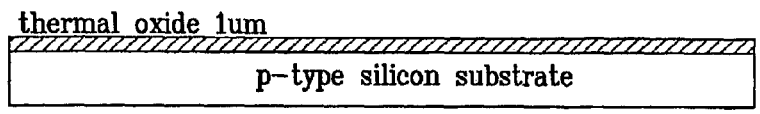
FIGS. 14A-H show a fabrication process of catalyst insulation and mechanical support.
Figure 14B:
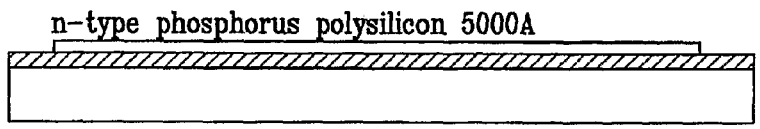
Figure 14C:
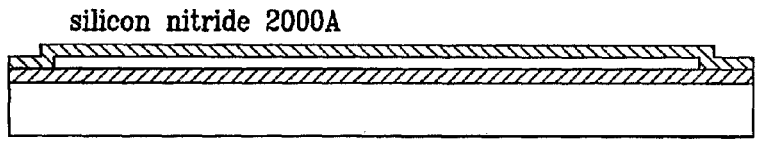
Figure 14D:
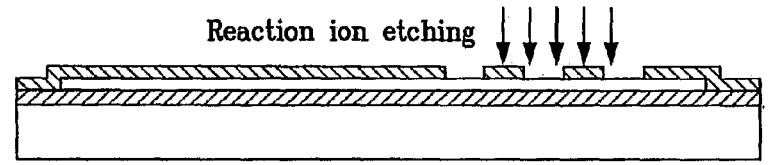
Figure 14E:
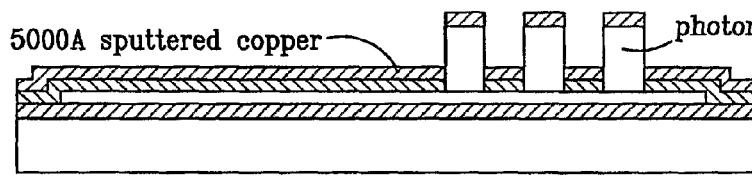
Figure 14F:
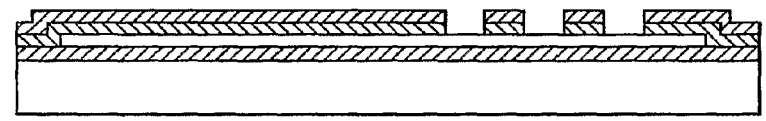
Figure 14G:
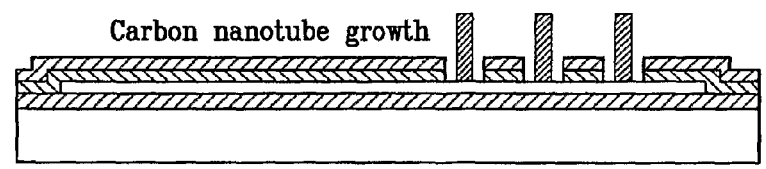
Figure 14H:
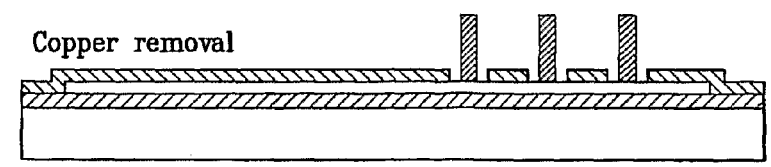

In this example, the process starts with a 100 mm p-type silicon wafer with a 1 um thick thermal oxide (FIG. 14A). A 2500A of polysilicon layer is deposited at 600 C. following by a phosphorus implantation (dose=1E16 J/cm2, energy=100 keV, 7° tilt), and another 2500A of polysilicon layer deposition. The dopant is activated at 1000 C. for one hour. The annealed polysilicon should have resistivity of 20-25 ohms/ square. The polysilicon (FIG. 14B) is patterned using standard lithography technique and etched by reactive ion etching to form the sensing electrode. Next, a 2000A thick layer of silicon nitride (FIG. 14C) is deposited by low pressure chemical vapor deposition acting as an insulating material. Access holes are patterned and opened by reactive ion etching of silicon nitride (FIG. 14D). A 5000A thick copper layer (FIG. 14E) is sputtered and is patterned by the reverse mask of the previous access hole patterns. Copper is then lifted off by soaking into acetone (FIG. 14F). At this point, the sample surface essentially has two types of surface: 1) the conductive polysilicon electrode, and 2) copper masking layer.

Figure 14I:
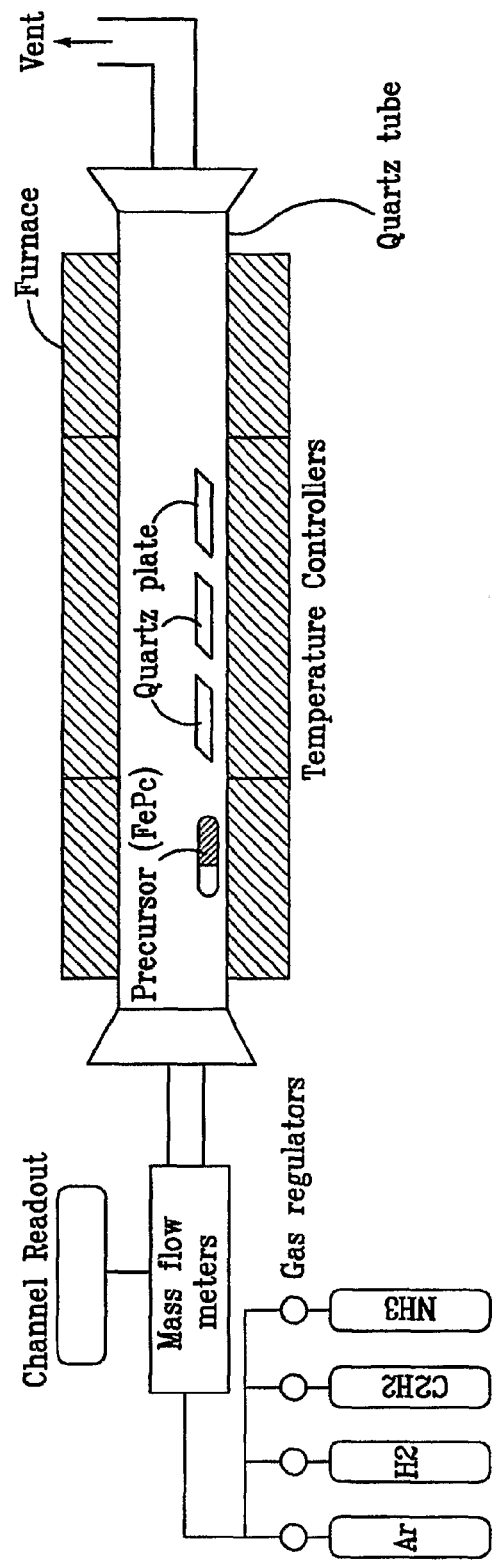
FIG. 14I setup for thermal chemical vapor deposition
Figure 14J:
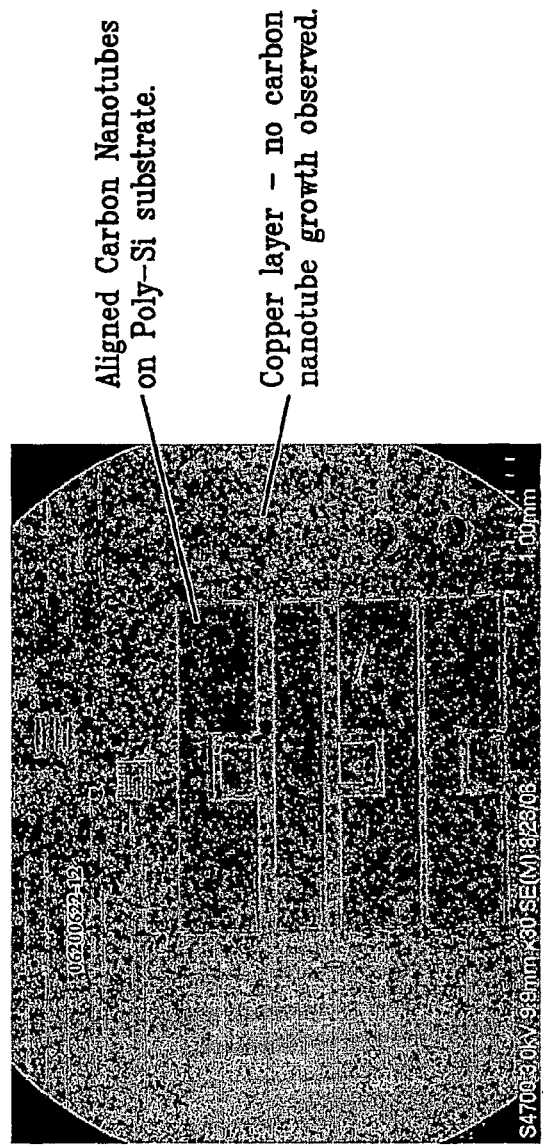
FIG. 14J shows aligned multiewalled carbon nanotubes (ACNTs) grown on Patterned Chip with growth conditions; Ar/$H_2$/Temp/FePc/Time:80/75/902/0.6/5 min.
Figure 14K:
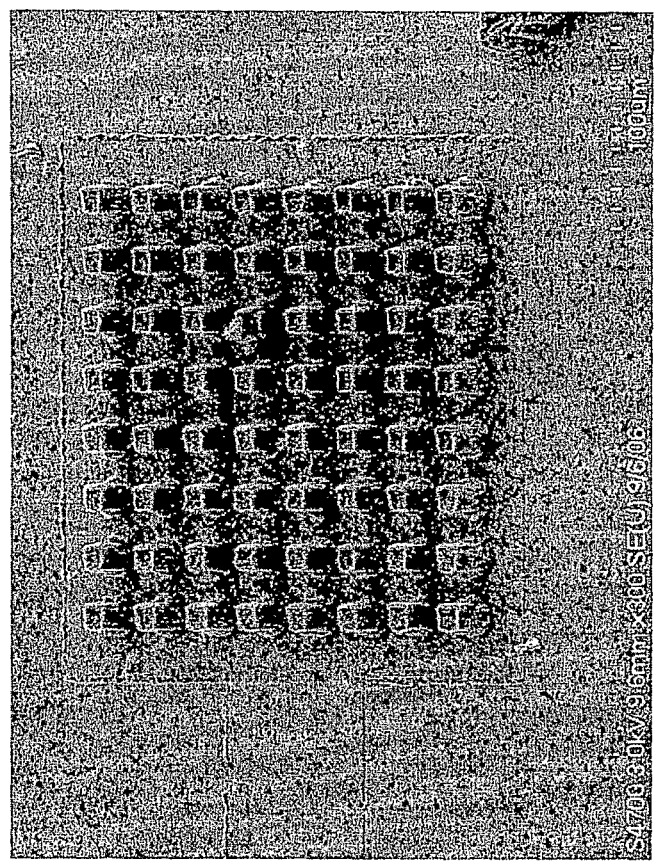
FIG. 14K shows ACNTs grown on Patterned Chip with growth conditions; Ar/$H_2$/Temp/FePc/Time:20/20/902/0.4/20 min.
Figure 14C:
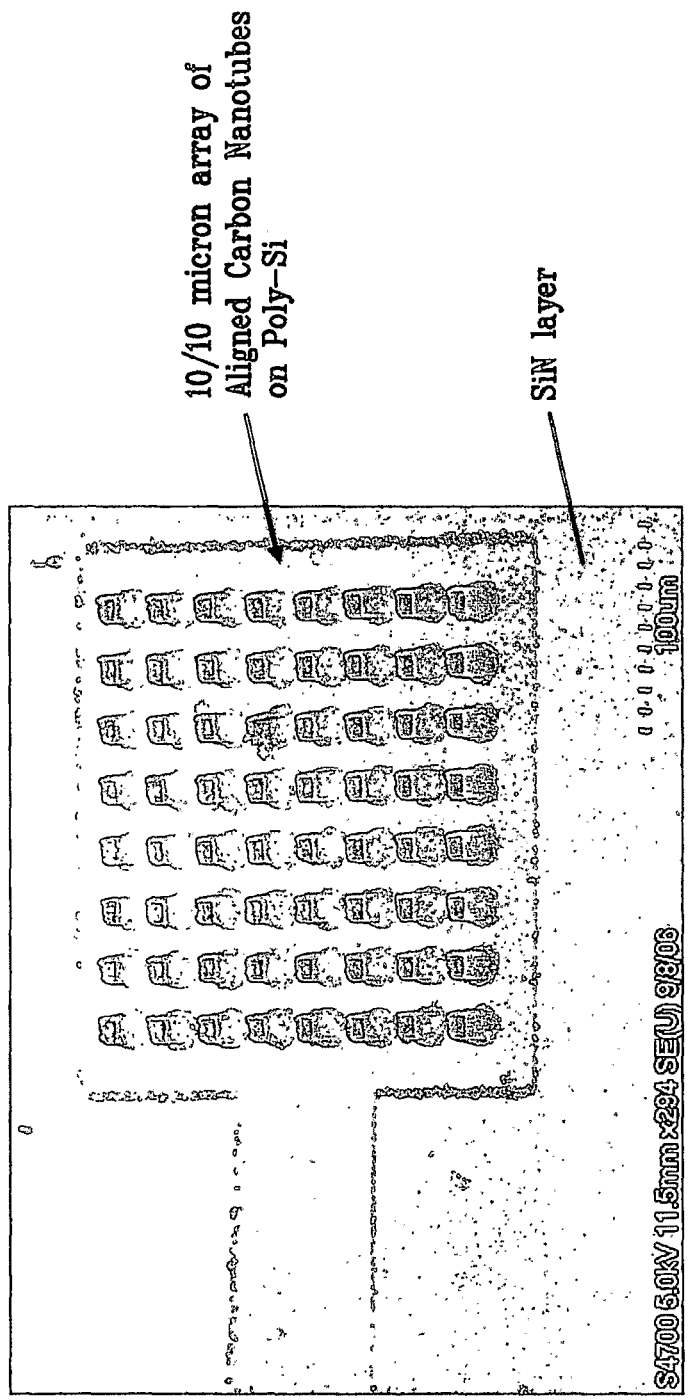
Figure 14M:
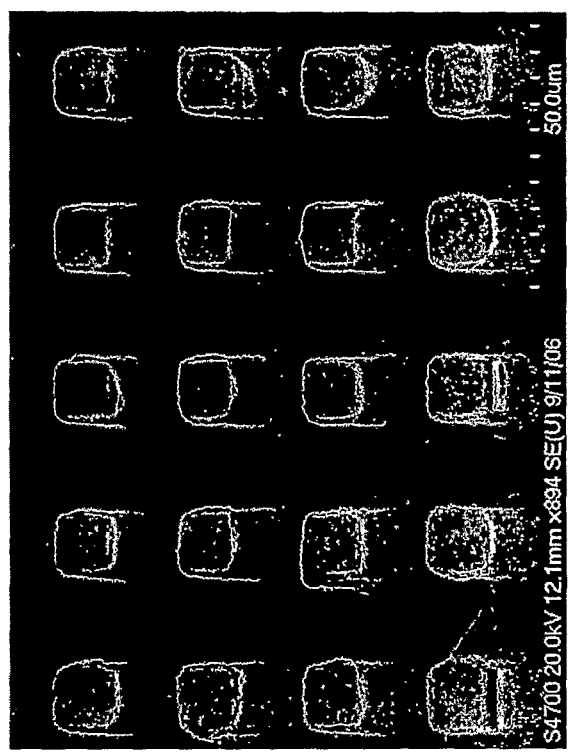
FIG. 14M shows ACNTs grown on Patterned Chip with growth conditions; Ar/H$_2$/Temp/FePc/Time:20/20/902/0.4/20 min. And post-clean up process carried out to remove the sacrificial Copper layer.
Figure 15A:
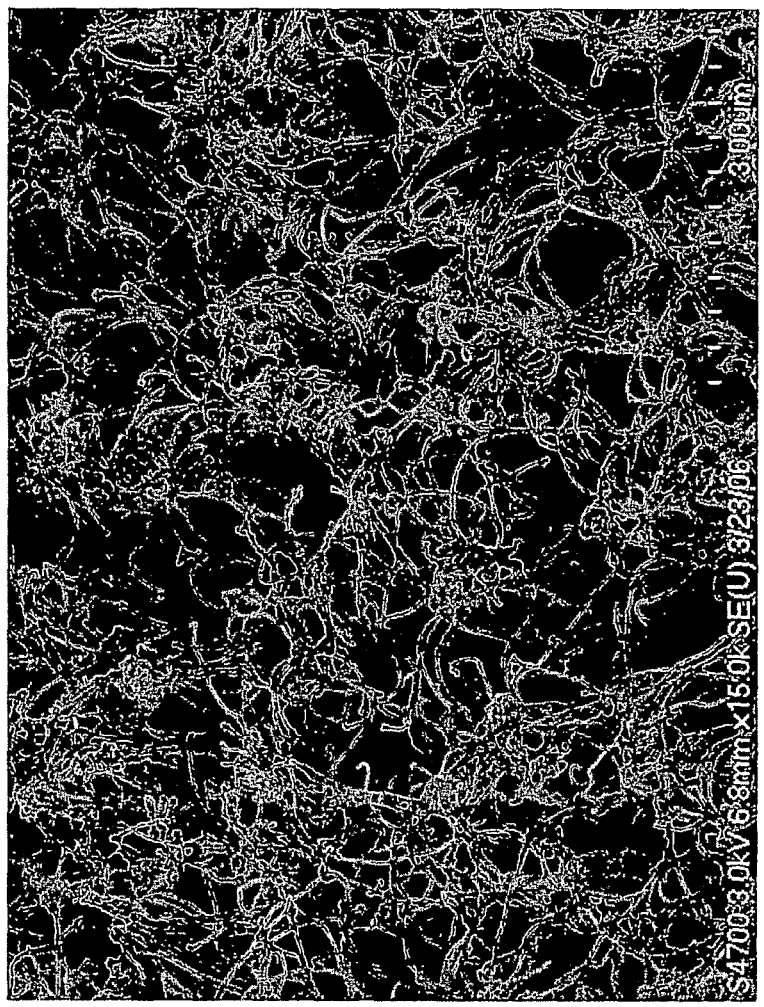
FIG. 15A shows Non-aligned multiwalled CNTs grown on 30 nm Ni on Poly-silicon with gas ratio of Ar/H$_2$/C$_2$H$_2$: 100/20/15 sccm at 745° C.
Figure 15B:
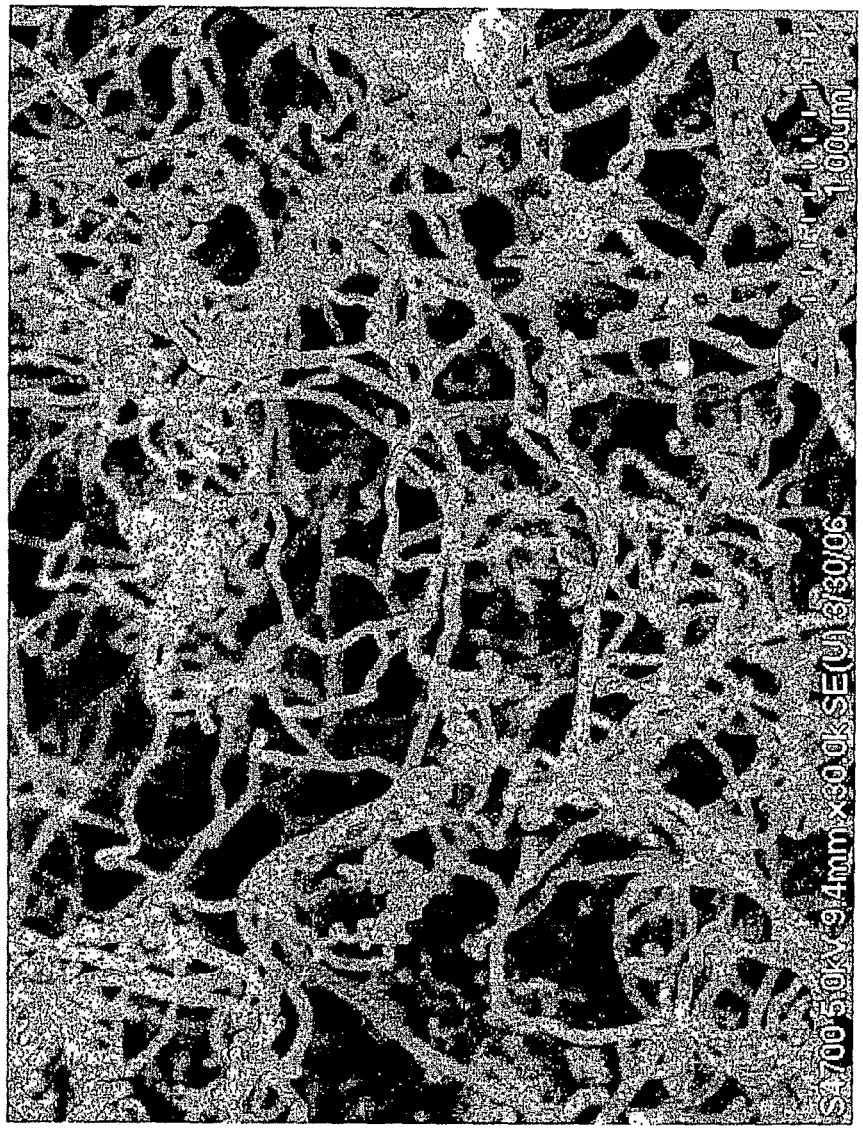
FIG. 15B shows Non-aligned multiwalled CNTs grown on 30 nm Ni on P-type silicon with gas ratio of Ar/H$_2$/C$_2$H$_2$; 100/20/15 sccm at 745° C.
Figure 15C:
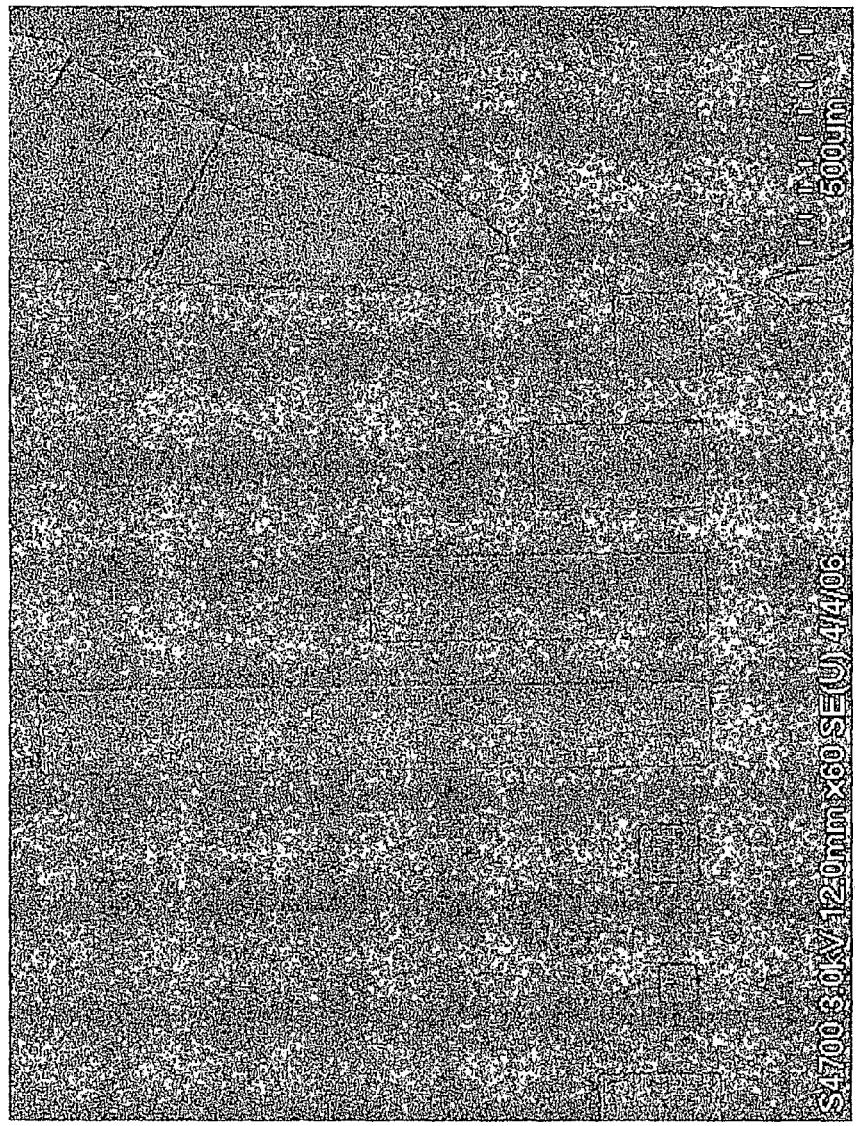
FIG. 15C shows Non-aligned patterned CNTs grown on 60 nm Ni on cracked Poly-silicon with gas ratio of Ar/H$_2$/C$_2$H$_2$; 100/20/15 at 745° C.
Figure 15D:
FIG. 15D shows aligned multiwalled CNTs carpet (approximately 10 micron long) grown on Poly Si/Ti 50 nm/Ni 30 nm (sample was annealed at 400° C. for 15 hours) with gas ratio of Ar/H$_2$/C$_2$H$_2$; 100/20/15 sccm at 745° C.
Figure 15E:
FIG. 15E shows aligned multiwalled CNTs carpet (approximately 35 micron long) grown on Poly Si/Ti 50 nm/Ni 30 nm (sample was annealed at 400° C. for 15 hours) with gas ratio of Ar/H$_2$/C$_2$H$_2$; 80/75/15 sccm at 745° C.
Figure 15F:
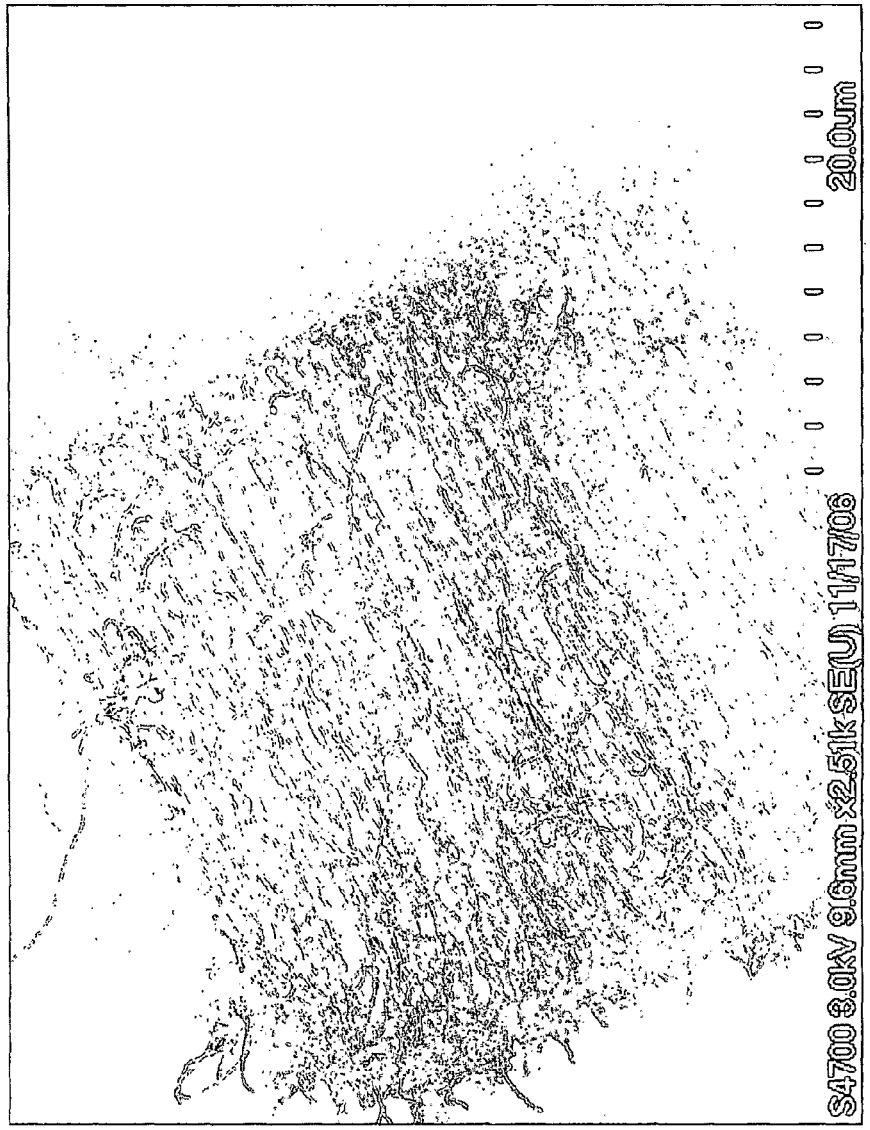
FIG. 15F shows 35 micron long ACNTs bundle scratch off from the substrate. Growth conditions same as described in Figure (d).
Figure 15G:
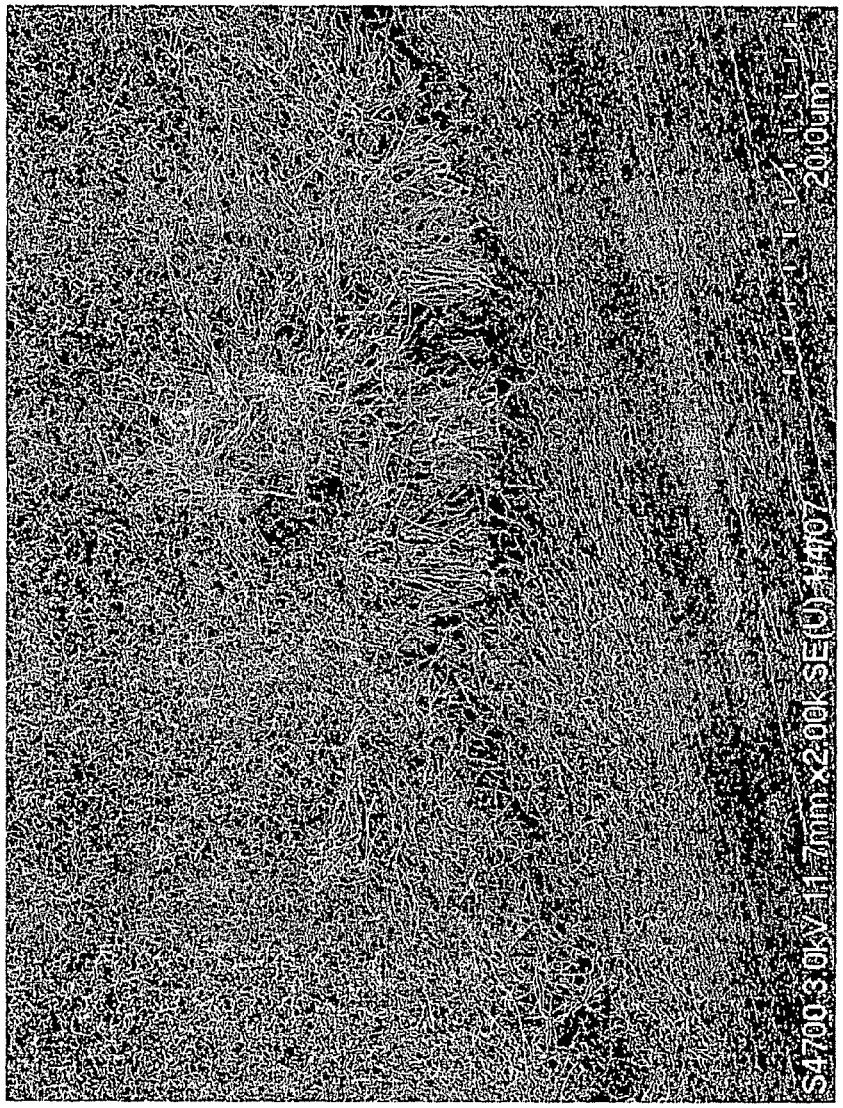
FIG. 15G shows aligned multiwalled CNTs carpet grown on Poly Si/Ti 50 nm/Ni 30 nm (substrate was annealed at 400° C. for 15 hours) with gas ratio of H$_2$/C$_2$H$_2$; 155/15 at 745° C.
Figure 15H:
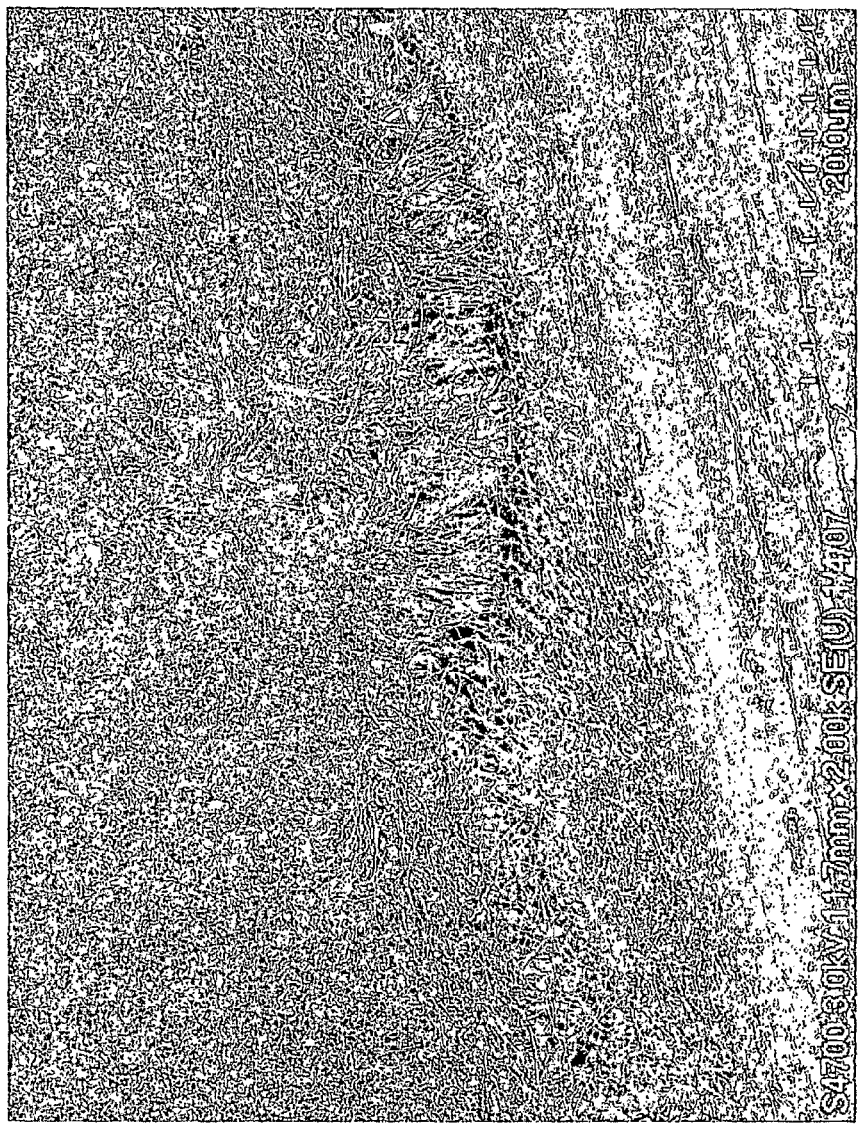
FIG. 15H C shows aligned multiwalled CNTs carpet grown on Poly Si/Ti 50 nm/Ni 30 nm (sample was annealed at 400° C. for 15 hours) with gas ratio of Ar/NH$_3$/C$_2$H$_2$; 250/150/25 sccm at 745° C.
Figure 15I:
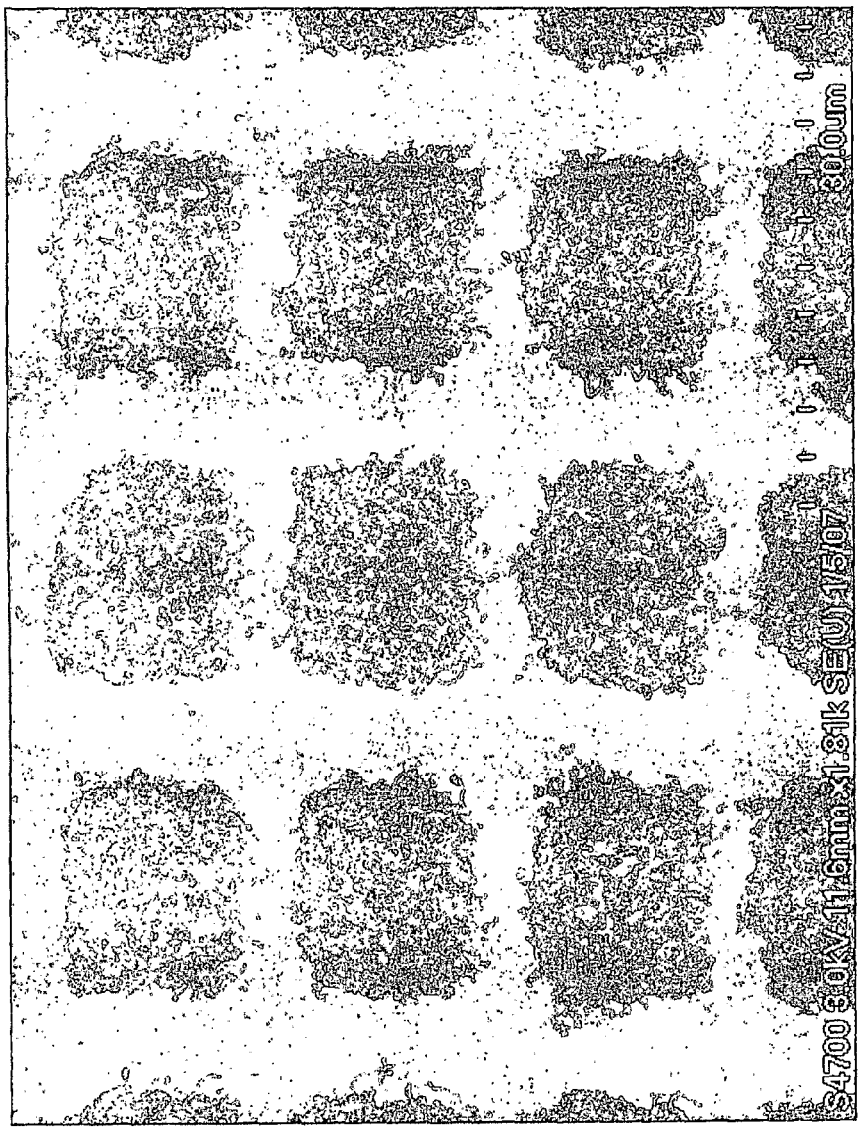
FIG. 15I shows aligned patterned CNTs grown on 30 nm Ni on 50 nm Ti on Poly-silicon (patterned sample was annealed at 400° C. for 15 hours) with gas ratio of Ar/H$_2$/C$_2$H$_2$; 30/125/20 sccm at 745° C.
Figure 15J:
FIG. 15J shows TEM image of multiwalled CNTs grown on 30 nm Ni on Poly-silicon with gas ratio of Ar/H$_2$/C$_2$H$_2$: 100/20/15 sccm at 745° C.
Figure 15K:
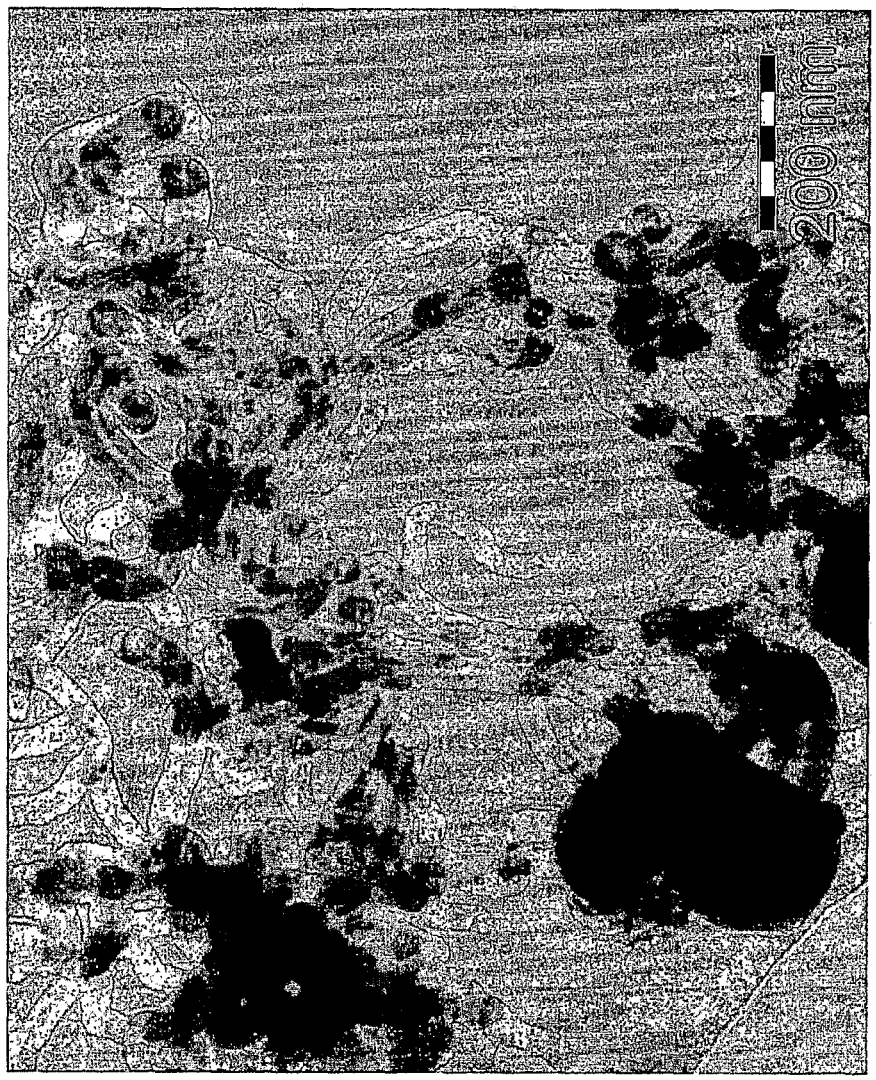
FIG. 15K shows TEM image of multiwalled CNTs grown on 30 nm Ni on P-type silicon with gas ratio of Ar/H$_2$/C$_2$H$_2$; 100/20/15 sccm at 745° C.
Figure 15L:
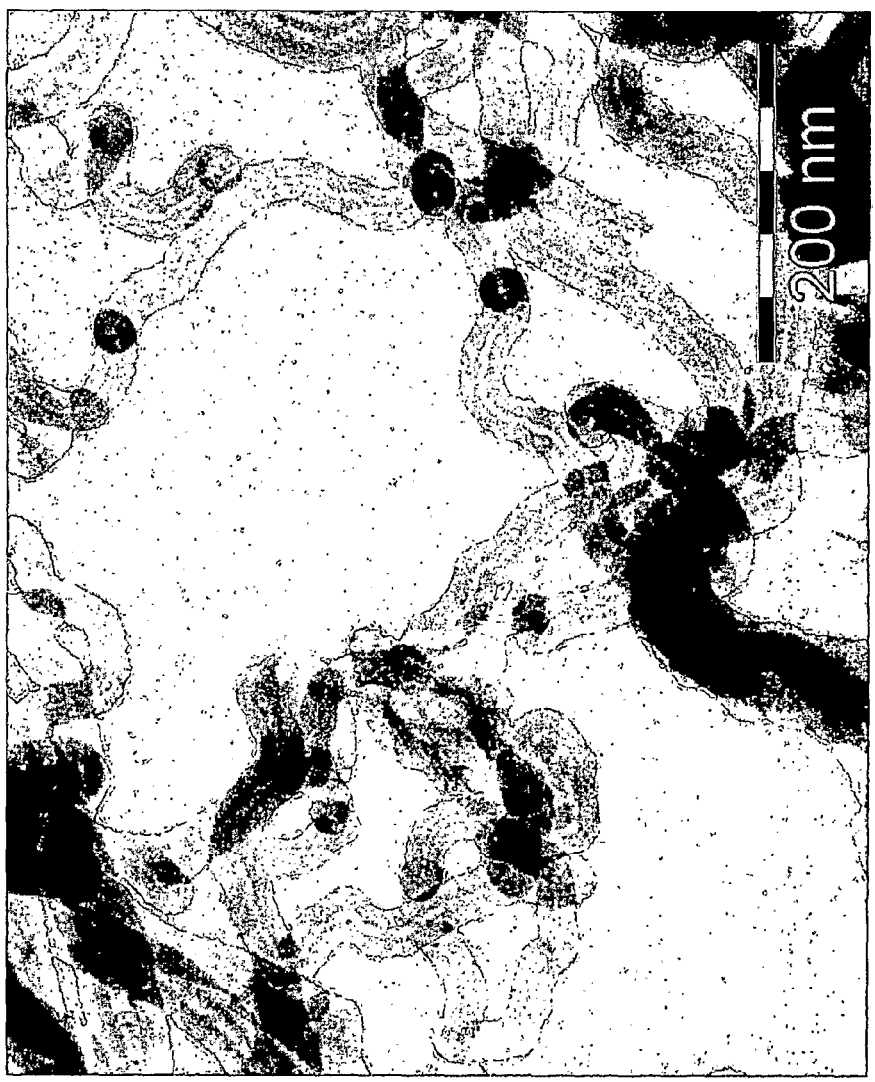
FIG. 15L shows TEM image of patterned CNTs grown on 60 nm Ni on cracked Poly-silicon with gas ratio of Ar/H$_2$/C$_2$H$_2$; 100/20/15 at 745° C.
Figure 15M:
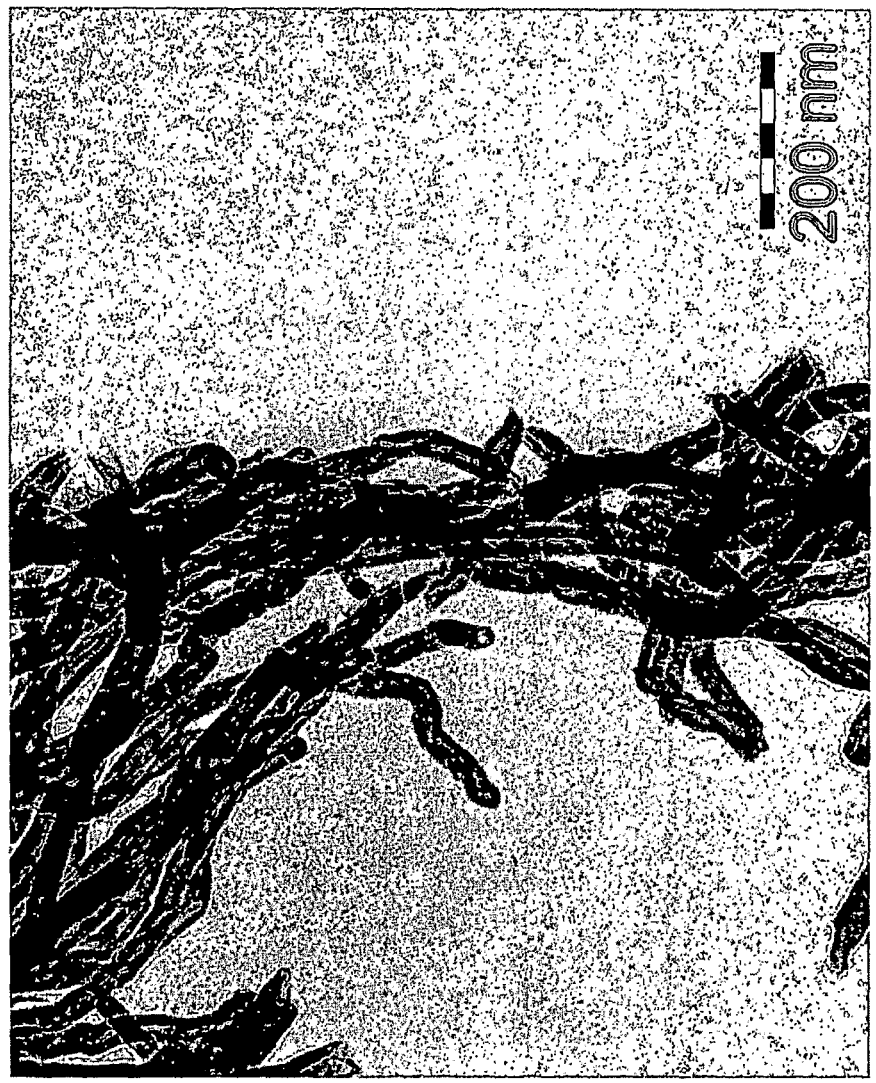
FIG. 15M shows TEM image of multiwalled CNTs carpet grown on Poly Si/Ti 50 nm/Ni 30 nm (sample was annealed at 400° C. for 15 hours) with gas ratio of Ar/H$_2$/C$_2$H$_2$; 100/20/15 sccm at 745°.
Figure 16A:
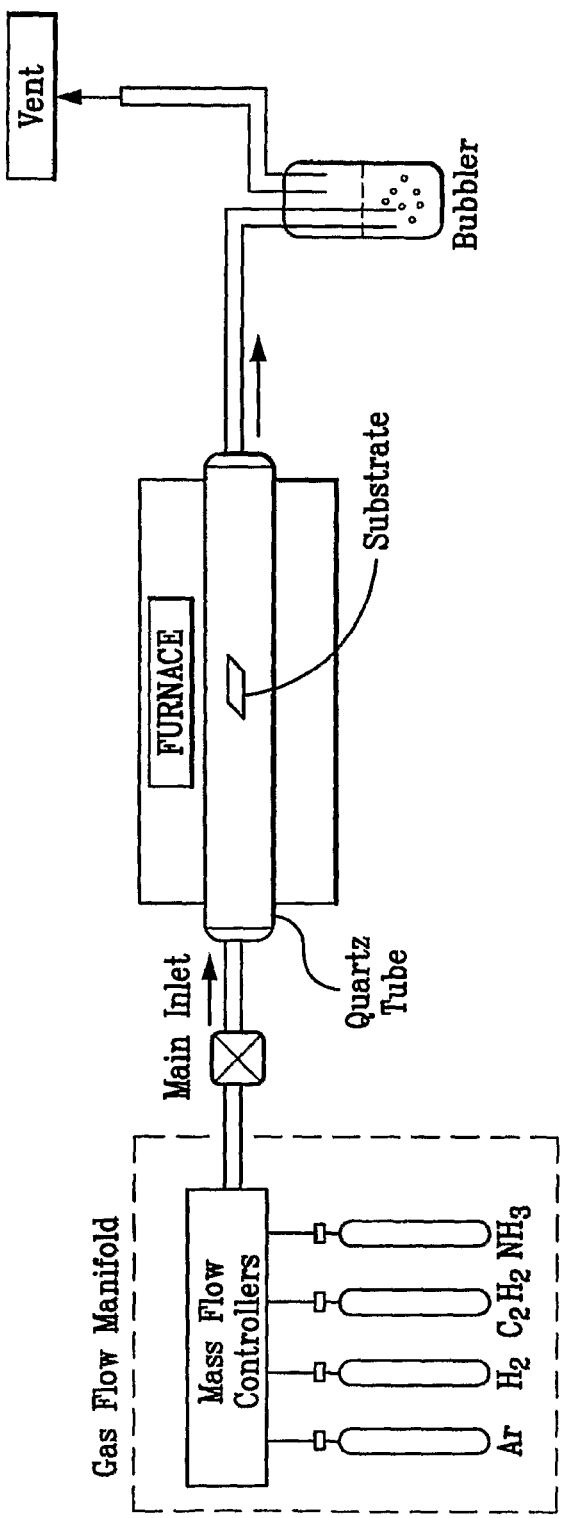
FIG. 16A shows a setup for thermal chemical vapor deposition.
Figure 16B:
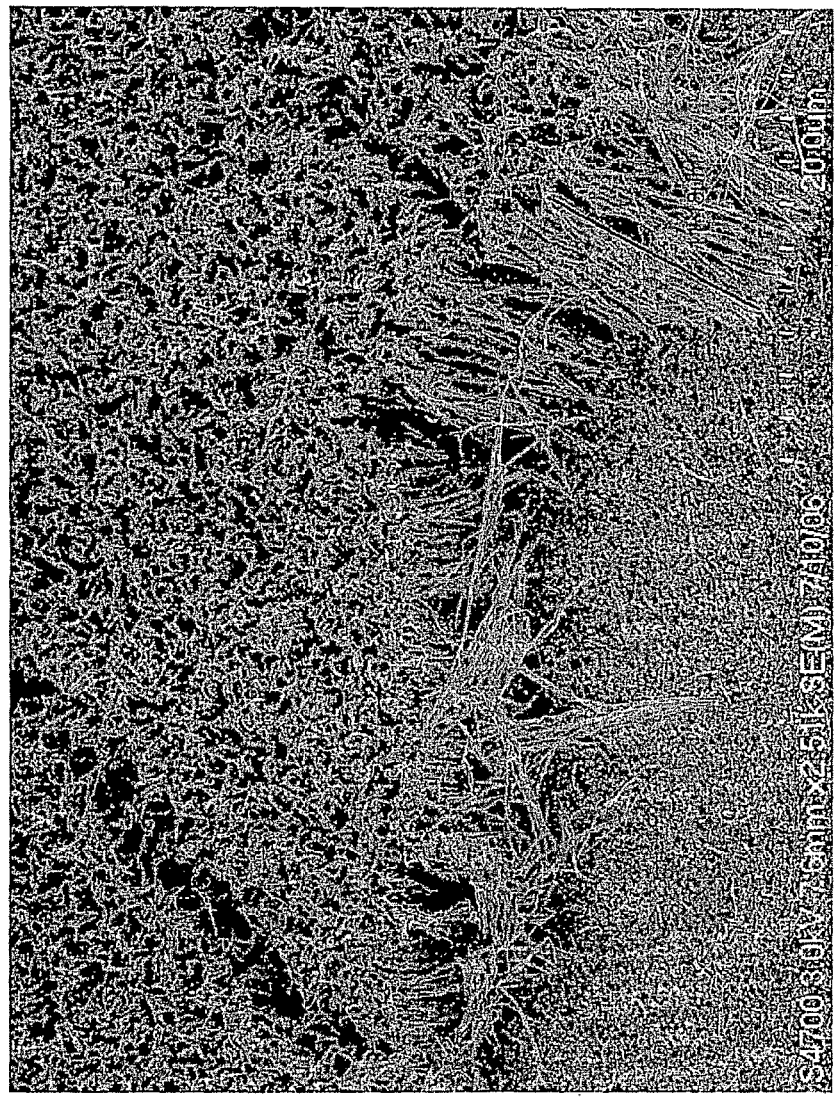
FIG. 16B shows ACNTs grown on P-type Si with growth conditions; Ar/H$_2$/Temp/FePc/Time:40/75/902/0.6/8 min.
Figure 16C:
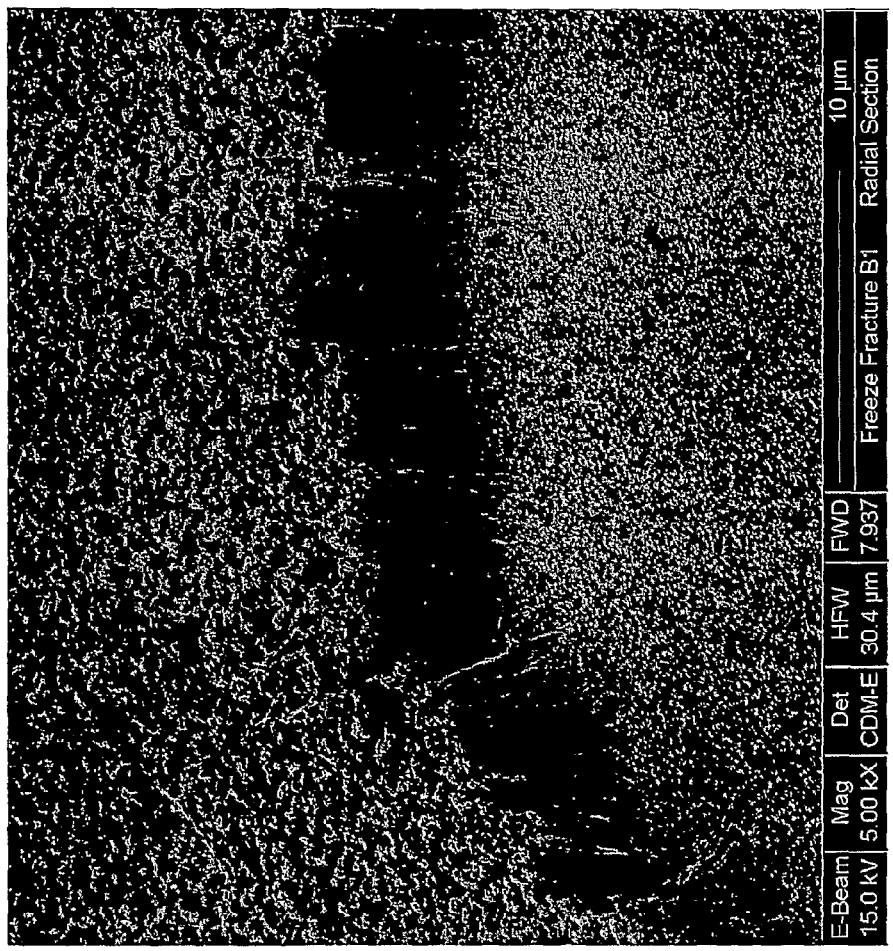
FIG. 16C shows ACNTs grown on Quartz with growth conditions; Ar/H$_2$/Temp/FePc/Time:20/20/902/0.4/20 min.
Figure 16D:
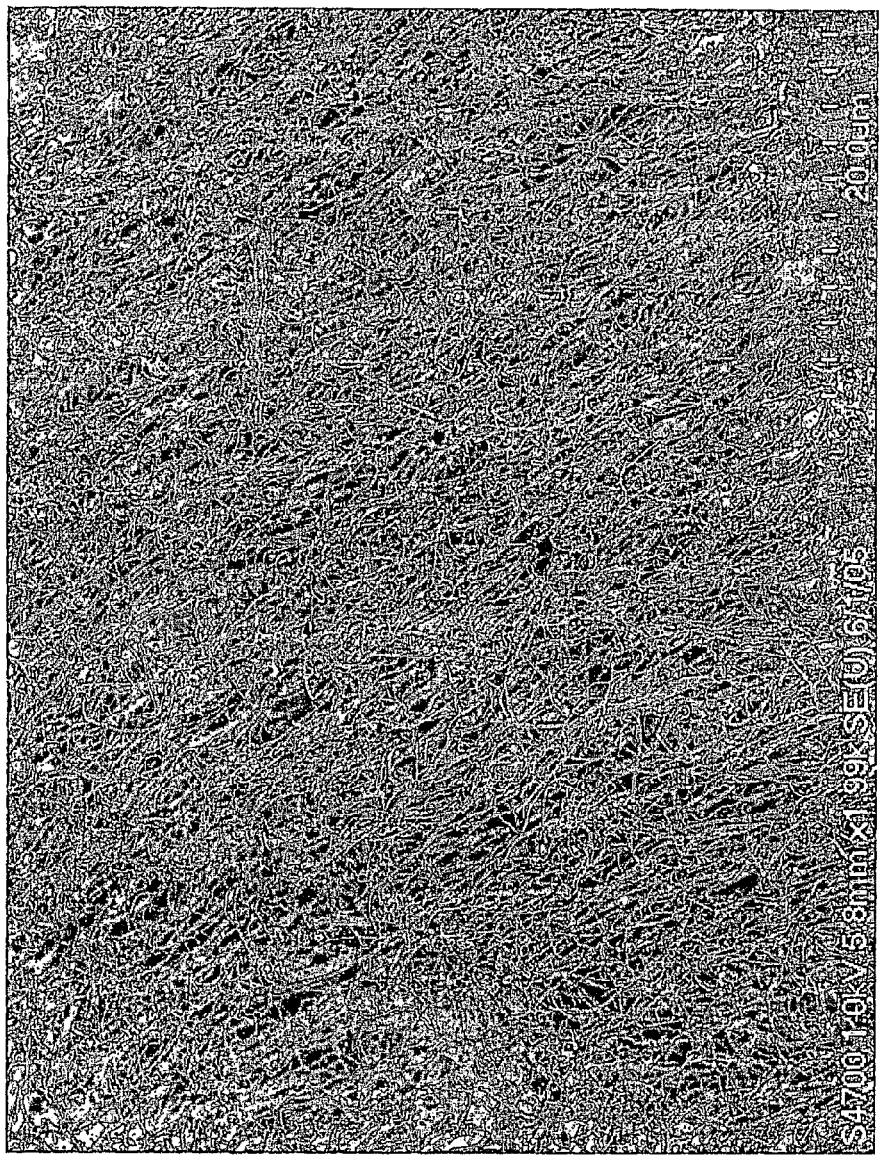
FIG. 16D shows ACNTs grown on SiOx with growth conditions; Ar/H$_2$/Temp/FePc/Time:40/110/902/0.3/10 min.
Figure 16E:
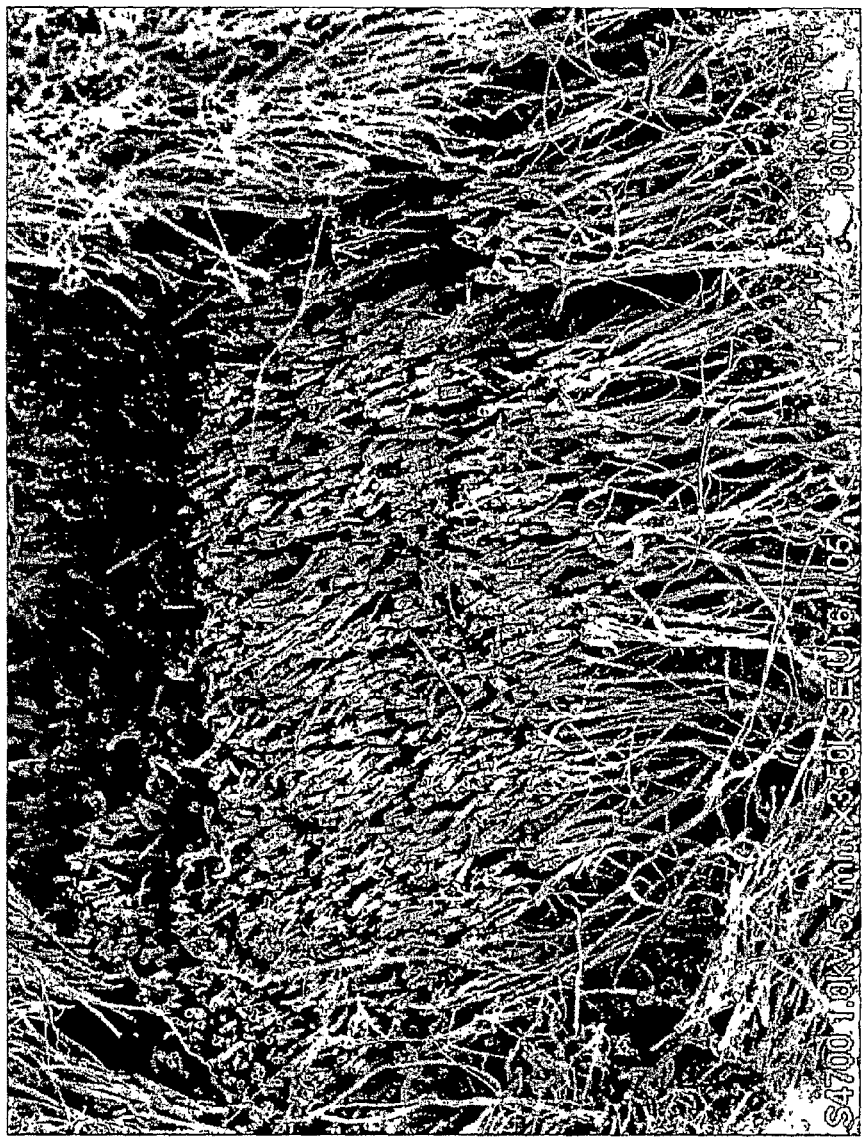
FIG. 16E shows ACNTs grown on SiN with growth conditions; Ar/H$_2$/Temp/FePc/Time:40/120/902/0.3/10 min.
Figure 16F:
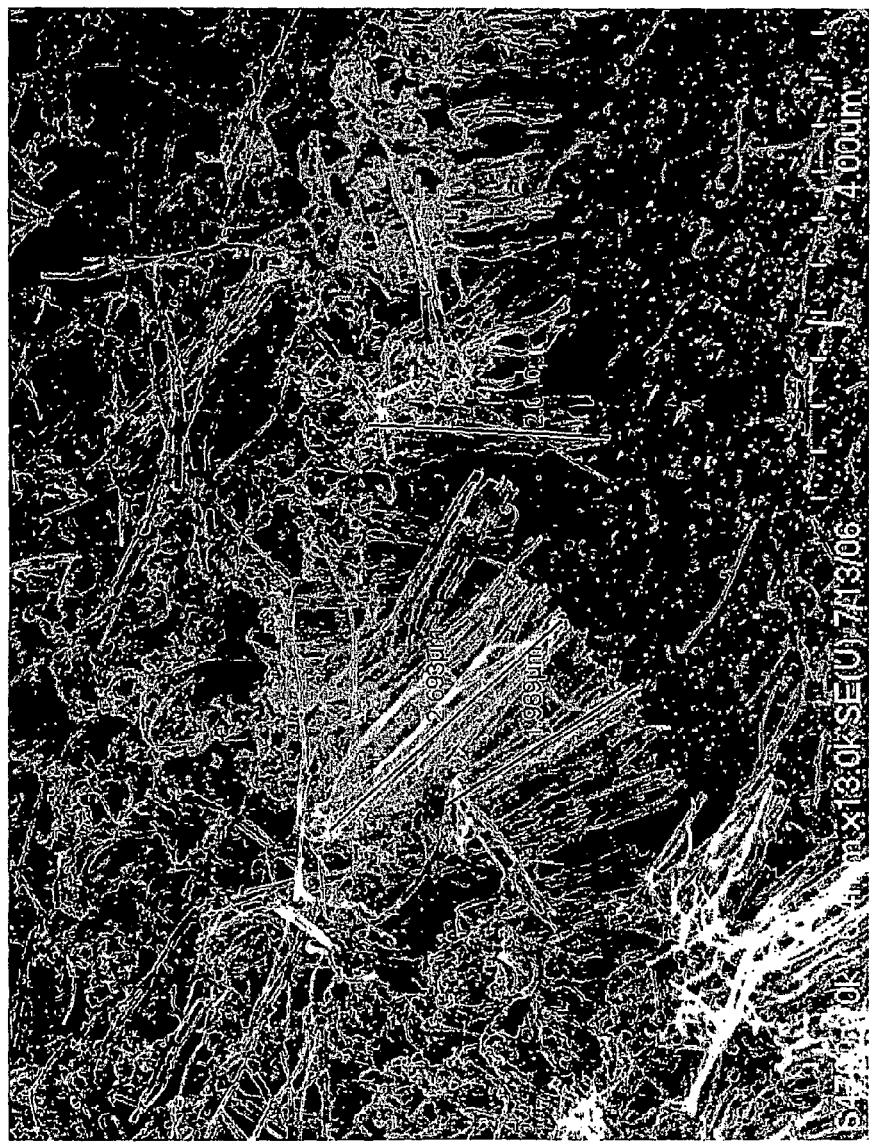
FIG. 16F shows ACNTs grown on P-type Si with growth conditions; Ar/H$_2$/Temp/FePc/Time:80/150/820/0.6/6 min.
Figure 16G:
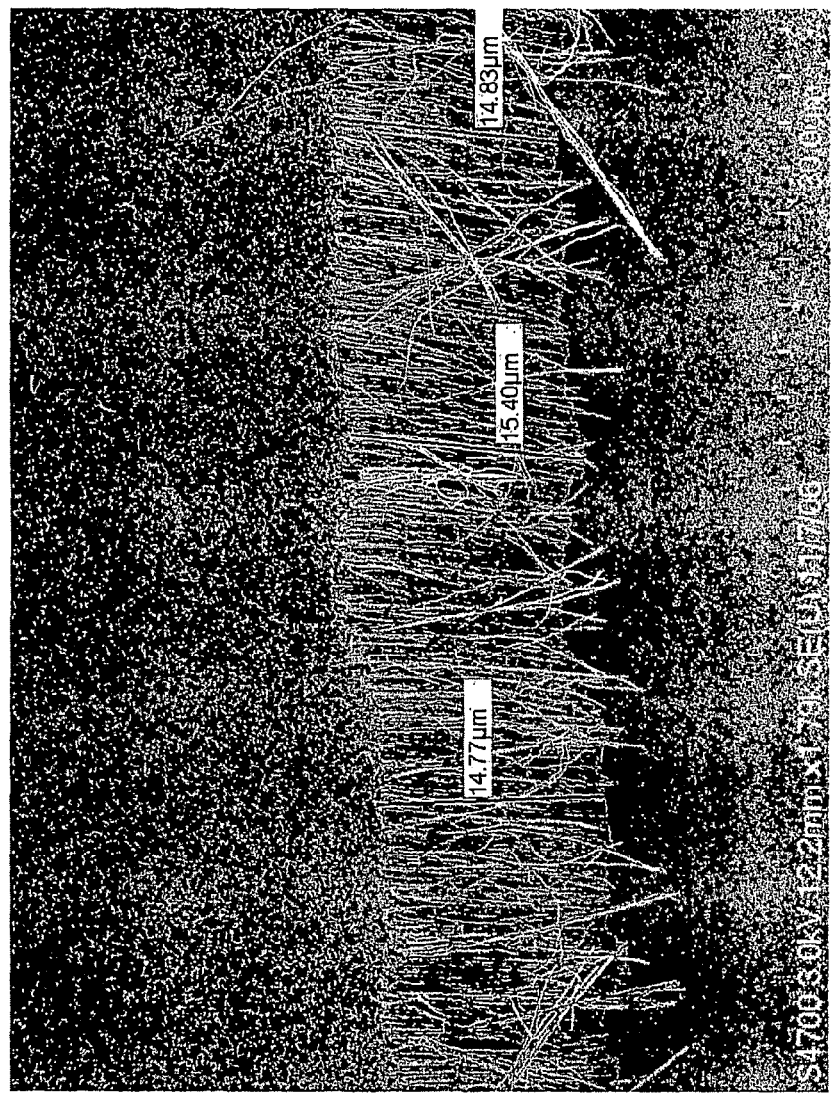
FIG. 16G shows Chip # SP457 ACNTs grown on P-type Si with growth conditions; Ar/H$_2$/Temp/FePc/Time:80/75/960/0.6/1.5 min.
Figure 16H:
FIG. 16H shows ACNTs grown on P-type Si with growth conditions; Ar/H$_2$/Temp/FePc/Time:100/100/900/0.4/5 min.
Figure 16I:
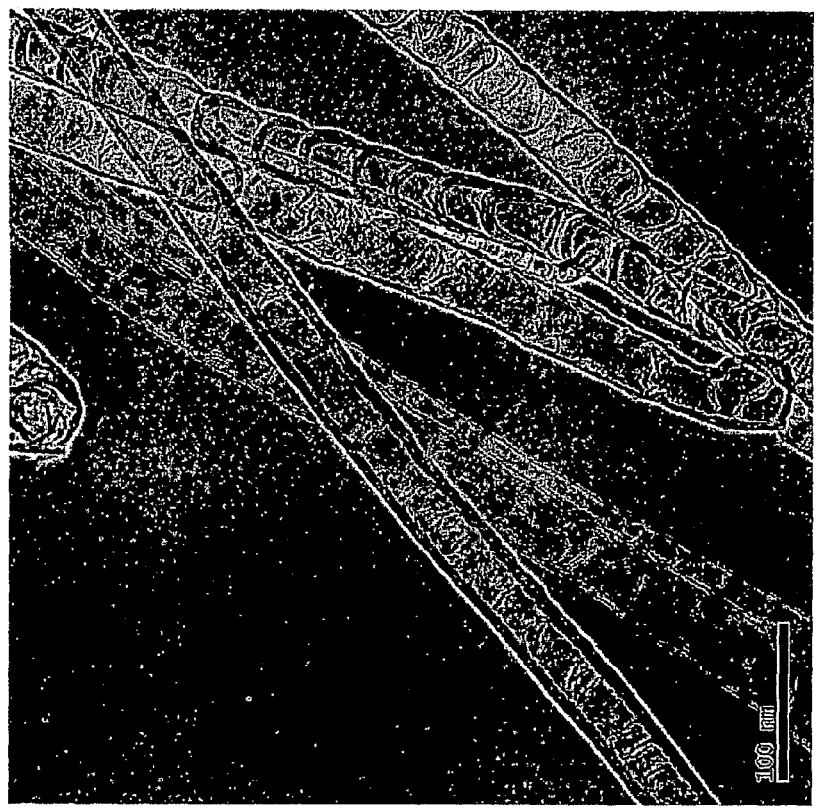
FIG. 16I shows a TEM image of multiwalled CNTs grown on SiOx with growth conditions; Ar/H$_2$/Temp/FePc/Time:15/20/900/0.5/10 min.
Figure 16J:
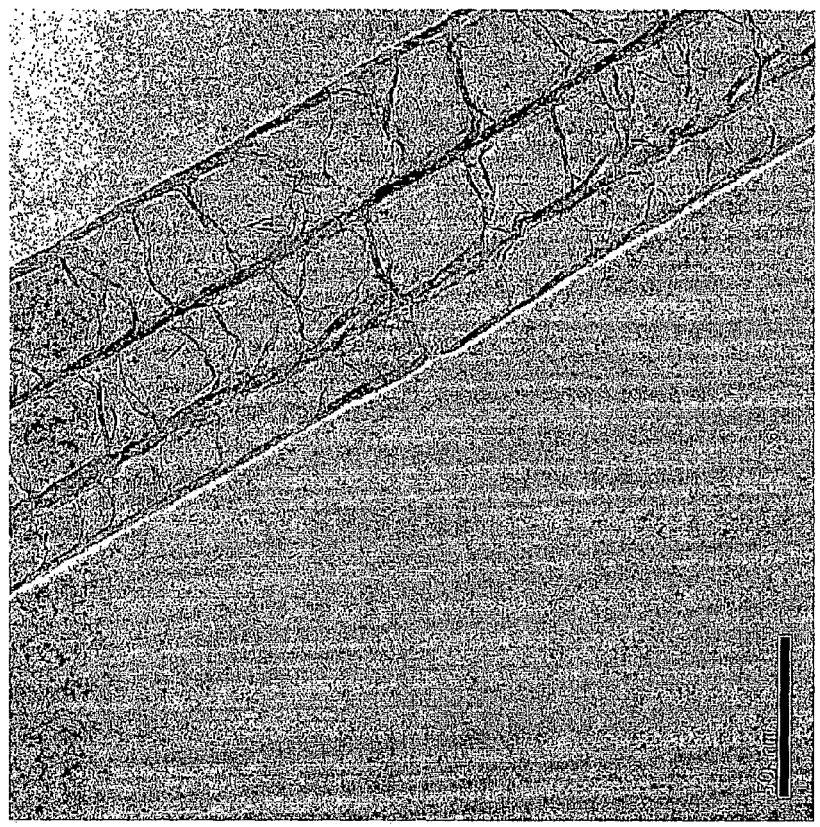
FIG. 16J shows a TEM image of multiwalled CNTs similar to those shown in FIGS. 16I and 16K.

ACNTs Growth Procedure:
1. The pre-patterned substrate is introduced into the flow reactor (quartz tube) (refer FIG. 14I).
2. Iron (II) Phthalocyanine (0.1-0.7 g) is placed in a quartz/ceramic boat and placed inside the quartz tube.
3. The system is sealed and flushed with Argon (Ar) (300-500 Sccm) for 20-30 minutes. This step removes any oxygen present in the quartz tube and provides an inert reaction atmosphere.
4. The temperature of the furnace is set at desired growth temperature which may range from 800-960° C. depending on the size, density and quality of ACNTs.
5. As the temperature of the system reaches 800° C. the flow rate of Ar is reduced to desired flow rate (10-150 Sccm) and $H_2$ is introduced in the gas flow at a desired flow rate (10-150 Sccm). Allow 10 minutes for the gases to mix uniformly inside the reactor.
6. The gas flow is maintained steady through out the growth process.
7. Pyrolysis of the Precursor: Once the furnace attains constant set temperature, the precursor boat is transferred in the temperature range (450-750° C.) where the pyrolysis of the organo-metallic precursor is triggered. Iron and carbon source is released into the gas phase and gets carried into the flow stream by Ar and $H_2$. (30 sec-2 min)
8. The carrier gas transports the metal/carbon into the high temperature zone where the growth of carbon nanotubes on the substrate takes place. (2-10 min)
9. After the reaction time, the furnace is shut-off, the $H_2$ flow is turned off, and only Ar gas flow is maintained steady at a low flow rate (300-500 Sccm).
10. Once the furnace temperature reaches a safe value and all the $H_2$ is flushed out of the reactor system, the quartz tube is opened and exposed to air.
11. The ACNT growth will take place only on chip area which is not covered with Copper.
12. The substrate is taken out of the tube and taken for Copper removal process.

post-Synthesis Clean up—Copper layer removal process:
1. After the synthesis of ACNTs on the patterned chip (CHEM Chip), the Cu-sacrificial 1 growth inhibiting layer has to be removed, without hindering the alignment and geometry of the carbon nanotubes.
2. Cu-removal solution: $H_2O$: $HCl$:$H_2O_2$ in the ratio of 20:0.4:0.2 v/v. Dip the ACNT coated CHEM Chip in Cu-removal solution with stirring for 5 min.
3. Remove the ACNT coated CHEM Chip from the Cu-removal solution and dip it in DI-$H_2O$ with stirring and allow to clean for 10 min.
4. After DI-$H_2O$ rinsing, dry the ACNT coated CHEM Chip in air.
5. The dry ACNT coated CHEM Chip is introduced into the RF Plasma Asher.
6. $O_2$ or $H_2O$ Plasma treatment is carried out to remove residual organic deposits present on the ACNT coated CHEM Chip. Plasma Conditions: Power 25-50 W; Pressure 0.9-0.08 mbarr; Time 30 sec-10 min. While this plasma etches away the amorphous carbon, it also attacks the nanotube to some degree. An alternative fabrication process could involve depositing an additional silicon dioxide layer underneath the copper sacrificial layer. The amorphous carbon could then be lifting off when the sample is soaking in hydrofluoric acid, while nanotubes remain unattacked.
7. After the Plasma Clean Up Process, inert SiN layer is exposed and the ACNT patterned chip is ready for further characterization and sensor development.

Growth of Aligned/Non-Aligned Carbon Nanotubes by Gas Phase Chemical Vapor Deposition Carbon nanotubes (CNTs) are synthesized in a thermal CVD system using Argon (Ar), Ammonia ($NH_3$)/Hydrogen ($H_2$) as the carrier gas mixture and Acetylene ($C_2H_2$) as the carbon source. Gas Phase CVD growth has been successfully established on Nickel metal catalyst and various substrates like Si, $SiO_2$, SiN, Poly Si (Phosphorus doped) and P-type Si (Boron Doped). The tubes grown are either aligned or not aligned depending on the process conditions a substrate preparation. The diameter of these nanotubes range from 10-40 nm with thick walls and narrow cores. The growth conditions govern the synthesis of predominantly bamboo structured tubes or mixture of bamboo and hollow tubes. This growth process is defined by the catalyst and was successfully transferred onto the patterned chip to yield clean and patterned carbon nanotube growth. Non-aligned CNTs were grown on these substrates at growth temperature of 650° C. to 750° C. Aligned CNTs are grown by adding Titanium (Ti) as the barrier layer in between the substrate (Si) and catalyst (Ni). Titanium with thickness of 10-50 nm was deposited on the substrate prior to nickel deposition. The following describes detail experimental processes used to synthesize CNTs in a thermal CVD system.

Substrate Pre-treatment Annealing. Sample annealing at temperature range from 350° C. to 450° C. is used prior to CNTs growth. Sample is introduced inside the furnace and flushed with Ar gas (100-300 seem) for 10 minutes. The exhaust of the reactor is attached to a vacuum source which creates 10 to 1 Torr pressure inside the reactor. Ar flow is cut-off once vacuum is achieved inside the reactor. The furnace is turned on and temperature is set for 350° C. to 450° C. It takes approximately 5 to 7 minutes for the furnace to reach the set temperature. Heating under vacuum is carried out for 12 to 18 hours. At the end of the annealing time the furnace power is turned off and allowed to cool down until it reaches room temperature. The vacuum source is then cut-off and the system is purged with Ar. The system is opened and pre-treated substrate is ready for CNTs growth process.

CNTs growth processes by gas phase CVD. Annealed substrate is introduced inside the thermal CVD reactor. The CVD reactor is sealed and flushed with Ar gas (100 to 300 Sccm) for 10 minutes. After sufficient purging, the furnace power is turned on and the system is heated under Ar atmosphere until the set temperature (650° C. to 750° C.). Once the growth temperature is reached, Ar gas flow rate is changed to the desired value which can range from 5 to 400 sccm depending on the substrate combination used and quality of CNTs desired. Etching gas Hydrogen/Ammonia is introduced in the system at a flow rate ranging from 10 to 250 sccm. The etching process is carried out for 2 to 10 minutes to form nanometer size catalytic particles. After the etching step, Acetylene as the carbon source is introduced into the chamber to grow CNTs. The growth time ranges from 5 to 60 minutes. After the growth time, Acetylene is turned off while Ar and Hydrogen/Ammonia are kept at constant flow ratio for 1 minute. Then the Hydrogen/Ammonia and furnace are turned off and the sample is allowed to cool to room temperature in Ar (100-300 sccm) atmosphere. After cool down, the system is opened and sample is taken for further examination.

Growth of Aligned Carbon Nanotubes by Solid Precursor Assisted Chemical Vapor Deposition These examples pertains to a chemical vapor deposition process for growing aligned multiwalled carbon nanotube film on a variety of substrates. The chemical vapor deposition recipes adapted for the growth of aligned carbon nanotubes are very specific as they allow for the use of these films as electrodes for sensing applications.

The process of chemical vapor deposition (CVD) involves the transformation of gaseous molecules into solid material on the surface of the substrate. Metals, alloys, or polymeric films can be deposited by the chemical vapor deposition method and thus ideal for thermal growth of carbon nanotubes. A one step method is developed to prepare a large quantity of well aligned carbon nanotube film without any substrate pre-treatment or a preformed template, which utilizes an organo-metallic precursor as the source of carbon as well as the metal catalyst. This one-step production of bundles of aligned carbon nanotube array requires no prior preparation of the substrate or an external template to direct the alignment. This process allows growth of ACNTs on variety of conducting as well as insulating substrates like Silicon, Doped Silicon, Poly Silicon, Silicon Nitride, Silicon Oxide etc. Iron (II) Phthalocyanine (FePc) is used as the source which provides metal catalyst as well as carbon feed for preparing aligned carbon nanotubes. A mixture of Argon (Ar) and Hydrogen ($H_2$) is used as carrier gas during the growth process. The carbon nanotubes grown by this method are multiwalled carbon nanotubes, with length in the range of 1-50 μm and diameter in the range of 40-100 nm. The tubes grown are a mixture of hollow and bamboo structured tubes. The core size of these tubes range from 5-15 nm which is favorable for further doping processes. Trace amount of amorphous carbon have been detected on the side walls of the nanotube, but no apparent interference on the electrode properties has been observed.

ACNT growth procedure

1. The substrate (quartz slide/silicon chip) is cleaned with Isopropyl alcohol, dried in air and introduced into the flow reactor (quartz tube) (refer FIG. 14I).
2. Iron (II) phthalocyanine (0.1-0.7 g) is placed in a quartz/ceramic boat and placed inside the quartz tube.
3. The whole system is sealed and flushed with Argon (Ar) (300-500 Sccm) for 20-30 minutes. This step removes any oxygen present in the quartz tube and provides an inert reaction atmosphere.
4. The temperature of the furnace is set at desired growth temperature which may range from 800-960° C. depending on the size, density and quality of ACNTs.
5. As the temperature of the system reaches 800° C. the flow rate of Ar is reduced to desired flow rate (10-150 Sccm) and $H_2$ is introduced in the gas flow at a desired flow rate (10-150 Sccm). Allow 10 minutes for the gases to mix uniformly inside the reactor.
6. The gas flow is maintained steady through out the growth process.
7. Pyrolysis of the Precursor: Once the furnace attains constant set temperature, the precursor boat is transferred in the temperature range (450-750° C.) where the pyrolysis of the organo-metallic precursor is triggered. Iron and carbon source is released into the gas phase and gets carried into the flow stream by Ar and $H_2$. (30 sec-2 min)
8. The carrier gas transports the metal/carbon into the high temperature zone where the growth of carbon nanotubes on the substrate takes place. (2-10 min)
9. After the reaction time, the furnace is shut-off, the $H_2$ flow is turned off, and only Ar gas flow is maintained steady at a low flow rate (300-500 Sccm).
10. Once the furnace temperature reaches a safe value and all the $H_2$ is flushed out of the reactor system, the quartz tube is opened and exposed to air.

The substrate is taken out of the tube and further examination is carried out (SEM/TEM).

Encapsulation of Catalyst at the Base of the MWNTs

This example provides a fabrication process to insulate mainly the catalyst at the base of the carbon nanotubes, without insulating the tip or the wall (e.g., mid-section) of the tubes. Such insulation allows electrochemical response of carbon nanotubes with the sample solution while preventing undesirable electrochemical interaction of the catalyst with the solution. The insulation material also provides additional mechanical support for carbon nanotubes when the nanotubes are exposed to harsh environment such as high flow.

The MWNTs make an ideal electrode candidate for electrochemical detection. Nanotubes can be grown on catalyst such as nickel, iron, and lead. During electrochemical analysis, the catalyst can also be exposed to the solution thus exhibit electrochemical response. In order to prevent such undesirable electrochemical response, the catalyst can be insulated. This example provides a fabrication method of depositing silicon nitride as an insulating material for ion sensing application. This example also provides a fabrication method of depositing an insulating material covering nanotube structures where the insulating material is patterned by partial exposure of a positive photoresist. Also described is fabrication method for preventing nanotubes from forming honey-comb structure arising from stiction by supercritical point carbon dioxide drying method.

Figure 17A:
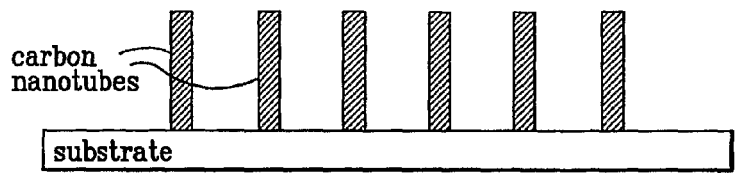
FIG. 17 shows a fabrication process of catalyst insulation and mechanical support.
Figure 17B:
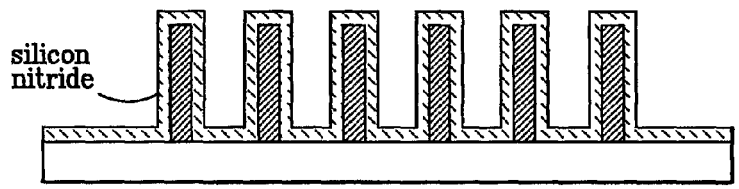
Figure 17C:
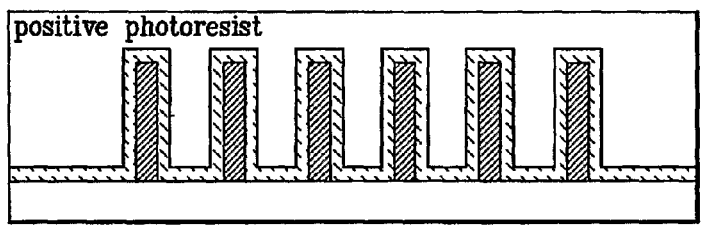
Figure 17D:
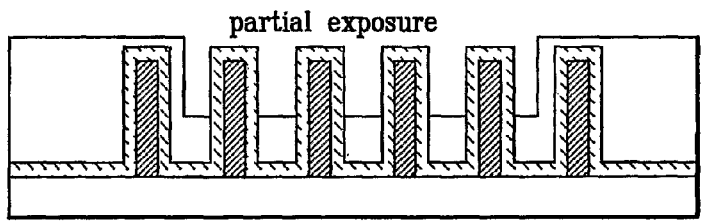
Figure 17E:
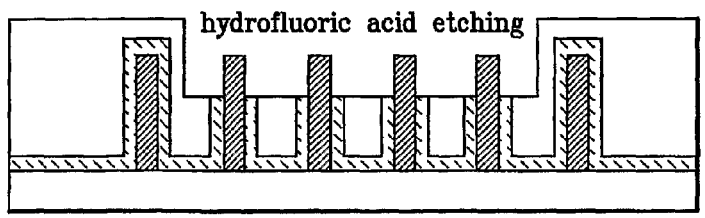
Figure 17F:
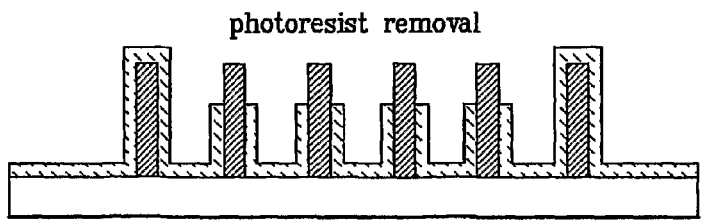

The processes in this example start with a 100 mm silicon wafer (FIG. 17A) with aligned carbon nanotube film. This process can also be applicable to other substrates such as glass wafers. Next, a 500A thick silicon nitride (FIG. 17B) is deposited by plasma-enhanced chemical vapor deposition at 380 C. acting as an insulating material. Other insulating material such as silicon oxide can also be used. Deposition method is not limited to evaporation, sputtering, thermal, hot wired deposition. In this application, silicon nitride is used because it effectively stops ionic molecules in contact with the nanotubes. After that, a positive photoresist (AZ9260) is spin-coated (2K rpm, 20 sec) and soft baked (115 C, 260 sec, hot plated) covering the entirety of the nanotubes (FIG. 17C). The photoresist undergoes partial ultra-violet exposure (300 mW/cm2, 4 sec) (FIG. 17D), such that some photoresist is left after development (AZ400:DI H20:1:3, 2.5 min) covering the lower portion of the nanotubes, while the upper portion of the silicon-nitride covered nanotubes are exposed. After development of photoresist, the sample might be undergoing supercritical point carbon dioxide drying to prevent nanotubes from sticking to each other forming honey-comb structures due to capillary-induced stiction. Subsequently, the sample (FIG. 17E) is exposed to wet etching such as buffered hydrofluoric acid (2 min)to etch away exposed silicon nitride residing on the sheath of the tubes. Finally phororsist (FIG. 17F) is removed by soaking in acetone or other solvents for a short time. The sample might again undergo supercritical point carbon dioxide drying to prevent nanotubes from sticking to each other forming honey-corn structures due to capillary-induced stiction.

Doping of MWNTs by Supercritical Treatment

In these examples, the gas like behavior of supercritical $CO_2$ is used to spread out along a surface more easily than a true liquid, while maintaining the dissolving property of a liquid. The supercritical $CO_2$ transports and encapsulates the molecules/compounds of interest into nanoscopic cavities like that of a hollow nanotube. Successful encapsulation of interesting molecules/compounds into nanotube cavities would give rise to 'peapod' like structures. The discussion that follows provides details of experiments carried out in supercritical medium with ACNTs, SWNTs and a target molecule of interest, which has a specific electrochemical signal. The characterization shows that we were able to dope the carbon nanotubes with the target molecule, both inside the hollow core and on the outer walls, while maintaining the electro activity of the molecule.

A critical point dryer is an instrument for drying materials/samples using a supercritical carbon dioxide ($CO_2$) medium. Carbon dioxide is known to form a very clean and inert supercritical fluid, which achieves super criticality at 31° C. and a pressure about 1070 psi.

Procedure—Condition 1: Substrate/Sample: ACNT film (Solid Precursor CVD), SWNT (commercial sample).

Target molecule: {6}-1-(3-(2-thienylethoxycarbonyl)-propyl)-{5}-1-phenyl-[5,6]-C61. (64BFA)

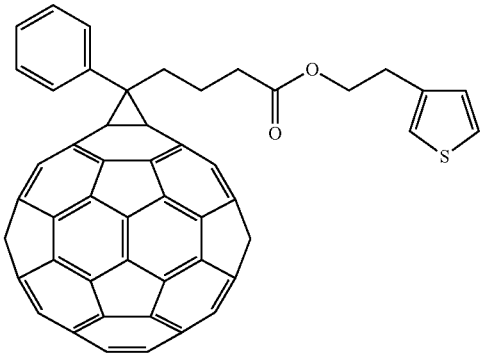 [SMILES: O=C(CCCC1(c2ccccc2)C2c3cc4c5c6c(cc7ccc8cc9c%10c%11c(cc(c%12c3c5c(c%12%11)c3c6c7c8c%103)C21)C9)C4)OCCc1ccsc1]

Figure 18A:
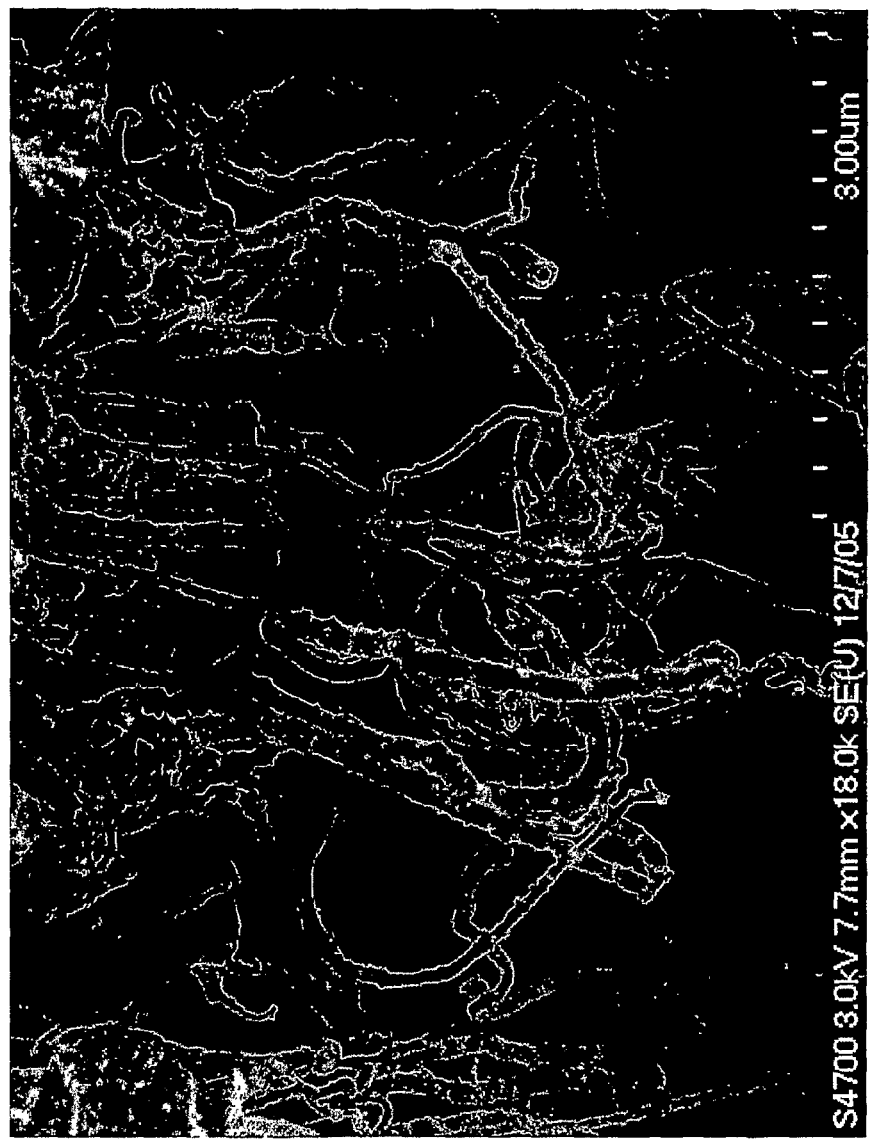
FIGS. 18A and 18B: (a) SEM of ACNT film before supercritical treatment; (b) TEM of ACNT before supercritical treatment.
Figure 18B:
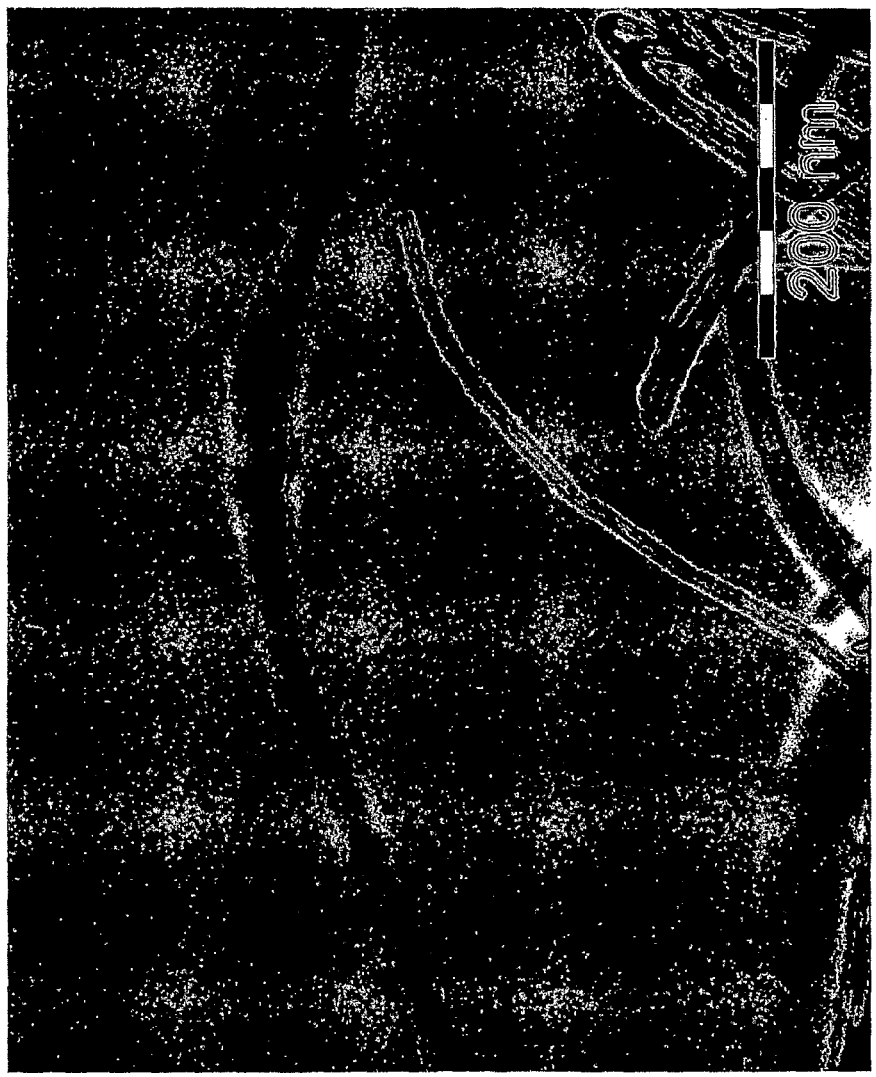
Figure 18C:
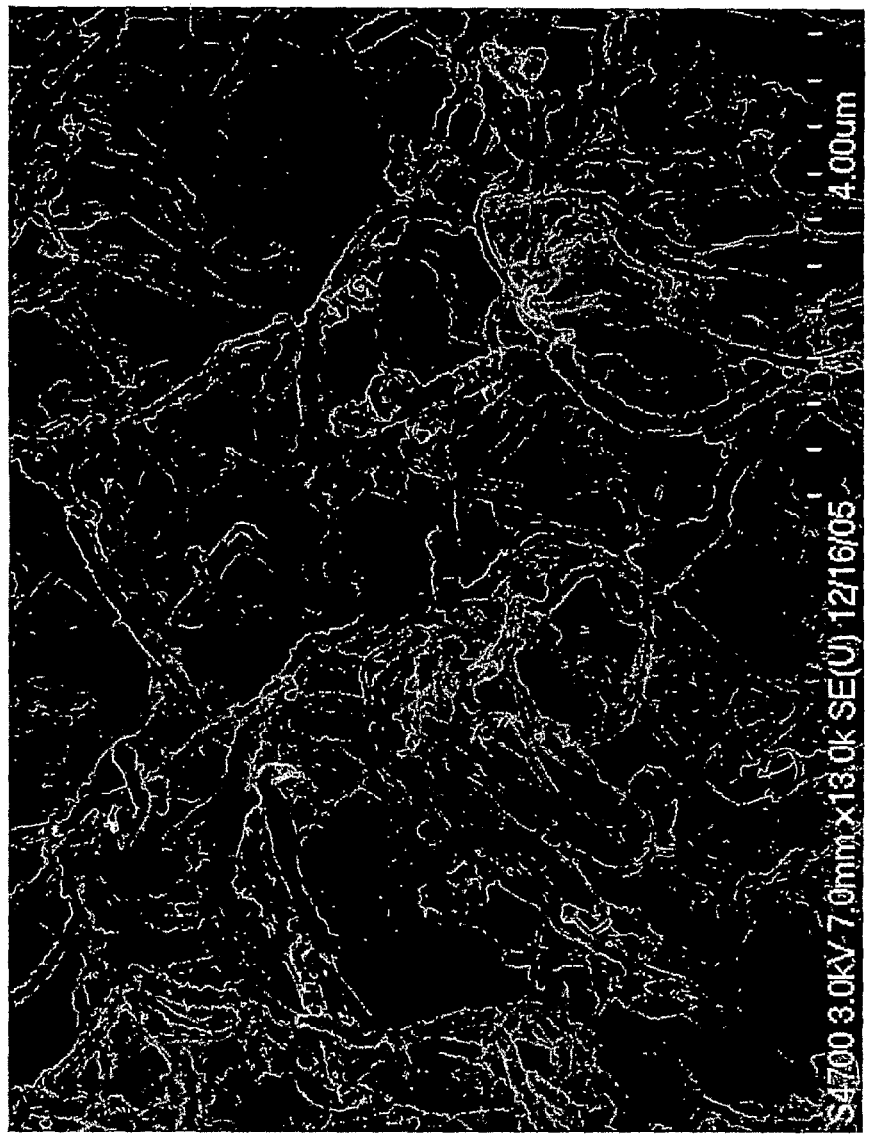
FIG. 18C and FIG. 18D: (a) SEM of ACNT film after supercritical treatment; (b) TEM of ACNTs after supercritical treatment.
Figure 18D:
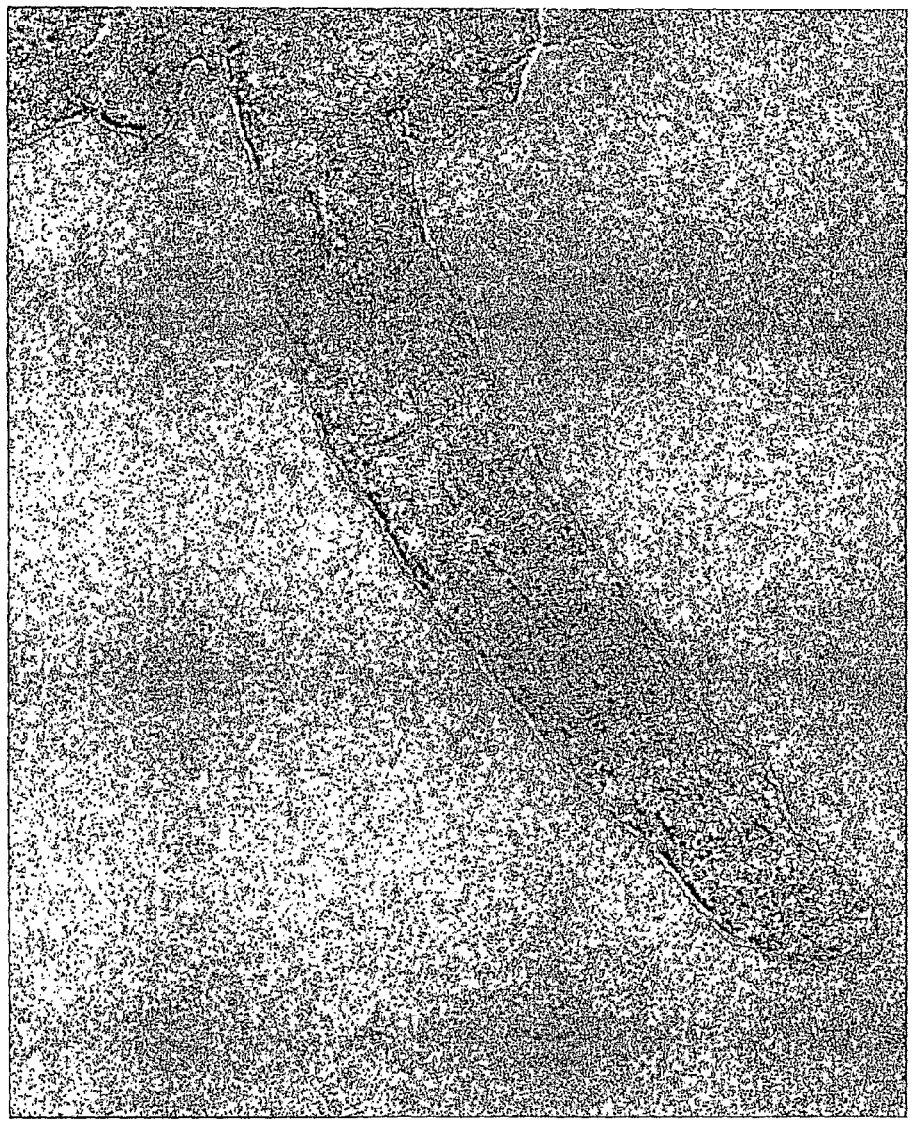

Solvent: Carbon Disulfide ($CS_2$)
Temperature: 80° C.
Pressure: 2000 psi
Time: 2 days Characterization: The ACNT film and SWNT powder were air oxidized (conditions in lab book) prior to any treatment, in order to create defects (holes) on the walls of the CNTs. They were characterized with SEM and TEM (FIG. 18A) before the supercritical treatment with Condition 1. The electrochemical behavior of the ACNT film was also recorder prior to the treatment.

Figure 18E:
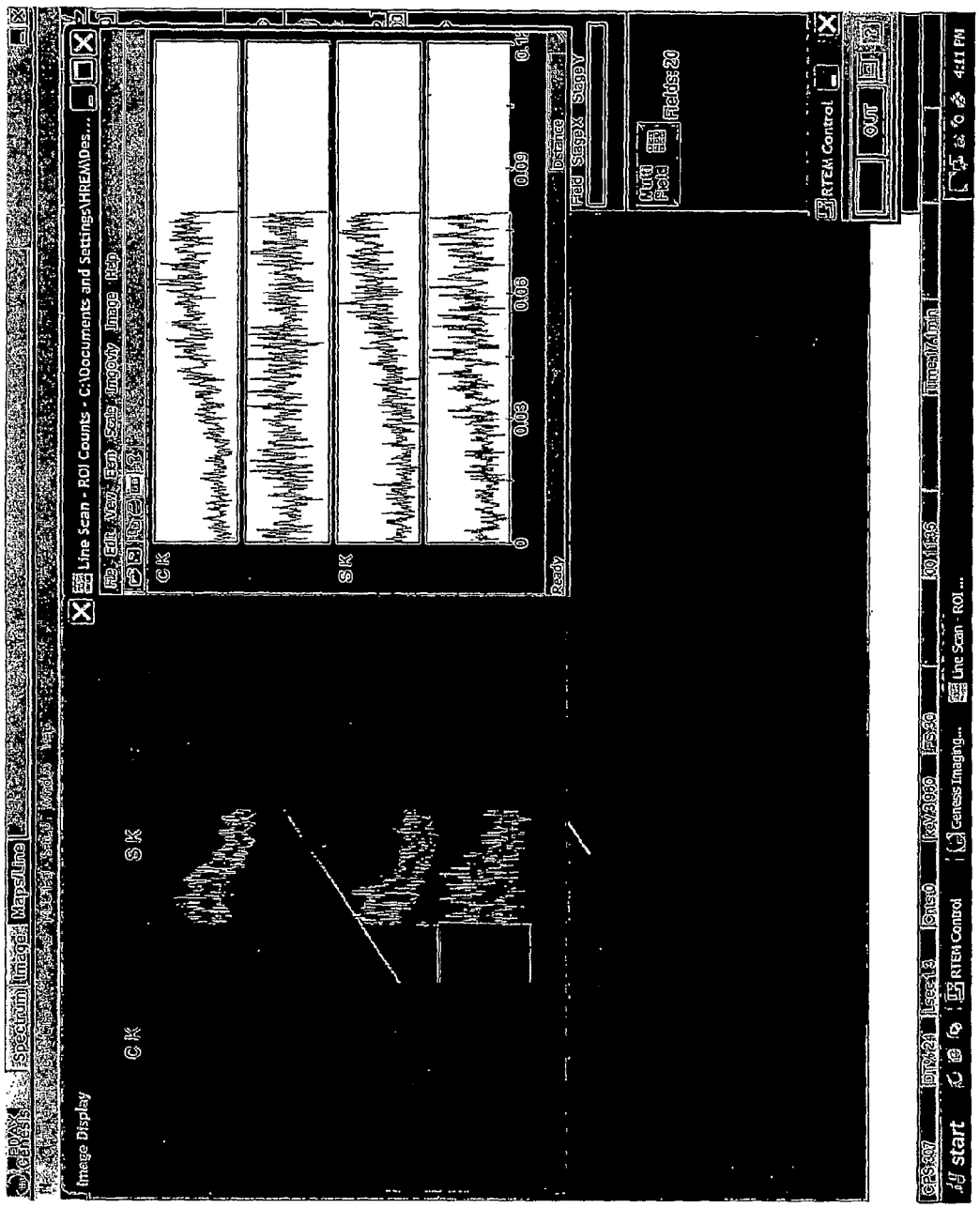
FIG. 18E Line scans EDX of ACNT after supercritical treatment.

After the supercritical treatment, the samples were thoroughly washed with $CS_2$ and MeOH and prepared for further characterization. The treated ACNT film was examined in the SEM and it was evident that there is a coating on the nanotube surface. The TEM evaluation shows that there is a definite coat in/around the carbon nanotubes. To confirm that the target molecule is not only present on the surface of the nanotubes, but also inside the hollow core of the tubes, (energy dispersive X-ray) EDX was performed. From FIG. 18E, it is evident that there is an increase in the levels of carbon and sulfur (indicative of the target molecule) in the centre of the tube.

Figure 18F:
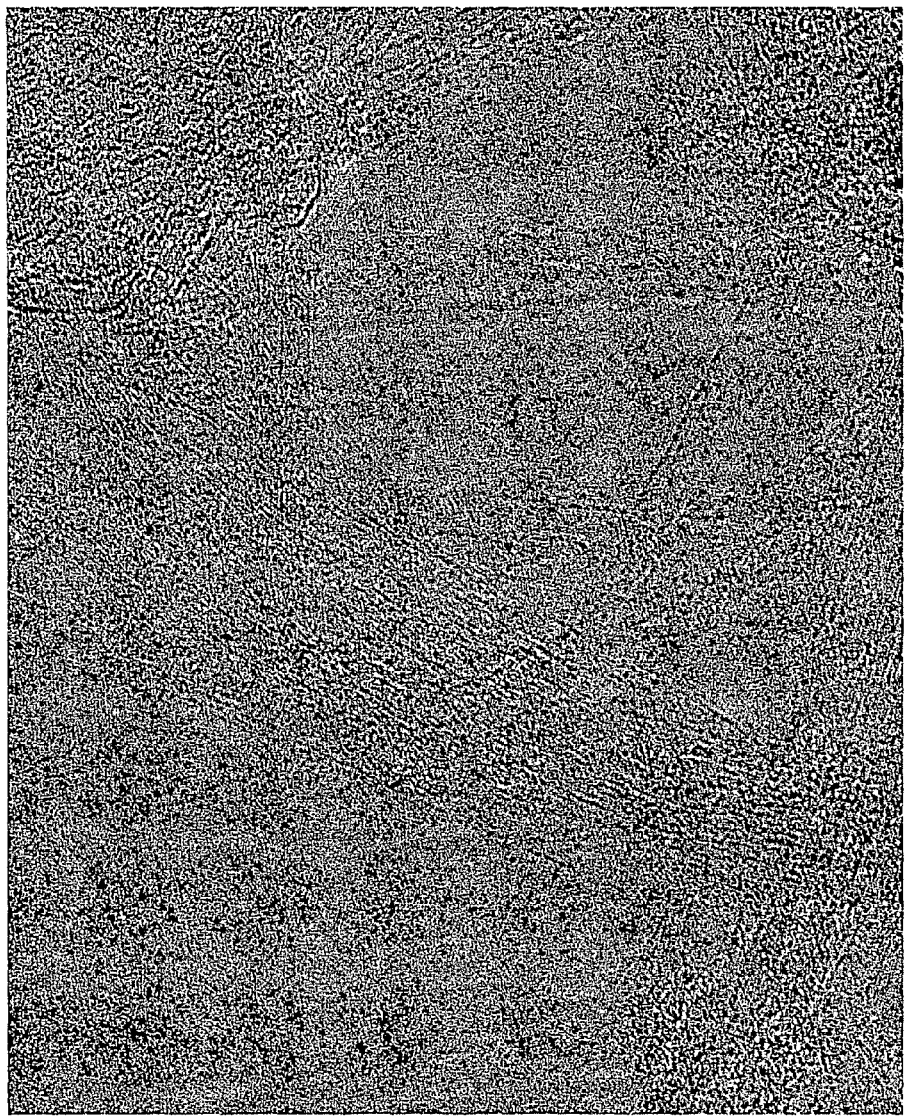
FIG. 18F High resolution TEM of SWNT sample after supercritical treatment.

The SWNT powder sample was characterized with high resolution TEM, where in the presence of fullerene like molecule structure are visible (FIG. 18F).

Figure 18G:
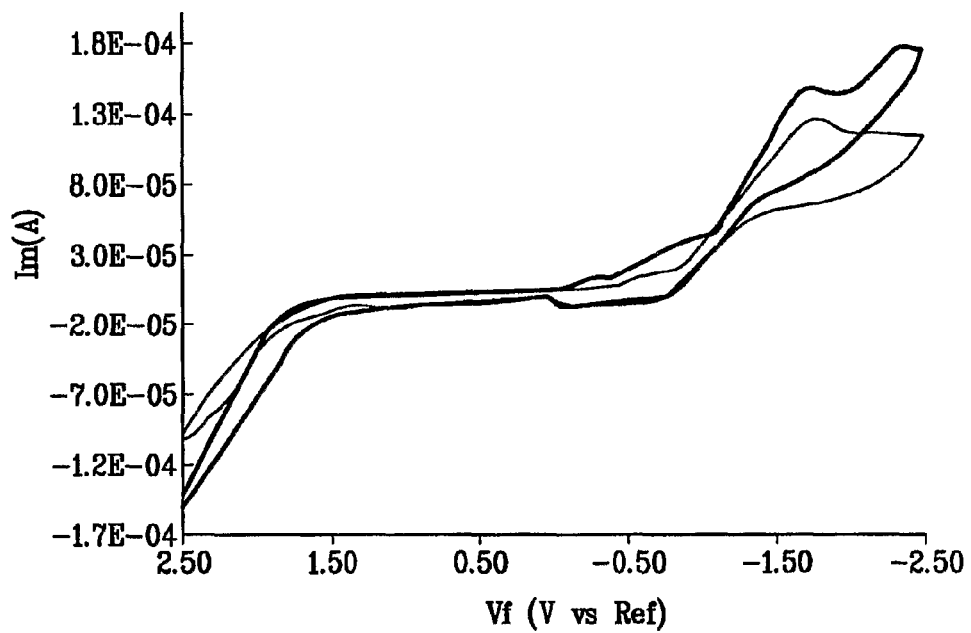
FIG. 18G Signature CV of 100 ppm 64BFA dissolved in methylene chloride solution in presence of 0.05 M tetra butyl ammonium hexafluoro phosphate supporting electrolyte.
Figure 18H:
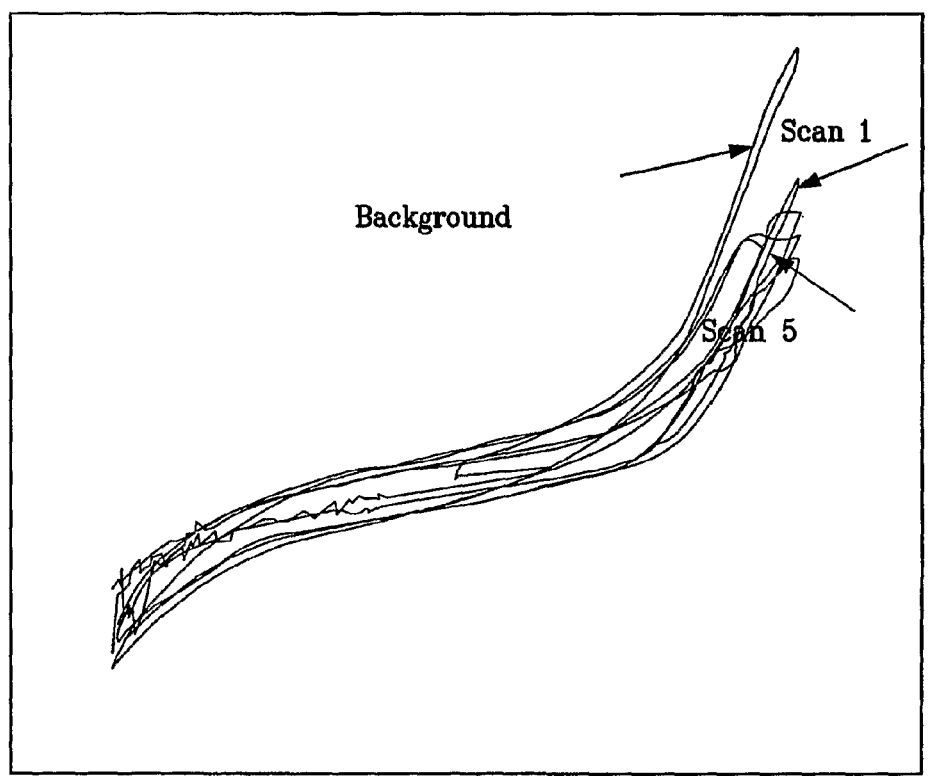
Figure 18I:
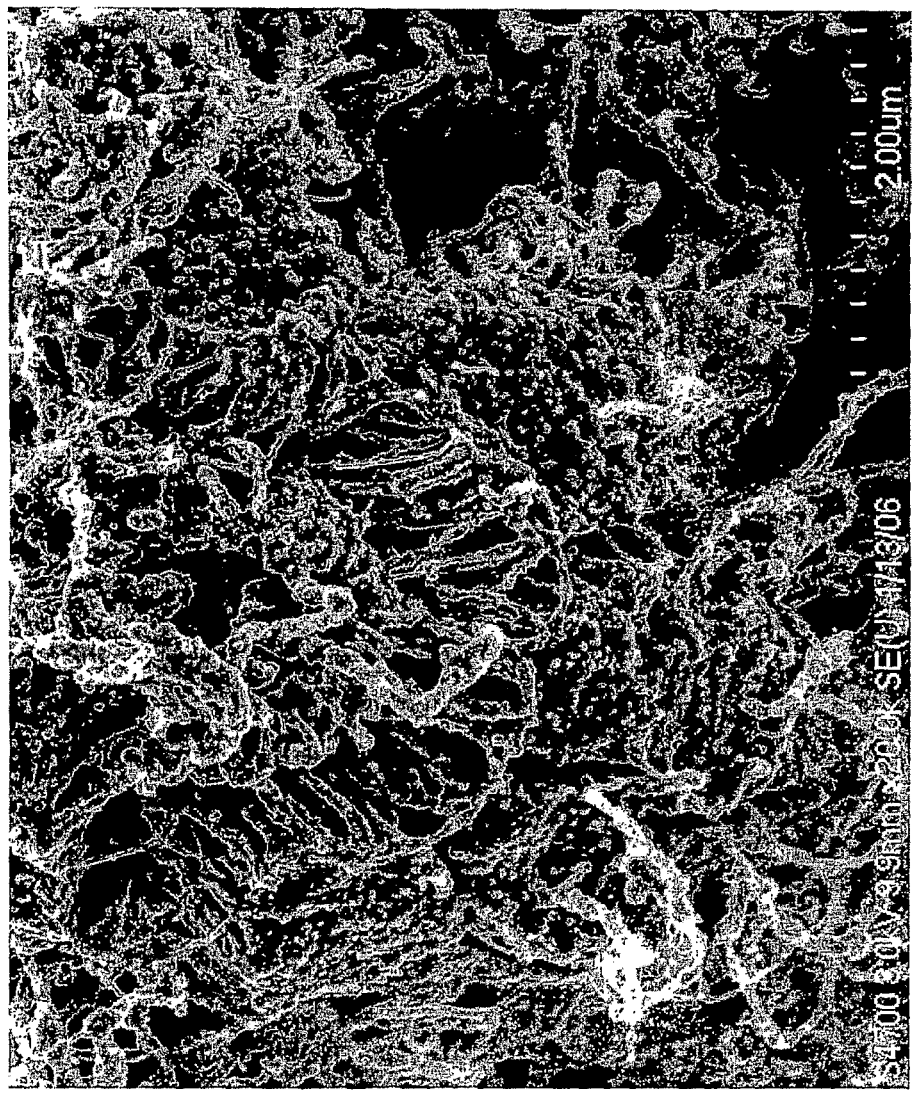
FIG. 18I SEM characterization of ACNT sample after supercritical treatment with conditions 2.
Figure 18J:
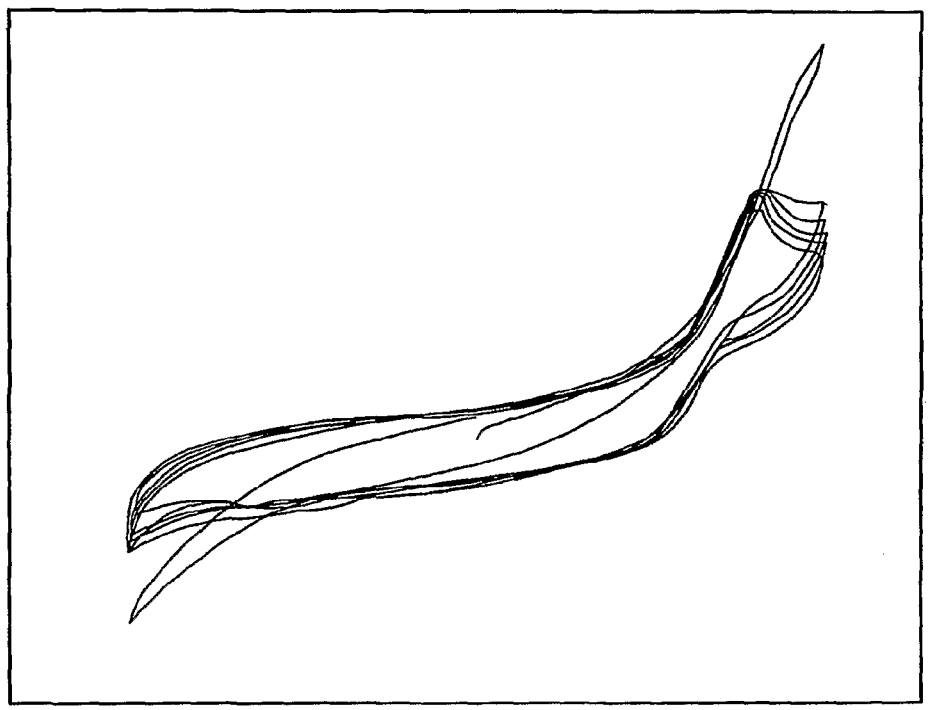

After the verification that target molecule moieties are present in the core of the nanotubes, the ACNT sample film was characterized electrochemically to check for the specific target molecules. The CVs exhibit specific target molecule signal (FIG. 18G, 18H) providing proof that the molecule is electrochemically active even after the treatment.

As shown in FIG. 18 (G, H) it is evident from the signature peak observed at ~−1.5V that the target molecule 64BFA is present and electrochemically active on the ACNT film after the supercritical treatment.

Condition 2: Substrate/Sample: ACNT film (Solid Precursor CVD)
Target molecule: {6}-1-(3-(2-thienylethoxycarbonyl)-propyl)-{5}-1 phenyl-[5,6]-C61. (64BFA)
Solvent: Carbon Disulfide ($CS_2$)
Temperature: 40° C.
Pressure: 1200 psi
Time: 5 hrs ACNT film was treated with Condition 2, in different Critical Point Dryer instrument, which had limited temp and press range. The treatment was carried out with the same target molecule as in Condition 1. The film was air oxidized (550° C. for 30 sec) prior to any treatment. Supercritical treatment (Condition 2) was carried out in the Bio imaging Lab facilities (DBI). The ACNT sample after treatment was thoroughly rinsed with $CS_2$ and MeOH solvents, to remove any loosely attached compounds. The SEM characterization (FIG. 18I) showed coating on the surface of the nanotubes (Similar to that observed with Condition 1 samples).

The electrochemical response of the film after the treatment was also recorded. It was observed that the target molecule specific signals are present and that the compound is electro-active. (Ref FIG. 18(G) for signature electrochemical signal for the target molecule in solution)

Amperometric Reduction of Free Chlorine at Carbon Nanotube Films

When either chlorine gas ($Cl_2$), hypochlorite solution (NaOCl), or solid $Ca(OCl)_2$ are added to water (for water disinfection), the following reactions take place

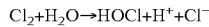
$Cl_2 + H_2O \rightarrow HOCl + H^+ + Cl^-$

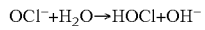
$OCl^- + H_2O \rightarrow HOCl + OH^-$

The reduction reaction of the hypochlorite ion at the electrode in aqueous solutions can be described as:

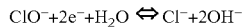
$ClO^- + 2e^- + H_2O \leftrightarrow Cl^- + 2OH^-$

Carbon nanotube electrodes (CNTs) are designed to be electrochemically robust to strong oxidizing agents such as the oxoacids of chlorine. In these examples, CNTs were used as working electrodes for the analysis of free chlorine in aqueous solutions using the reduction reaction of free chlorine described above.

The amperometric reduction of ClO— was conducted at 0 V for 5 s. The resulting charge under the i-t curve was used for quantitation.

A single compartment three electrode glass cell was used. The planar CNT working electrode was pressed against a viton o-ring and clamped to the bottom of the cell. A graphite rod was used as the counter electrode and a commercial Ag/AgCl (BAS systems) served as a reference electrode (E° Ag/AgCl=0.034 V Vs calomel). The geometric area of the working electrode was ca. 0.2 cm². All measurements were performed at room temperature ~25° C.

Chemicals. Phosphate buffer was prepared by mixing appropriate volumes of solutions of 0.05 M sodium phosphate dibasic and 0.05 M sodium phosphate monobasic (Sigma-Aldrich) to yield the desired pH (usually pH 7). Chlorine solutions were initially prepared from a stock of 5% w/w hypochlorous acid (EMD chemicals Inc.). This "bleach" solution was found to be unstable in spite of being stored at 4° C. and there was ambiguity as to its exact concentration. Henceforth, Free Chlorine Standard (Hach Voluette, catalog no. 14268) was used as the stock solution of the hypochlorous acid (initial concentration of HOCl=79.3 ppm or 61.9 ppm). These stock solutions had been commercially prepared by generating and dissolving chlorine gas in slightly alkaline, high purity water of zero chlorine demand. All solutions were prepared in glassware treated to make them chlorine demand free.

Figure 19A:
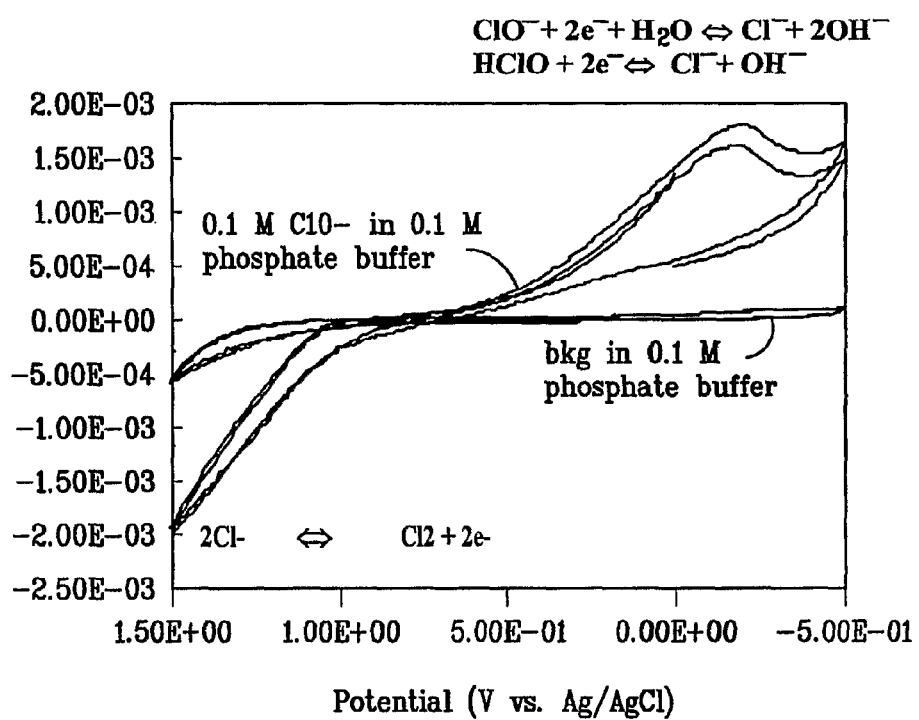
FIG. 19A i-E curve for the electrolysis of 0.1 M ClO— in 0.1 M phosphate buffer.

FIG. 19A shows the i-E curves for the electrolysis of 0.1 M $ClO^-$ in 0.1 M phosphate buffer (pH 6.8) and for the phosphate buffer by itself. The oxidation peak observed is for the chlorine evolution reaction which shows an onset potential of about 900 mV at the CNT electrodes.

The cathodic charge observed in the potential range from 0 mV to −500 mV is due to the reduction of the hypochlorite ion/hypochlorous acid species according to the listed equations.

Figure 19B:
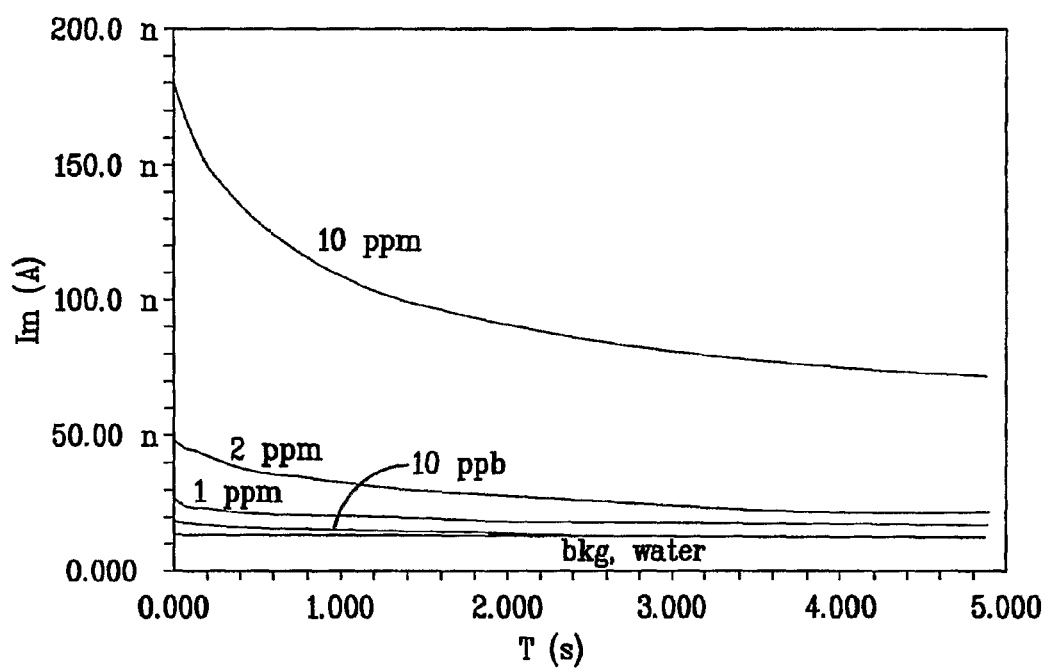
FIG. 19B Typical amperometric reduction curves obtained for the reduction of hypochlorous acid in 18.2 Me-cm water. $R^2=0.9888$ in this case.

FIG. 19B shows typical amperometric reduction curves obtained for the reduction of the free chlorine species in water (solid-phase grown CNT, 0.11 cm² inner area of o-ring). These curves are for solution concentrations of chlorine ranging from 10 ppb to 10 ppm. Plots of the resulting charge under the curves versus the solution concentration of chlorine are linear ($R^2$=0.9888 in this case).

The current vs. $t^{-1/2}$ plots also showed a linear relationship, indicating a semi-infinite linear diffusion of the chlorine species to CNT electrodes.

The pH of the solution determines the relative proportions of hypochlorous acid (HOCl) and hypochlorite ion ($OCl^-$). At 0° C. and pH 7.9, chlorine is present as half active HOCl and half inactive $OCl^-$. The dissociation reactions of chlorine dissolved in water can be written as follows:

$Cl_2 + H_2O \rightarrow H^+ + Cl^- + HOCl$  $pK_1$=4.6 at 25° C.

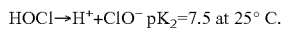
$HOCl \rightarrow H^+ + ClO^-$  $pK_2$=7.5 at 25° C.

Figure 19C:
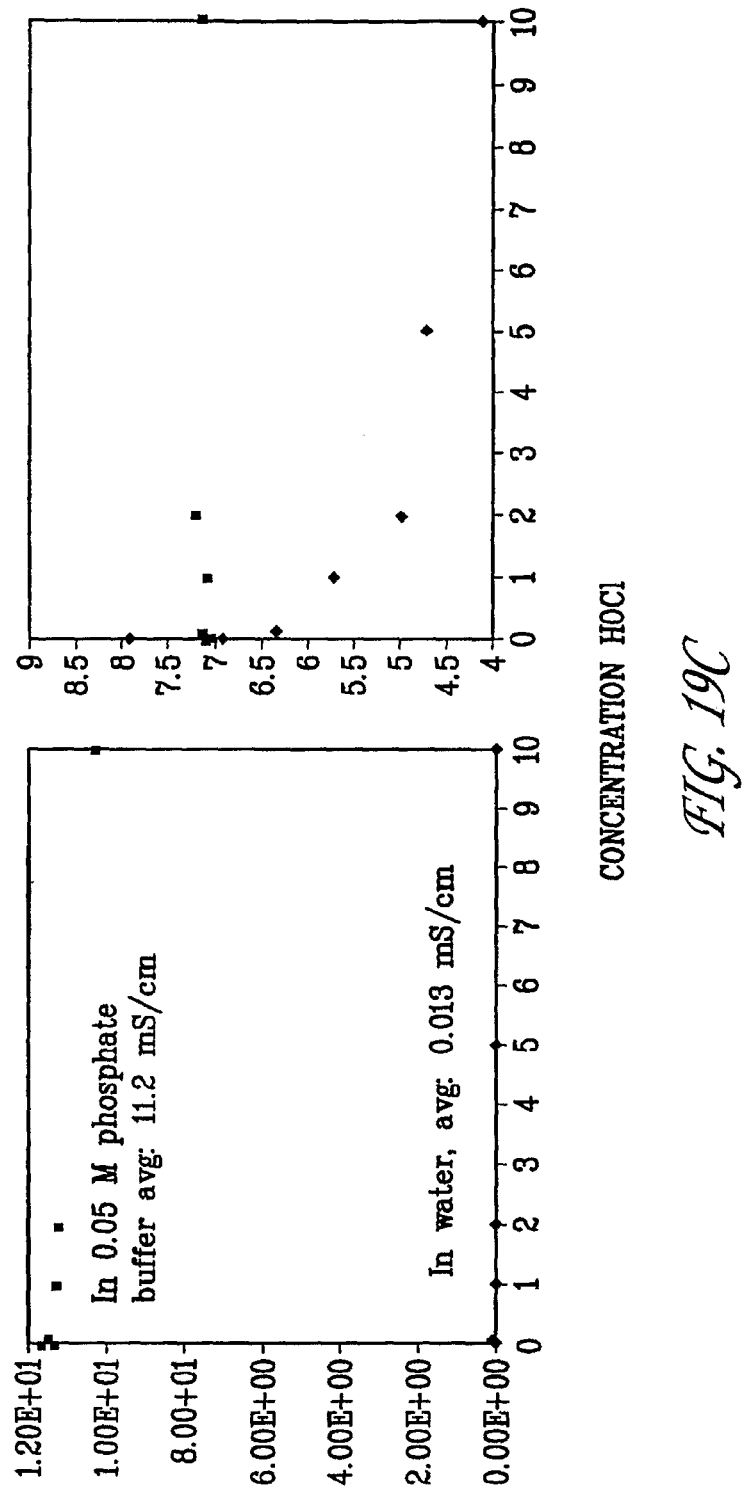
FIG. 19C Effect of conductivity (mS/cm, plot on the left) and pH vs. the concentration of chlorine in its solutions.

FIG. 19C demonstrates the conductivity and pH trends for solutions of dissolved chlorine.

Figure 19D:
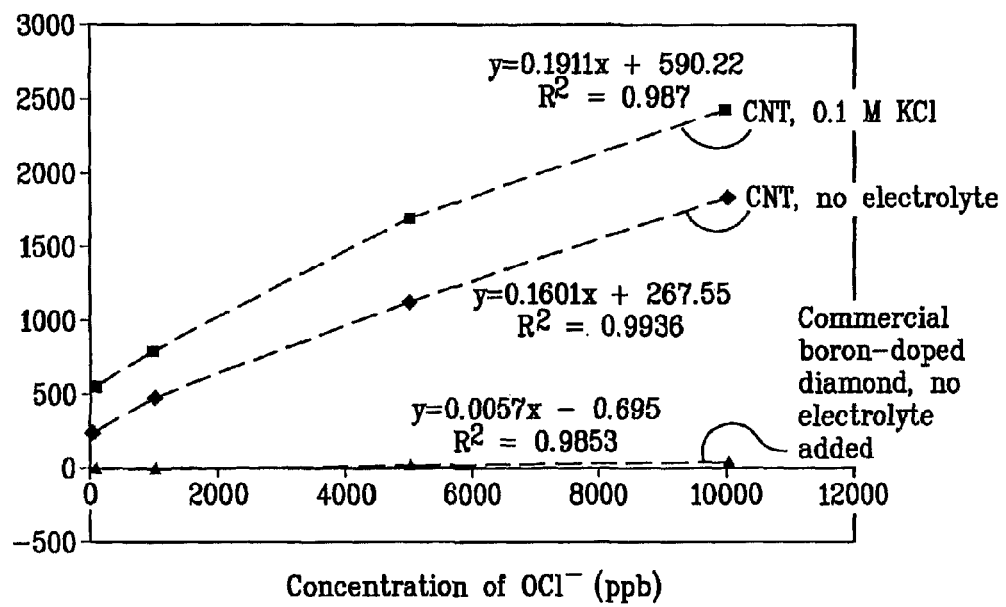
FIG. 19D Plots of resulting reduction charge Vs. free chlorine concentration using CNT electrodes (with and without the addition of electrolyte). For comparison, a similar plot using a commercial doped diamond electrode is also presented.

FIG. 19D demonstrates the effect of electrolyte on the response for the reduction of the hypochlorite ion on CNTs in comparison with a commercial sample of conducting diamond (a model planar electrode). Plots of resultant hypochlorite reduction charge Vs. its solution concentration are presented. CNTs are expected to have a minimum internal iR drop due to their small sizes and good electrical conductivity. Indeed, the ratio of the sensitivities of response with no added electrolyte was CNT:Diamond 28.5.

Based on these experiments, one can carry out the free chlorine reduction assay on CNT electrodes without addition of electrolyte.

Figure 19E:
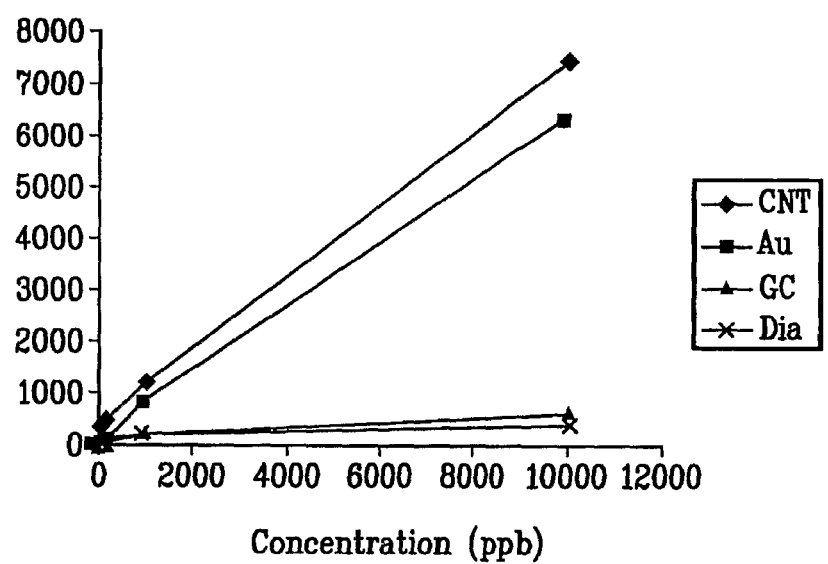
FIG. 19E Free chlorine Reduction Reaction: Comparison of the response of CNTs, Diamond, Glassy Carbon and Gold. Reduction performed at constant potential of 0 V, applied for 5 s in 0.05 M phosphate buffer.

FIG. 19E shows the CNT comparison plot of resultant hypochlorite reduction charge Vs. its solution concentration using different electrode surfaces such as diamond, glassy carbon (GC) and gold. The $R^2$ values were found to be CNT: 0.9997, Au: 0.9996, GC: 0.9853 and conducting diamond: 0.9263. It was found that the sensitivities were highest for CNTs followed by Au, GC and diamond in that order.

Figure 19F:
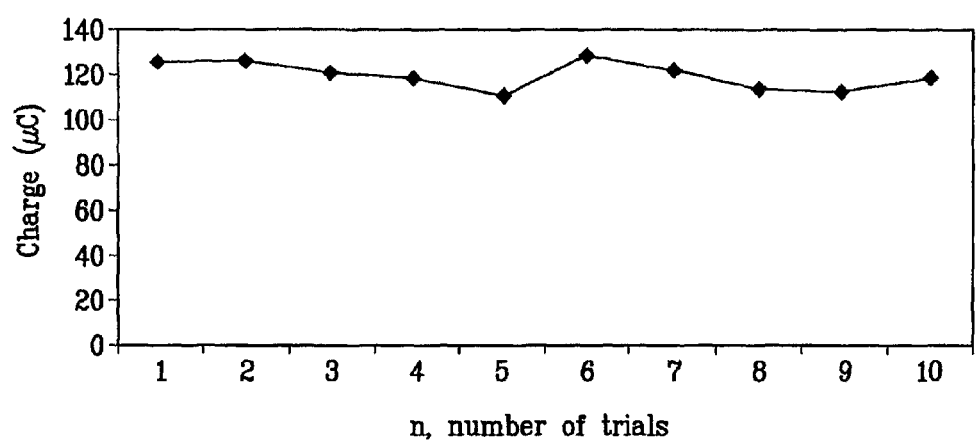
FIG. 19F Response Precision of Free Chlorine Reduction Reaction, n=10.

FIG. 19F gives an example of the repeatability of the response of the free chlorine reduction reaction on CNTs. Here, the plot of trial number (n) versus the resultant charge for the same concentration of hypochlorite (100 ppb $ClO^-$ in 0.05 M phosphate buffer) is shown.

The Coefficient of Variation (%) of a set of values is calculated as: 100*(Standard Deviation)/(mean value of set). In this case the coefficient of variation was found to be 5.25% which is in an acceptable range.

CNT based sensors for free chlorine have been demonstrated in these examples to provide superior sensitivity as compared to conventionally used electrode materials such as diamond, gold and glassy carbon. The response is precise and the linear dynamic range spans 4-5 orders of magnitude. Assays without the addition of supporting electrolyte are also analytically useful.

Potentiometric Measurement of Calcium Based on a Conducting Polymer Cladded MWNT Structure Ion-selective electrodes are electrochemical sensors that measure a wide range of analytes in aqueous solutions. A solid-contact calcium selective electrode is described that is based on a calcium ionophore doped conducting polymer CNT cladding. The analytical performance of this sensor (potentiometric) was evaluated. When the ionophore doped CNT electrode was in contact with an aqueous solution containing calcium, an electrode potential develops across the surface which is dependent on the level of free calcium ion.

The electrochemical cell consisted of ion selective and reference electrodes. The potential difference between the cladded CNT (ion selective) and reference electrode (Silver/Silver chloride) was measured with a commercial pH/mV meter. All the measurements were carried out in Tris buffer (pH 7.2), and at room temperature (~25 C). The potential readings were taken after stabilization for 1 minute.

Chemicals: 0.05 M Tris Hydroxy methyl amino methane (Fisher, N.J.) buffer (pH 7.2) was used for all the potentiometric measurements. $10^{-1}$-$10^{-5}$M Calcium chloride (Sigma, Mo.) solutions were prepared from 0.1 M $CaCl_2$ stock solution in Tris buffer. Polyaniline (PANI) emeraldine base powder, Di(2-ethylhexyl)phosphate ($H^+DEHP^-$) and Potassium tetrakis(4-chlorophenyl)borate $KB(ClPh)_4$ were purchased from Sigma. Calcium ionophore (ETH 1001) was obtained from EMD Biosciences. All the aqueous solutions were prepared using deionized water.

Figure 20A:
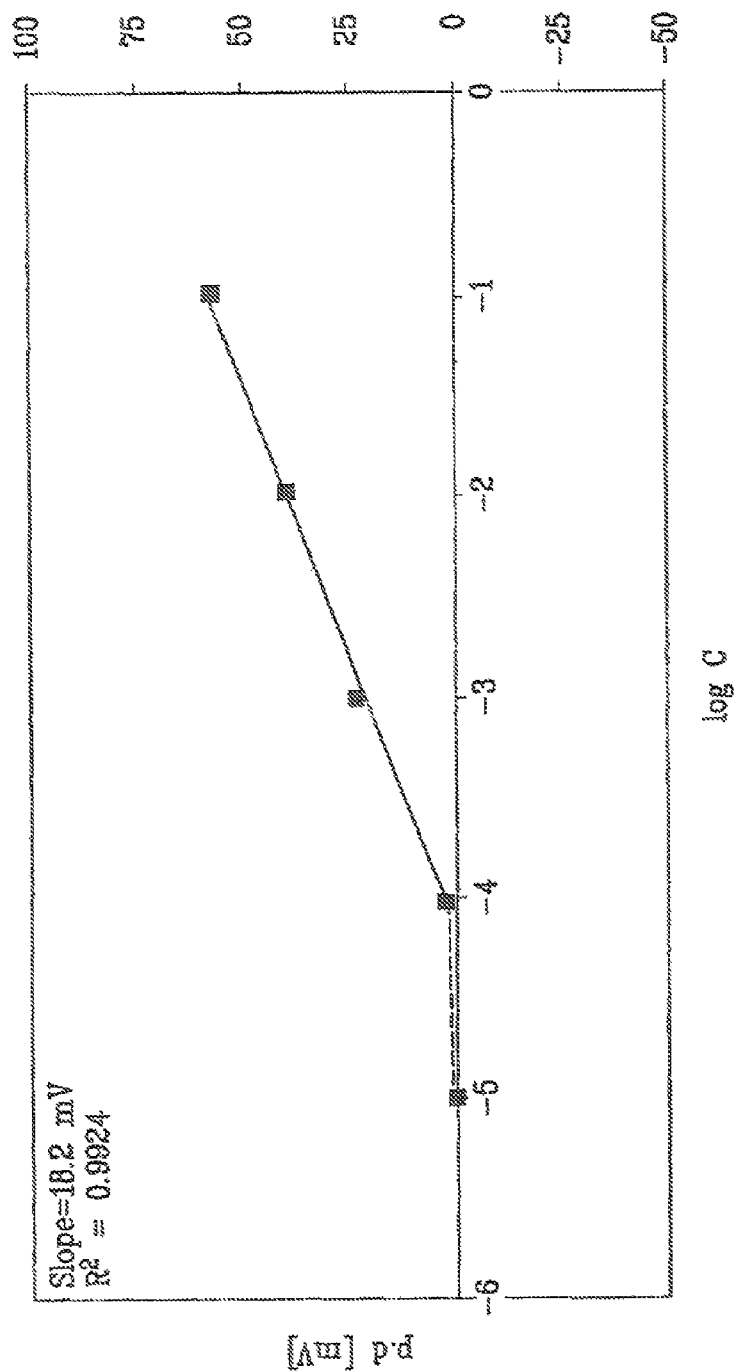
FIG. 20A Typical calibration curve for the solid contact Ca-ISE (Chip# SP-97). $10^{-1}$-$10^{-5}$ M CaCl$_2$ solutions were prepared in Tris Buffer (pH 7.4) and the EMF was measured against Ag/AgCl reference electrode.
Figure 20B:
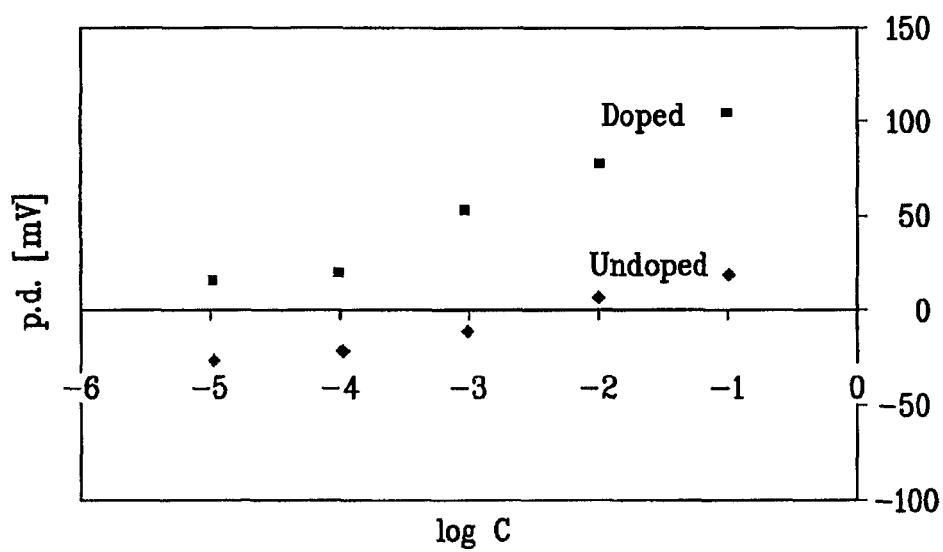
FIG. 20B Doped and Undoped PANT response to Calcium. $10^{-1}$-$10^{-5}$ M CaCl$_2$ solutions were prepared in Tris Buffer (pH 7.4) and the EMF was measured against Ag/AgCl reference electrode.

Referring to FIGS. 20A and 20B, the electrode showed Nernstian response toward calcium with a slope of 18.2 mV (ideal theoretical Nernstian slope is 29.5 mV). The undoped PANT film showed a concentration dependent ionic response. To account for this, the potential difference values at each concentration were corrected for the calcium response of the doped PANT electrode. Linear response ranges from $10^{-4}$ to 0.1 M $Ca^{2+}$. The response is similar to a conventional PVC membrane matrix cast on a conducting polymer cladded CNT electrode. Thus, the conducting polymer by itself can act as a matrix and demonstrate a stable response. Measuring the PANT film with the calcium ionophore, gave rise to the slope of the graph being drastically improved. An overlay of the response curve for the doped and undoped PANT electrode is shown in FIG. 20B.

Figure 20C:
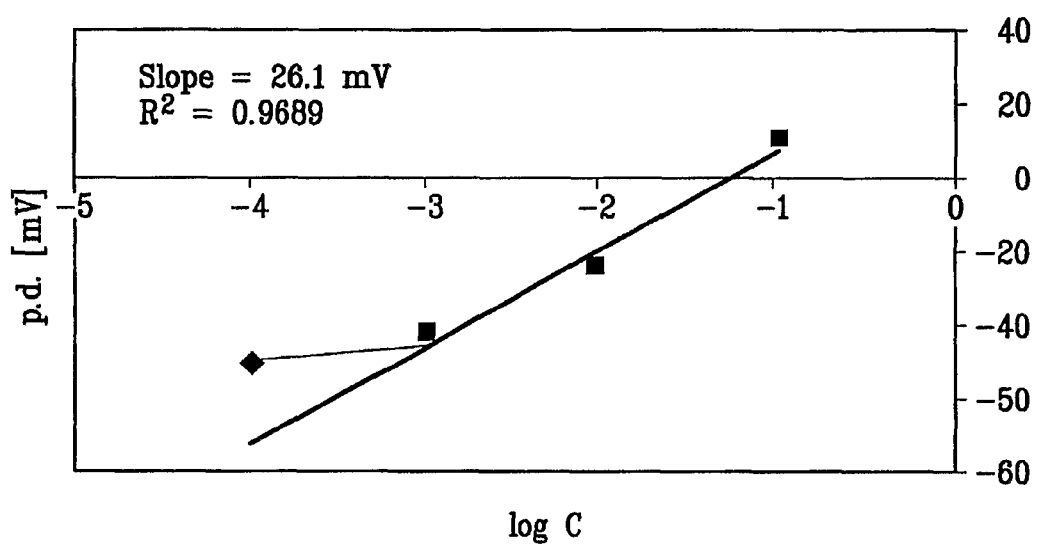
FIG. 20C Calibration curve for the solid contact Ca-ISE (Chip # SP-158). $10^{-1}$-$10^{-4}$ M CaCl$_2$ solutions were prepared in Tap H$_2$O and the EMF was measured against Ag/AgCl reference electrode.
Figure 20E:
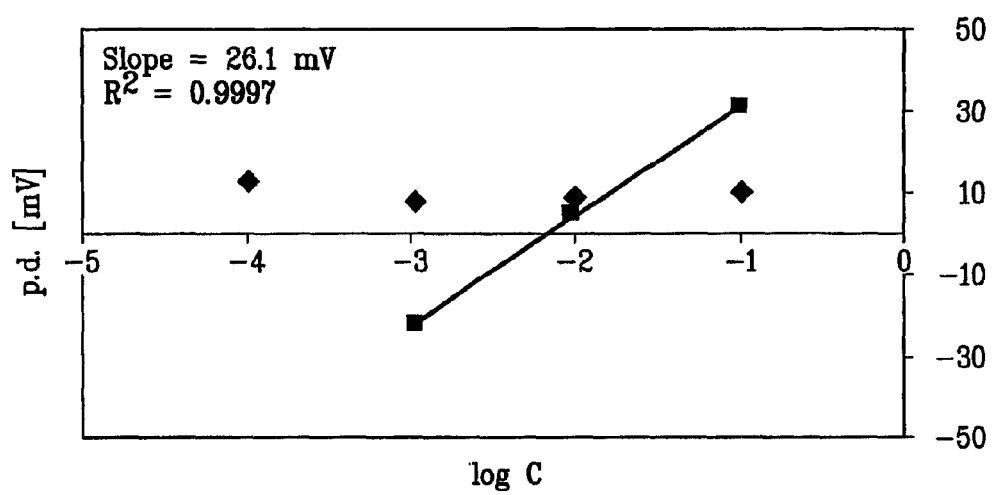
FIG. 20E Selectivity studies for $Ca^{2+}$ selective electrode (Chip if SP-97). (■) Response for $Ca^{2+}$ in DI $H_2O$ and (♦) Response for 0.01 M $CaCl_2$ in $10^{-1}$-$10^{-4}$ M KCl.
Figure 20F:
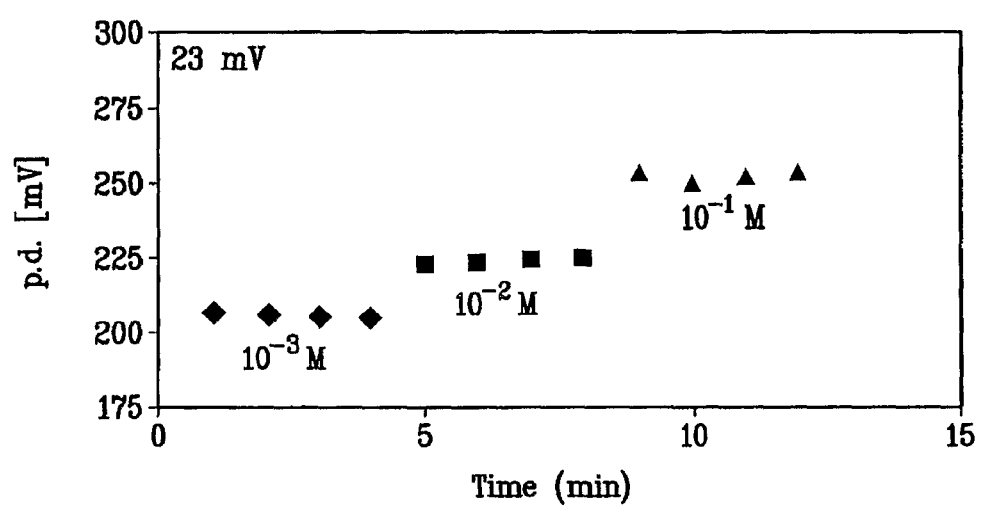
FIG. 20F Experimental time traces for the EMF measurements of the pre-polymerized PANi (Chip # SP-171).

Referring to FIG. 20C, the electrode showed Nernstian response toward calcium with a slope of 26.1 mV. Linear response ranges from $10^{-3}$ to 0.1 M $Ca^{2+}$. There is an order of magnitude difference in the detection limit with tap water ($10^{-3}$ M). The redox and pH sensitivity of the PANI limits the performance of the sensor. The conductivity of polyaniline is known to be strongly affected by the oxidation state as well as the degree of protonation.

Interference Studies. Selectivity studies of the Calcium selective electrode were carried out with respect to $K^+$, $Na^+$ and $Mg^{2+}$ respectively. $Mg^{2+}$ is the major cation that causes measurement errors in water sensing devices. Both $Ca^{2+}$ and $Mg^{2+}$ contribute to the total hardness of water. In regard to measuring water total hardness, interference from $Mg^{2+}$ apparently does not alter the sensor performance.

Results. CNT based sensors provide robust, portable, simple, and relatively inexpensive methods of analysis. Polymer cladded CNTs can provide miniaturized electrochemical sensors.

What is claimed:

1. An antennae assembly electrode, comprising:
   an electrically conductive layer at least partially surmounting a substrate;
   a planar protective layer, said protective layer having a plurality of contact holes; and
   an assembly of doped antennae vertically oriented with respect to the electrically conductive layer and electrically connected with the electrically conductive layer through the contact holes, wherein each of the doped antennae comprises a doped MWNT comprising:
   a base end attached to the electrically conductive layer,
   a mid-section comprising an outer surface surrounding a lumen, wherein a majority of the outer surface of the mid-section is in fluidic contact with an environment in contact with a top end of the antennae;
   the top end disposed opposite to the base end, wherein neither the mid-section nor the top end are connected to the electrically conductive layer; and
   a dopant attached to or contained within the lumen, a dopant attached to or contained within the outer surface, a dopant attached to or contained within the top end, or any combination thereof.

2. The antennae assembly electrode of claim 1, further comprising a catalyst at least partially surmounting the electrically conductive layer, wherein at least a portion of the doped MWNT are attached at their ends to the catalyst.

3. The antennae assembly electrode of claim 2, wherein the assembly of doped MWNT comprise a plurality of MWNT having one or more fill molecules.

4. The antennae assembly electrode of claim 3, wherein the fill molecules include molecules, molecular ions, atoms, atomic ions, or any combination thereof.

5. The antennae assembly electrode of claim 3, wherein the fill molecules comprise one or more fullerenes, doped fullerenes, ionophores, ion exchangers, redox molecules, conductive polymers, metals, or any combination thereof.

6. The antennae assembly electrode of claim 5, wherein the ionophores include cyclic polyethers, antibiotics, linear chain ligands or any combination thereof.

7. The antennae assembly electrode of claim 6, wherein the cyclic polyethers comprise 12-crown-4 to 24-crown-8 polyethers, or any combination thereof.

8. The antennae assembly electrode of claim 6, wherein the ionophores includes one or more cryptands, calixarenes, rotaxanes, or any combination thereof.

9. The antennae assembly electrode of claim 5, wherein the fullerenes include one or more of $C_{60}$, $C_{70}$, $C_{80}$, $C_{90}$, or any combination thereof.

10. The antennae assembly electrode of claim 5, wherein the fullerenes are doped fullerenes.

11. The antennae assembly electrode of claim 10, wherein the doped fullerenes are filled, coated, chemically functionalized, or any combination thereof.

12. The antennae assembly electrode of claim 5, wherein the ion exchangers include quaternized PVC, sulfonated PI'FE, or any combination thereof.

13. The antennae assembly electrode of claim 6, wherein the antibiotics include valinomycin, nonactin, monensin, iosin, or any combination thereof.

14. The antennae assembly electrode of claim 6, wherein the linear chain ligands include poly-oxyethylene, tri-n-alkylammonium halide, N,N,N',N'-tetrabutyl-3,6-dioxaoctanedi (thioamide), N,N,N',N'-tetracyclohexyl-3-oxapentadienediamide, alkyl-4-trifluoroacetylbenzoate, triidodecylamine, or any combination thereof.

15. The antennae assembly electrode of claim 3, wherein the fill molecules are semiconductor polymers comprising donor-acceptor pairs.

16. The antennae assembly electrode of claim 15, wherein the semiconductor polymers comprise donor-acceptor pairs including semicarbazole/TCNQ, ionene/iodine, or any combination thereof.

17. The antennae assembly electrode of claim 3, wherein the fill molecules comprise conductive polymers.

18. The antennae assembly electrode of claim 17, wherein the conductive polymers comprise a polypyrrole, a polyaniline, a polythiophene, a poly-p-phenylene, a polyacetylene, or any combination thereof.

19. The antennae assembly electrode of claim 3, wherein at least two of the doped MWNT comprise different fill molecules.

20. The antennae assembly electrode of claim 3, wherein the fill molecules include a chemical agent capable of responding to a chemical or an electrical signal.

21. The antennae assembly electrode of claim 2, wherein the assembly of doped MWNT comprise a plurality of MWNT having a cladding.

22. The antennae assembly electrode of claim 21, wherein the cladding includes a dielectric, an ion conducting polymer, an electron conducting polymer, an ionophore polymer dopant, a redox-mediator dopant, or any combination thereof.

23. The antennae assembly electrode of claim 22, wherein the dielectric includes a polyolefin polymer, a polyaliphatic polymer, a polysiloxane polymer, a polyurethane polymer, a polyvinylchloride polymer, alumina, or any combination thereof.

24. The antennae assembly electrode of claim 22, wherein the ion conducting polymer includes nafion, polystyrene sulfonate, polyvinylpyridinium, or any combination thereof.

25. The antennae assembly electrode of claim 22, wherein the electron conducting polymer includes a chemically doped polymer, an electrochemically doped polymer, a redox electroactive polymer, or any combination thereof.

26. The antennae assembly electrode of claim 25, wherein the doped polymer includes a polyionine, a polysilicon, a polysemicarbazole, a polyphenylene, a polyacetylene, a polyphenylene sulfide, a polythiophene, or any combination thereof.

27. The antennae assembly electrode of claim 26, wherein the doped polymer includes a dopant, the dopant comprising $AsF_5$, $I_2$, Li, K, $BF_{6-}$, $PF_{6-}$, or any combination thereof.

28. The antennae assembly electrode of claim 25, wherein the electrochemically doped polymer includes a polypyrrole, a polythiophene, a polyphenylquinone, a polyaniline, or any combination thereof.

29. The antennae assembly electrode of claim 25, wherein the redox electroactive polymers include polyviologen, polyvinylferrocene, poly-Ru(bpy)3++, or any combination thereof.

30. The antennae assembly electrode of claim 22, wherein the ionophore polymer dopant includes a crown ether, a cryptand, a spherand, a rotaxane, an antibiotic, a non-cyclic ligand, or any combination thereof.

31. The antennae assembly electrode of claim 22, wherein the redox-mediator dopant includes Ru(bpy)3++, Br2/Br−, Fe(phen)3+++, Co(terpy)2+++, Fe(CN)6(3−), Ru(NH.sub.3)6+++, quinone, hydroquinone, methylviologen, tetracyanoquinodimethane, benzophenone, ferrocene, tetramethyl-p-phenylenediamine, tetrathiafulvalene, tri-N-p-tolylamine, or any combination thereof.

32. The antennae assembly electrode of claim 21, wherein the cladding comprises one or more functional reactive groups residing upon a surface of the cladding.

33. The antennae assembly of claim 32, wherein the functional reactive groups include an oxide, a hydroxide, a carboxylic acid, an ester, an ether, a carbonyl, an amine, an amide, an epoxide, a halide, or any combination thereof.

34. The antennae assembly of claim 21, wherein the cladding includes a linker attaching the cladding to the doped MWNT.

35. The antennae assembly of claim 34, wherein the linker includes a Schiff base, a carbodi-imide, an amide, or any combination thereof.

36. The antennae assembly of claim 21, wherein the cladding is linked to a selective functionality on the surface of one or more of the MWNT.

37. The antennae assembly of claim 36, wherein the selective functionality on the surface of one or more of the MWNT includes a protein, a phospholipid, a nucleic acid, an electron mediator, an ionophore, or any combination thereof.

38. The antennae assembly of claim 37, wherein the protein includes an enzyme, an antibody, or any combination thereof.

39. The antennae assembly of claim 37, wherein the nucleic acid includes an oligonucleotide, DNA, RNA, or any combination thereof.

40. The antennae assembly electrode of claim 21, wherein at least two of the doped MWNT comprise different claddings.

41. The antennae assembly electrode of claim 21, wherein the cladding includes a chemical agent capable of responding to a chemical or an electrical signal.

42. The antennae assembly electrode of claim 2, wherein the MWNT comprise one or more functional reactive groups covalently attached to the graphene surface of the MWNT.

43. The antennae assembly of claim 42, wherein the functional reactive groups include an oxide, a hydroxide, a carboxylic acid, an ester, an ether, a carbonyl, an amine, an amide, an epoxide, a halide, or any combination thereof.

44. The antennae assembly of claim 42, wherein the functional reactive groups covalently attached to the graphene surface includes a linker attached to the doped MWNT.

45. The antennae assembly of claim 44, wherein the linker includes a Schiff base, a carbodi-imide, an amide, or any combination thereof.

46. The antennae assembly of claim 42, wherein the functional reactive groups covalently attached to the graphene surface includes a selective functionality.

47. The antennae assembly of claim 46, wherein the selective functionality includes a protein, a phospholipids, a nucleic acid, an electron mediator, an ionophore, or any combination thereof.

48. The antennae assembly of claim 47, wherein the protein includes an enzyme, an antibody, an antigen, or any combination thereof.

49. The antennae assembly of claim 47, wherein the nucleic acid includes an oligonucleotide, DNA, RNA, or any combination thereof.

50. The antennae assembly electrode of claim 2, wherein the electrically conductive layer comprises a metal, an electrically conductive polymer, a carbon film, n-type or p-type doped polysilicon, or any combination thereof.

51. The antennae assembly electrode of claim 50, wherein the electrically conductive layer is a lead conductor residing between the substrate and the catalyst.

52. The antennae assembly electrode of claim 2, wherein the electrically conductive layer comprises Pt, Au, Ti, W, V, Mo, or any combination thereof.

53. The antennae assembly electrode of claim 2, wherein the electrically conductive layer comprises a CVD-deposited metal.

54. The antennae assembly electrode of claim 53, wherein the CVD-deposited metal comprises TiW, Mo, TiN, or any combination thereof.

55. The antennae assembly electrode of claim 2, wherein the electrically conductive layer is characterized as having a layer thickness in the range of from about 1 nanometer to about 1000 nanometers.

56. The antennae assembly electrode of claim 2, wherein the electrically conductive layer is characterized as having a layer thickness in the range of from about 10 nanometers to about 100 nanometers.

57. The antennae assembly electrode of claim 2, wherein the electrically conductive layer is characterized as having a layer thickness in the range of from about 50 nanometers to about 100 nanometers.

58. The antennae assembly electrode of claim 2, wherein the catalyst comprises Ni, Co, Fe, Ru, Rh, Pd, Os, Ir, metal alloys or any combination thereof.

59. The antennae assembly electrode of claim 58, wherein the catalyst is derived from an organo-metallic precursor, an iron-phthalocyanine, a cobalt-phthalocyanine, or any combination thereof.

60. The antennae assembly electrode of claim 58, wherein the catalyst comprises a catalyst capable of growing MWNT.

61. The antennae assembly electrode of claim 60, wherein the catalyst capable of growing MWNT includes nickel, cobalt, iron, or any combination thereof.

62. The antennae assembly electrode of claim 2, wherein the catalyst is characterized as having a layer thickness in the range of from about 1 nanometer to about 10,000 nanometers.

63. The antennae assembly electrode of claim 2, wherein the catalyst is characterized as having a layer thickness in the range of from about 500 nanometers to about 1000 nanometers.

64. The antennae assembly electrode of claim 2, wherein the catalyst is characterized as having a layer thickness in the range of from about 700 nanometers to about 900 nanometers.

65. The antennae assembly electrode of claim 2, wherein the doped antennae assembly comprises a plurality of doped MWNT perpendicularly oriented to the substrate.

66. The antennae assembly electrode of claim 65, wherein the doped MWNTs are oriented parallel to each other.

67. The antennae assembly electrode of claim 2, wherein the doped antennae assembly comprises a doped MWNT carpet, a doped MWNT array, or any combination thereof.

68. The antennae assembly electrode of claim 67, wherein the electrically conductive layer comprises a single contiguous conductive layer, and the doped MWNT carpet is in electrical communication with the single contiguous conductive layer.

69. The antennae assembly electrode of claim 67, wherein the doped MWNT array comprises an aligned array of nanotubes of a defined geometry and pitch oriented with respect to the electrically conductive layer.

70. The antennae assembly electrode of claim 2, wherein the assembly of doped MWNT comprises an array of doped MWNT.

71. The antennae assembly electrode of claim 2, wherein the catalyst is patterned on the electrically conductive layer, and the assembly of doped MWNT is attached to the patterned catalyst.

72. The antennae assembly electrode of claim 2, wherein the catalyst is patterned as an array of islands, stripes, circles, squares, rings, triangles, polygons, or any combination thereof.

73. The use of the antennae assembly electrode of claim 1 as a working electrode in an electrolytic cell or sensor.

74. The antennae assembly electrode of claim 1, wherein the substrate comprises quartz, aluminum oxide, alumina, silicon, a ceramic, chromium, iridum, aluminum, niobium, tantalum, titanium, tungsten, carbon, silicon oxide, silicon carbide, brass, bronze, silver, gold, glass, indium tin oxide, graphite, platinum, magnesium aluminum oxide, platinum crucible, magnesium aluminate spinel, or any oxide, alloy, or combination thereof.

75. The antennae assembly electrode of claim 1, further comprising one or more layers of quartz, aluminum oxide, alumina, silicon, a ceramic, chromium, iridum, aluminum, niobium, tantalum, titanium, tungsten, carbon, silicon oxide, silicon carbide, brass, bronze, silver, gold, glass, indium tin oxide, graphite, platinum, magnesium aluminum oxide, platinum crucible, magnesium aluminate spinel, or any oxide, alloy, or combination thereof.

76. A sensor comprising the antennae assembly electrode of claim 1.

77. A field effect transistor comprising the antennae assembly electrode of claim 1.

78. The antennae assembly electrode of claim 21, wherein the electrode includes a linear chain ligand.

79. The antennae assembly electrode of claim 78, wherein the linear chain ligand comprises poly(oxyethylene), tri-n-alkylammonium, or a combination thereof.

80. The antennae assembly of claim 45, wherein the linker comprises a tether.

81. The antennae assembly of claim 80, wherein tether comprises an alkane, an olefin, a linear hydrocarbon, a branched hydrocarbon, or any combination thereof.

82. The antennae assembly electrode of claim 69, wherein the pitch is defined as the ratio of the center to center distance of the MWNTs to the diameter of a MWNT, the pitch being in the range of from about 1: 1 to about 100: 1.

83. The antennae assembly electrode of claim 69, wherein the length to diameter aspect ratio of the MWNTs is in the range of from about 1: 1 to about 10,000: 1.

84. An antennae assembly electrode, comprising:
an electrically conductive layer at least partially surmounting a substrate;
a planar protective layer, said protective layer having a plurality of contact holes; and
an assembly of antennae vertically oriented with respect to the electrically conductive layer and electrically connected with the electrically conductive layer through the contact holes, wherein each of the antennae comprises a MWNT comprising:
a base end attached to the electrically conductive layer,
a mid-section comprising an outer surface surrounding a lumen, wherein a majority of the outer surface of the mid-section is in fluidic contact with an environment in contact with a top end of the antennae; and
the top end disposed opposite to the base end, wherein neither the mid-section nor the top end are connected to the electrically conductive layer.

85. A sensor comprising the antennae assembly electrode according to claim 84.

86. A field-effect transistor comprising the antennae assembly electrode according to claim 84.

87. An antennae assembly electrode, comprising:
an electrically conductive layer at least partially surmounting a substrate, said electrically conductive layer having a surface defining a first plane;
a planar protective layer disposed parallel to the first plane, said protective layer having a plurality of contact holes; and
an assembly of doped antennae, wherein each of the doped antennae is normal to said first plane, electrically connected with the electrically conductive layer through the contact holes, and comprises a doped MWNT comprising:
a base end attached to the electrically conductive layer, a mid-section comprising an outer surface surrounding a lumen, wherein said mid-section extends from said base end to a top end and wherein a majority of the outer surface of the mid-section is in fluidic contact with an environment in contact with the top end of the antennae;

the top end disposed opposite to the base end, wherein neither the mid-section nor the top end are connected to the electrically conductive layer; and a dopant attached to or contained within the lumen, a dopant attached to or contained within the outer surface, a dopant attached to or contained within the top end, or any combination thereof.

* * * * *